(12) United States Patent
Benatuil et al.

(10) Patent No.: US 10,174,121 B2
(45) Date of Patent: Jan. 8, 2019

(54) ANTI-CD40 ANTIBODIES

(71) Applicant: AbbVie Inc., North Chicago, IL (US)

(72) Inventors: Lorenzo Benatuil, Northborough, MA (US); Bradford L. McRae, Northborough, MA (US); Chung-Ming Hsieh, Newton, MA (US); Rui Wang, Newton, MA (US)

(73) Assignee: ABBVIE, INC., North Chicago, IL (US)

( * ) Notice: Subject to any disclaimer, the term of this patent is extended or adjusted under 35 U.S.C. 154(b) by 310 days.

(21) Appl. No.: 15/167,598

(22) Filed: May 27, 2016

(65) Prior Publication Data

US 2016/0347850 A1    Dec. 1, 2016

Related U.S. Application Data

(60) Provisional application No. 62/168,425, filed on May 29, 2015.

(51) Int. Cl.

| | | |
|---|---|---|
| *C07K 16/28* | (2006.01) | |
| *A61K 39/395* | (2006.01) | |
| *G01N 33/566* | (2006.01) | |
| *A61K 39/00* | (2006.01) | |

(52) U.S. Cl.

CPC ........ *C07K 16/2878* (2013.01); *G01N 33/566* (2013.01); *A61K 2039/505* (2013.01); *A61K 2039/545* (2013.01); *C07K 2317/24* (2013.01); *C07K 2317/33* (2013.01); *C07K 2317/34* (2013.01); *C07K 2317/565* (2013.01); *C07K 2317/567* (2013.01); *C07K 2317/75* (2013.01); *C07K 2317/76* (2013.01); *C07K 2317/92* (2013.01); *G01N 2333/70578* (2013.01)

(58) Field of Classification Search
None
See application file for complete search history.

(56) References Cited

U.S. PATENT DOCUMENTS

| | | |
|---|---|---|
| 5,182,368 A | 1/1993 | Ledbetter et al. |
| 5,247,069 A | 9/1993 | Ledbetter et al. |
| 5,674,492 A | 10/1997 | Armitage et al. |
| 5,677,165 A | 10/1997 | de Boer et al. |
| 5,786,456 A | 7/1998 | Ledbetter et al. |
| 5,801,227 A | 9/1998 | Fanslow, III et al. |
| 5,849,898 A | 12/1998 | Seed et al. |
| 6,051,228 A | 4/2000 | Aruffo et al. |
| 6,315,998 B1 | 11/2001 | de Boer et al. |
| 6,720,182 B1 | 4/2004 | Savitzky et al. |
| 6,994,994 B1 | 2/2006 | Savitzky et al. |
| 7,148,061 B2 | 12/2006 | Lenardo et al. |
| 7,193,064 B2 | 3/2007 | Mikayama et al. |
| 7,445,780 B2 | 11/2008 | Chu et al. |
| 8,277,810 B2 | 10/2012 | Long et al. |
| 8,591,900 B2 | 11/2013 | Barrett et al. |
| 8,669,352 B2 | 3/2014 | den Hartog et al. |
| 2004/0120948 A1 | 6/2004 | Mikayama et al. |
| 2004/0258681 A1 | 12/2004 | Savitzky et al. |
| 2007/0292439 A1 | 12/2007 | Luqman |
| 2009/0117111 A1 | 5/2009 | Aukerman et al. |
| 2009/0202531 A1 | 8/2009 | Aukerman et al. |
| 2012/0121585 A1 | 5/2012 | Heusser et al. |
| 2012/0301488 A1 | 11/2012 | Zhang et al. |
| 2014/0093497 A1 | 4/2014 | Reimann et al. |
| 2014/0099317 A1 | 4/2014 | Suri et al. |
| 2014/0105907 A1 | 4/2014 | Takahashi et al. |
| 2014/0120103 A1 | 5/2014 | Zhang et al. |

FOREIGN PATENT DOCUMENTS

| | | |
|---|---|---|
| EP | 0330191 B1 | 10/1996 |
| EP | 1694360 B1 | 8/2010 |
| WO | 1994004570 A1 | 3/1994 |
| WO | 2001034649 A2 | 5/2001 |
| WO | 2003029296 A1 | 4/2003 |
| WO | 2003070768 A2 | 8/2003 |
| WO | 2005105840 A2 | 11/2005 |
| WO | 2005108428 A2 | 11/2005 |
| WO | 2007124299 A2 | 11/2007 |
| WO | 2011/123489 A2 | 10/2011 |

OTHER PUBLICATIONS

International Search Report and Written Opinion issued by the European Patent Office relating to International Application No. PCT/US2016/034716, dated Aug. 8, 2016.
Written Opinion of the International Preliminary Examining Authority, issued by the European Patent Office, dated May 15, 2017.
Response to Written Opinion, PCT Demand under Article 31 of the Patent Cooperation Treaty and Fee Calculation relating to International Application No. PCT/US2016/034716 submitted to the European Patent Office on Mar. 29, 2017.
Bensinger, et al., "A Phase 1 Study of Lucatumumab, a Fully Human Anti-CD40 Antagonist Monoclonal Antibody Administered Intravenously to Patients with Relapsed or Refractory Multiple Myeloma," British Journal of Haematology, 2012:159, 58-66.
Ma et al., "Pharmacokinetics and Pharmacodynamics of ASKP 1240, a Fully Human Anti-CD40 Antibody, in Normal and Renal Transplanted Cynomolgus Monkeys," Transplantation, www.transplantjournal.com, 2014 (8 pages).
Yamniuk, et al., "Functional Antagonism of Human CD40 Achieved by Targeting a Unique Speciest-Specific Epitope," J Mol Biol, 2016, 426:2860-2879.
S. Perper, et al. "Prophylactic and Therapeutic Administration of an Anti-CD40 Antagonist Antibody Blocks and Reverses Proteinuria and Nephritis in NZB/W-F, Mice," THU0222 Poster, Jun. 15, 2017.
S. Perper, et al. "Prophylactic and Therapeutic Administration of an Anti-CD40 Antagonist Antibody Blocks and Reverses Proteinuria and Nephritis in NZB/W-F, Mice," THU0222 Abstract (Jun. 2017).
G. Lynch, et al. "Antagonism of CD40 Effectively Blocks Disease Onset and Progression in a Murine Model of Colitis," TU1868 Poster, presented at the 2016 DDW, May 21, 2016, San Diego, CA.
G. Lynch, et al. "Tu1868 Antagonism of CD40 Effectively Blocks Disease Onset and Progression in a Murine Model of Colitis," Gastroenterology, vol. 150, Issue 4, S964 (Apr. 2016).

*Primary Examiner* — Phillip Gambel

(74) *Attorney, Agent, or Firm* — Womble Bond Dickinson (US) LLP; Cristin H. Cowles; Kevin A. Fiala

(57) ABSTRACT

The present invention encompasses antagonist anti-CD40 antibodies and antigen-binding portions thereof. Specifically, the invention relates to humanized anti-CD40 antibodies. In certain embodiments, antibodies of the invention neutralize human CD40 (hCD40) activity. Antibodies, or antibody portions, of the invention are useful for detecting CD40 and for inhibiting CD40 activity, e.g., in a human subject suffering from a disorder in which CD40 activity is detrimental.

21 Claims, 24 Drawing Sheets

Specification includes a Sequence Listing.

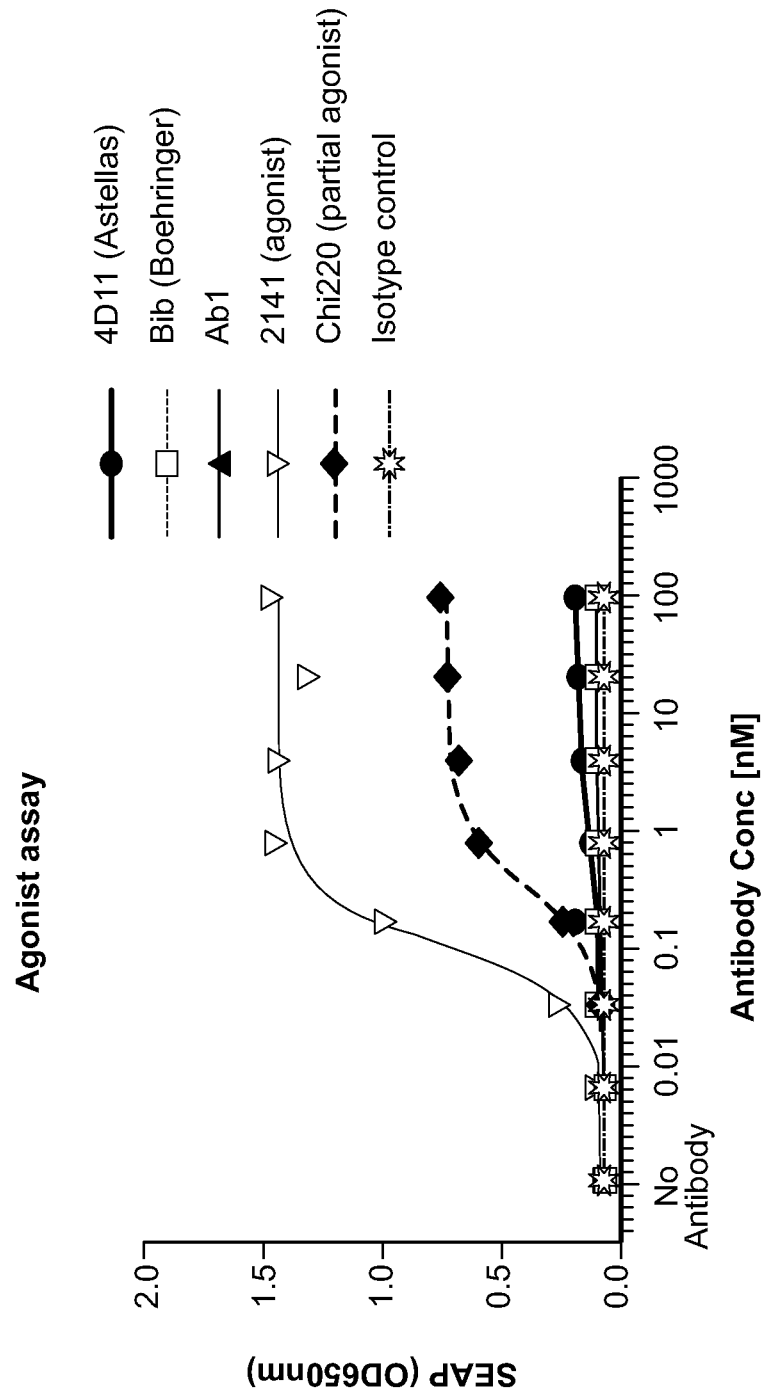

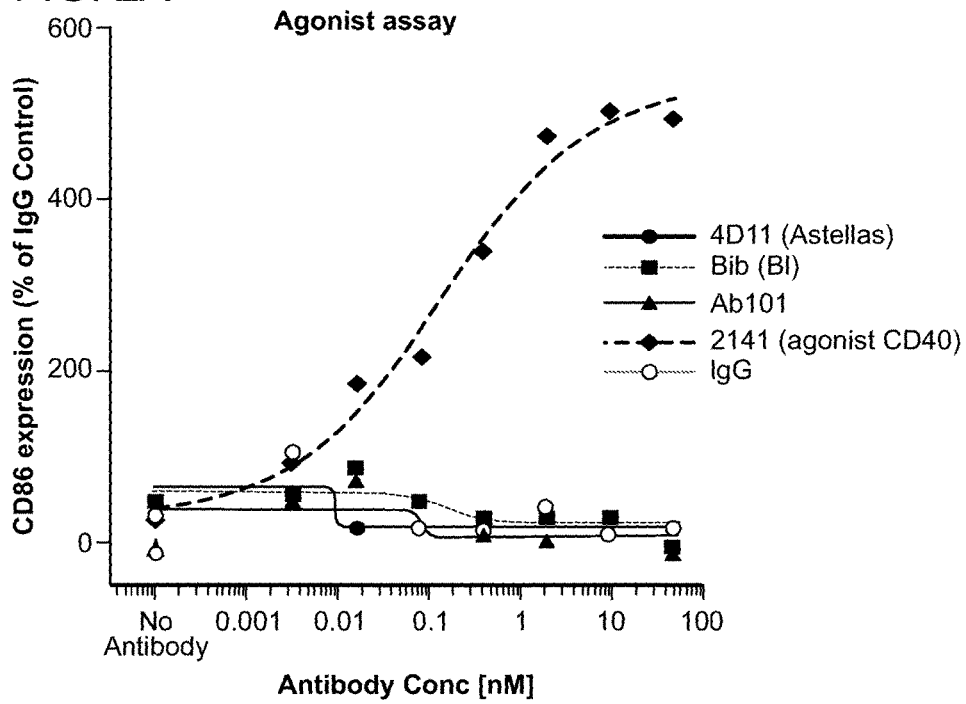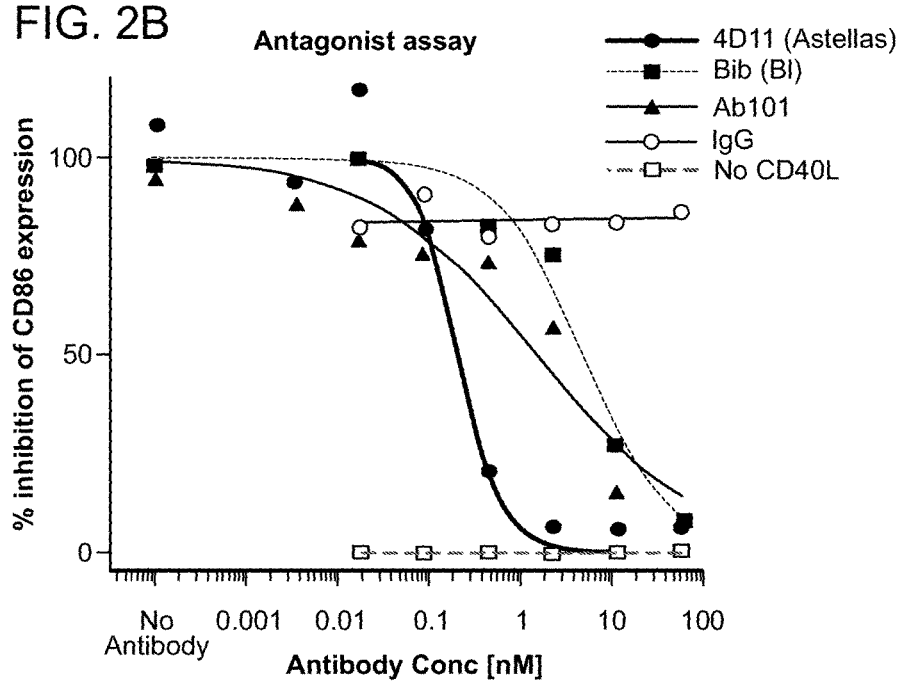

FIG. 4A

```
                             1                                                          50
Ab3 SEQ ID NO:48   (1)  DIVMTQAAPSVSVIPGESVSISCRSSKSLLHS-NGNTYLYWFLQRPGQSP
Ab1 SEQ ID NO:9    (1)  DIVMTQSPSSLTVTAGEMVTMSCKSSQSLLNSGNQKNYLTWFQQKPGQPP
Ab2 SEQ ID NO:76   (1)  DIVMTQSPSSLTVTAGEKVTMSCKSSQSLLNSGNQKNYLTWFQQKPGQPP
             Consensus   DIVMTQSPSSLTVTAGE VTMSCKSSQSLLNSGNQKNYLTWFQQKPGQPP
                                         R  K           H  -  GNT Y 51                                                         100
Ab3                (50) QYLIYRMSTLASGVPDRFSGSGSGTAFTLRISRVEAEDVGVYYCMQHLEY
Ab1                (51) KLLIYWASTRESGVPDRFAGSGSGTDFTLTISSVQAEDLAVYYCQNDYTY
Ab2                (51) KLLIYWASTRESGVPDRFTGSGSGTDFTLTISSVQAEDLAVYYCQNDYTY
             Consensus  KLLIYWASTRESGVPDRF SGSGSGTDFTLTISSVQAEDLAVYYCQNDYTY
                          RM    LA                                      MQHLE 101
Ab3               (100) PLTFGAGTKLELK
Ab1               (101) PLTFGAGTKLEIK
Ab2               (101) PLTFGAGTKLELK
             Consensus  PLTFGAGTKLELK
```

FIG. 4B

```
                         1                                                  50
Ab3 SEQ ID NO:44 (100)   QVQLQQSGAELARPGASVKMSCKAFGYTFTSYTMHWVKQRPGQGLEWIGY
Ab1 SEQ ID NO:5  (101)   EVQLVESGGGLVKPGGSLKVSCAASGFTFSDYGMNWVRQAPEKGLEWIAY
Ab2 SEQ ID NO:75 (101)   EVQLVESGGGLVKPGGSLKVSCAASGFTFSDYGMNWVRQSPEKGLEWIAY
        Consensus (101)  EVQLVESGGGLVKPGGSLKVSCAASGFTFSDYGMNWVRQAPEKGLEWIAY
                                                 Y      TS  T   H 51                                                 100
Ab3              (150)   INPSSDYPNYNQKFKDKATLTADKSSSTAYMQLSSLTSEDSAVYYCARWG
Ab1              (151)   ISSGRSNIYYADTVKGRFTISRDNAKNTLFLQMTSLRSEDTAMYYCARSW
Ab2              (151)   ISSGRGNIYYADTVKGRFTISRDNAKNTLFLQMTSLRSEDTAMYYCARSW
        Consensus (151)  ISSGR NIYYADTVKGRFTISRDNAKNTLFLQMTSLRSEDTAMYYCARSW
                         NPSS  YPN NQKF D                                  WG 101
Ab3              (200)   YSFDYWGQGTTLTVSS
Ab1              (201)   GYFDVWGTGTTVTVSS
Ab2              (201)   GYFDVWGTGTTVTVSS
        Consensus (201)  GYFDVWGTGTTVTVSS
                         YS
```

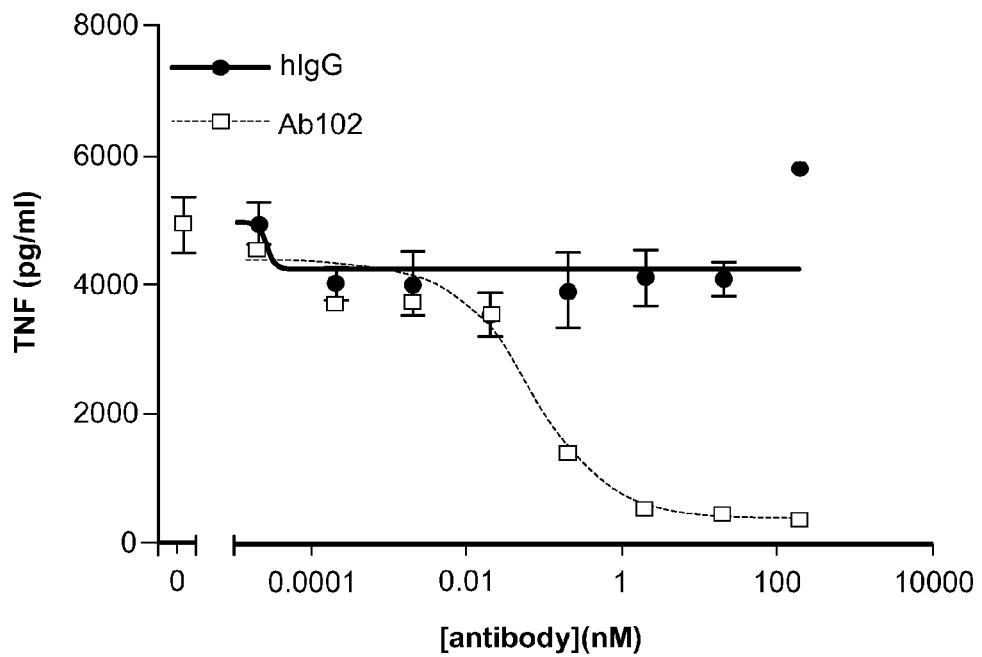
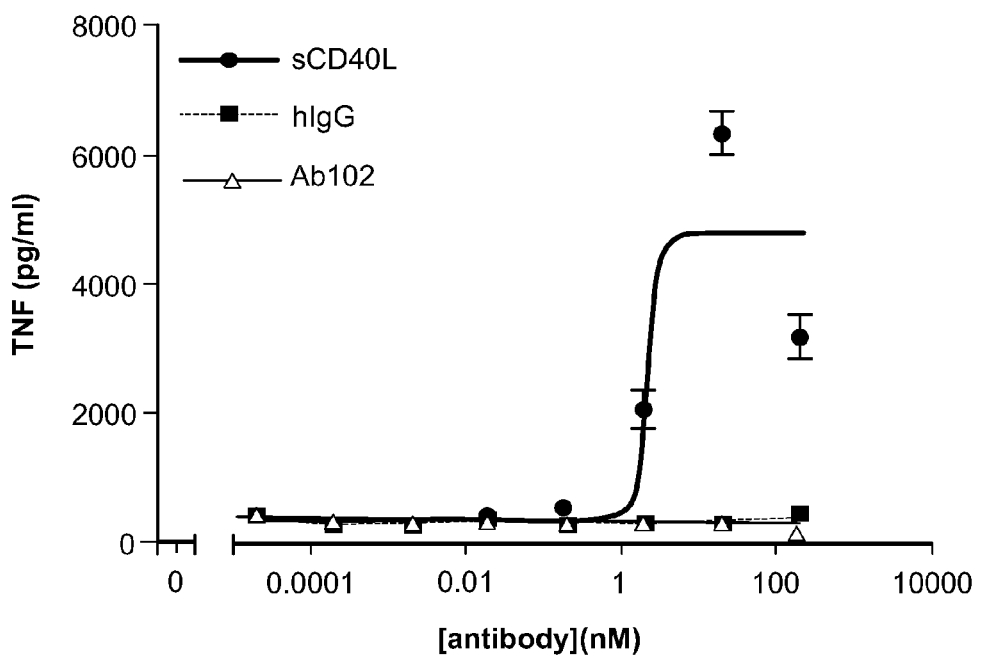

only 1 animal in the 0.5mg/kg group had measurable levels of Ab138

FIG. 10
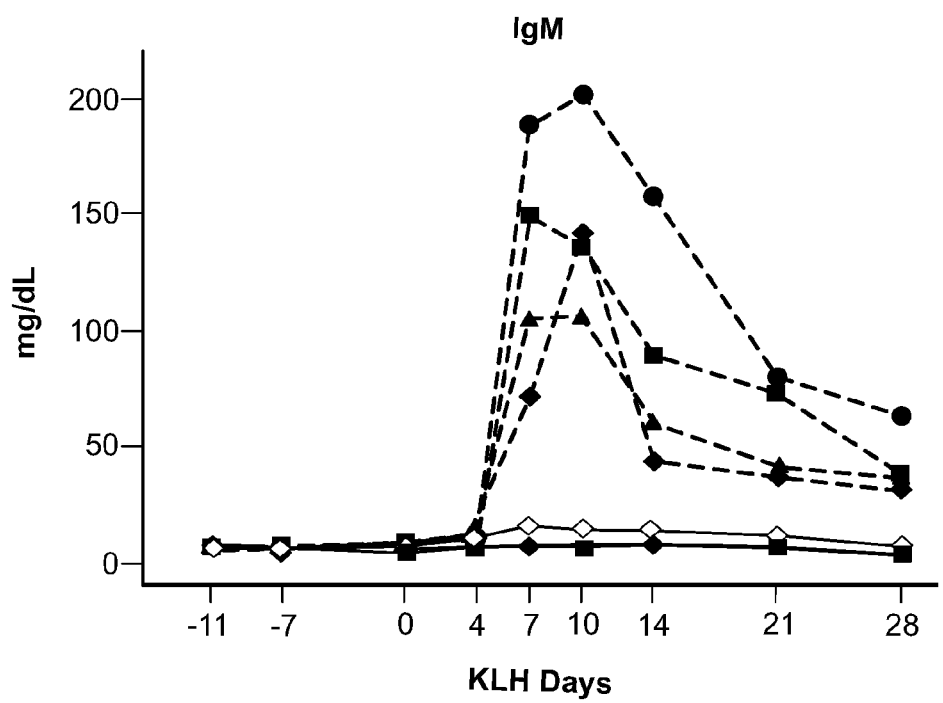
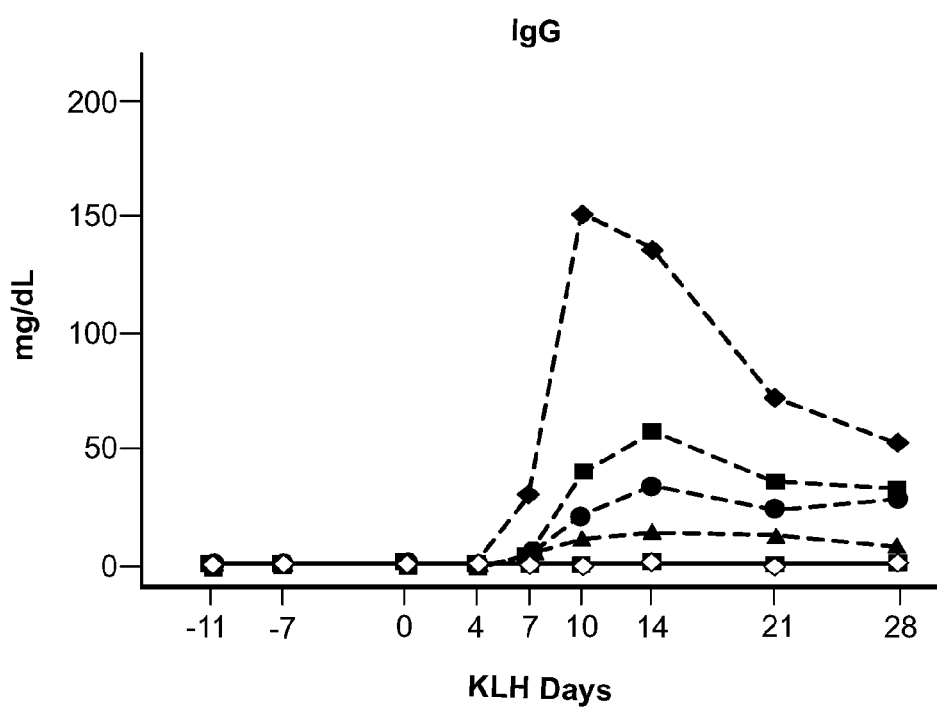

^Survival *p* value <0.05 Log Rank Mandel Cox test
‾Pioceinuna verses respective Vehicle Control

SEQUENCE LISTING

<160> NUMBER OF SEQ IDS NOS: 117

<210> SEQ ID NO 1
<211> LENGTH: 277
<212> TYPE: PRT
<213> ORGANISM: Homo sapiens

<400> SEQUENCE: 1

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

```
Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                    195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Asp Tyr
            20                  25                  30

Gly Met Asn Trp Val Arg Gln Ala Pro Glu Lys Gly Leu Glu Trp Ile
        35                  40                  45

Ala Tyr Ile Ser Ser Gly Arg Ser Asn Ile Tyr Tyr Ala Asp Thr Val
    50                  55                  60

Lys Gly Arg Phe Thr Ile Ser Arg Asp Asn Ala Lys Asn Thr Leu Phe
```

```
                65                  70                  75                  80
Leu Gln Met Thr Ser Leu Arg Ser Glu Asp Thr Ala Met Tyr Tyr Cys
                    85                  90                  95

Ala Arg Ser Trp Gly Tyr Phe Asp Val Trp Gly Thr Gly Thr Thr Val
                100                 105                 110

Thr Val Ser Ser
        115

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Ser Asp Tyr Gly Met Asn
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ile Ser Ser Gly Arg Ser Asn Ile Tyr Tyr Ala Asp Thr Val Lys
1               5                   10                  15

Gly

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Trp Gly Tyr Phe Asp Val
1               5

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Pro Ser Ser Leu Thr Val Thr Ala Gly
1               5                   10                  15

Glu Met Val Thr Met Ser Cys Lys Ser Ser Gln Ser Leu Leu Asn Ser
                20                  25                  30

Gly Asn Gln Lys Asn Tyr Leu Thr Trp Phe Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ala Gly Ser Gly Ser Gly Thr Asp Phe Thr Leu Thr
```

```
                65                  70                  75                  80
Ile Ser Ser Val Gln Ala Glu Asp Leu Ala Val Tyr Tyr Cys Gln Asn
                    85                  90                  95

Asp Tyr Thr Tyr Pro Leu Thr Phe Gly Ala Gly Thr Lys Leu Glu Ile
                100                 105                 110

Lys

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ser Ser Gln Ser Leu Leu Asn Ser Gly Asn Gln Lys Asn Tyr Leu
1               5                   10                  15

Thr

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Asp Tyr Thr Tyr Pro Leu Thr
1               5

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Gly Met Asn Trp Val Arg Gln Ala Pro Gly Lys Gly Leu Glu Trp Val
                35                  40                  45

Ser Tyr Ile Ser Ser Gly Arg Ser Asn Ile Tyr Tyr Ala Asp Thr Val
            50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gln Gly Thr Lys Leu Glu Ile
            100                 105                 110

Lys

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Ser Asn Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gln Gly Thr Lys Leu Glu Ile
            100                 105                 110

Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ser Ser Gln Ser Leu Leu Asn Leu Gly Asn Gln Lys Asn Tyr Leu
1               5                   10                  15

Thr

<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gln Gly Thr Lys Leu Glu Ile
                100                 105                 110

Lys

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ser Ser Gln Ser Leu Leu Asn Thr Gly Asn Gln Lys Asn Tyr Leu
1               5                   10                  15

Thr

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gln Gly Thr Lys Leu Glu Ile
                100                 105                 110

Lys

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ser Ser Gln Ser Leu Leu Asn Arg Gly Asn Gln Lys Asn Tyr Leu
1               5                   10                  15

Thr

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Thr Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
            115

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Asp Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
            115

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

Gly Met Asn Trp Val Arg Gln Ala Pro Gly Lys Gly Leu Glu Trp Ile
            35                  40                  45

Ala Tyr Ile Ser Ser Gly Arg Glu Asn Ile Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Met Asn Trp Val Arg Gln Ala Pro Gly Lys Gly Leu Glu Trp Ile
            35                  40                  45

Ala Tyr Ile Ser Ser Gly Arg Arg Asn Ile Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Met Asn Trp Val Arg Gln Ala Pro Gly Lys Gly Leu Glu Trp Ile
            35                  40                  45

Ala Tyr Ile Ser Ser Gly Arg Val Asn Ile Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

```
Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Leu Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Gly Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115
```

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Ile Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Gln Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 31

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Trp Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Met Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
```

```
                    35                  40                  45
Ala Tyr Ile Ser Ser Gly Arg Lys Asn Ile Tyr Tyr Ala Asp Thr Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Met Asn Trp Val Arg Gln Ala Pro Gly Lys Gly Leu Glu Trp Ile
         35                  40                  45

Ala Tyr Ile Ser Ser Gly Arg His Asn Ile Tyr Tyr Ala Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Met Asn Trp Val Arg Gln Ala Pro Gly Lys Gly Leu Glu Trp Ile
         35                  40                  45

Ala Tyr Ile Ser Ser Gly Arg Phe Asn Ile Tyr Tyr Ala Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
```

```
                     85                  90                  95

Ala Arg Ser Trp Gly Tyr Phe Asp Val Trp Gly Gln Gly Thr Thr Val
                100                 105                 110

Thr Val Ser Ser
        115

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Gly Met Asn Trp Val Arg Gln Ala Pro Gly Lys Gly Leu Glu Trp Ile
            35                  40                  45

Ala Tyr Ile Ser Ser Gly Arg Tyr Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
                100                 105                 110

Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Gly Met Asn Trp Val Arg Gln Ala Pro Gly Lys Gly Leu Glu Trp Ile
            35                  40                  45

Ala Tyr Ile Ser Ser Gly Arg Ala Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
                100                 105                 110

Thr Val Ser Ser
        115
```

```
<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Pro Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser
        115

<210> SEQ ID NO 39
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Gly Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

```
              180                 185                 190
Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 40
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95
```

```
Asp Tyr Thr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 41
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Ile
        35                  40                  45

Ala Tyr Ile Ser Ser Gly Arg Gly Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Gly Tyr Phe Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240
```

```
Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Asn His Tyr Thr Gln Lys Ser Leu Ser Leu Ser Pro Gly Lys
        435                 440                 445

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Ser Ser Gly Arg Gly Asn Ile Tyr Tyr Ala Asp Thr Val Lys
1               5                   10                  15

Gly

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Leu
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Thr Tyr Pro Leu Thr Phe Gly Gln Gly Thr Lys Leu Glu Ile
            100                 105                 110

Lys

<210> SEQ ID NO 44
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Gln Ser Gly Ala Glu Leu Ala Arg Pro Gly Ala
 1               5                  10                  15

Ser Val Lys Met Ser Cys Lys Ala Phe Gly Tyr Thr Phe Thr Ser Tyr
             20                  25                  30

Thr Met His Trp Val Lys Gln Arg Pro Gly Gln Gly Leu Glu Trp Ile
         35                  40                  45

Gly Tyr Ile Asn Pro Ser Ser Asp Tyr Pro Asn Tyr Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Trp Gly Tyr Ser Phe Asp Tyr Trp Gly Gln Gly Thr Thr Leu
            100                 105                 110

Thr Val Ser Ser
        115

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Thr Phe Thr Ser Tyr Thr Met His
 1               5                  10

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Ile Asn Pro Ser Ser Asp Tyr Pro Asn Tyr Asn Gln Lys Phe Lys
 1               5                  10                  15

Asp

<210> SEQ ID NO 47
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Gly Tyr Ser Phe Asp Tyr
1               5

<210> SEQ ID NO 48
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ala Ala Pro Ser Val Ser Val Ile Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Tyr Leu Ile Tyr Arg Met Ser Thr Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ser Ser Lys Ser Leu Leu His Ser Asn Gly Asn Thr Tyr Leu Tyr
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Met Ser Thr Leu Ala Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 51

Met Gln His Leu Glu Tyr Pro Leu Thr
1               5

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Asn Pro Ser Ser Asp Tyr Pro Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Ser Phe Asp Tyr Trp Gly Gln Gly Thr Thr Val
                100                 105                 110

Thr Val Ser Ser
            115

<210> SEQ ID NO 53
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Asn Thr Tyr Leu Tyr Trp Tyr Leu Gln Lys Pro Gly Gln Ser
            35                  40                  45

Pro Gln Leu Leu Ile Tyr Arg Met Ser Thr Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
                100                 105                 110

<210> SEQ ID NO 54
<211> LENGTH: 116
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 54

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Asp Tyr Pro Asn Tyr Asn Gln Lys Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Ser Phe Asp Tyr Trp Gly Gln Gly Thr Thr Val
            100                 105                 110

Thr Val Ser Ser
            115

<210> SEQ ID NO 55
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Ile
        35                  40                  45

Gly Tyr Ile Asn Pro Ser Ser Asp Tyr Pro Asn Tyr Asn Gln Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Ser Phe Asp Tyr Trp Gly Gln Gly Thr Thr Val
            100                 105                 110

Thr Val Ser Ser
            115

<210> SEQ ID NO 56
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser

```
                20                  25                  30

Asn Gly Asn Thr Tyr Leu Tyr Trp Phe Leu Gln Lys Pro Gly Gln Ser
            35                  40                  45

Pro Gln Tyr Leu Ile Tyr Arg Met Ser Thr Leu Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Asn Thr Tyr Leu Tyr Trp Tyr Leu Gln Lys Pro Gly Gln Ser
            35                  40                  45

Pro Gln Tyr Leu Ile Tyr Arg Met Ser Thr Leu Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Ile Ser Ser Gly Arg Thr Asn Ile Tyr Tyr Ala Asp Thr Val Lys
 1               5                  10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Ile Ser Ser Gly Arg Asp Asn Ile Tyr Tyr Ala Asp Thr Val Lys
 1               5                  10                  15
```

-continued

Gly

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Ile Ser Ser Gly Arg Glu Asn Ile Tyr Tyr Ala Asp Thr Val Lys
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Ile Ser Ser Gly Arg Arg Asn Ile Tyr Tyr Ala Asp Thr Val Lys
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Ile Ser Ser Gly Arg Val Asn Ile Tyr Tyr Ala Asp Thr Val Lys
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Ile Ser Ser Gly Arg Leu Asn Ile Tyr Tyr Ala Asp Thr Val Lys
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Ile Ser Ser Gly Arg Ile Asn Ile Tyr Tyr Ala Asp Thr Val Lys
1               5                   10                  15

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Ile Ser Ser Gly Arg Gln Asn Ile Tyr Tyr Ala Asp Thr Val Lys
1               5                   10                  15
Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Ile Ser Ser Gly Arg Trp Asn Ile Tyr Tyr Ala Asp Thr Val Lys
1               5                   10                  15
Gly

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Ile Ser Ser Gly Arg Met Asn Ile Tyr Tyr Ala Asp Thr Val Lys
1               5                   10                  15
Gly

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Ile Ser Ser Gly Arg Lys Asn Ile Tyr Tyr Ala Asp Thr Val Lys
1               5                   10                  15
Gly

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Ile Ser Ser Gly Arg His Asn Ile Tyr Tyr Ala Asp Thr Val Lys

-continued

```
1               5                   10                  15

Gly

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile Ser Ser Gly Arg Phe Asn Ile Tyr Tyr Ala Asp Thr Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Ile Ser Ser Gly Arg Tyr Asn Ile Tyr Tyr Ala Asp Thr Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Ile Ser Ser Gly Arg Ala Asn Ile Tyr Tyr Ala Asp Thr Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Ile Ser Ser Gly Arg Pro Asn Ile Tyr Tyr Ala Asp Thr Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Lys Ser Ser Gln Ser Leu Leu Asn Pro Gly Asn Gln Lys Asn Tyr Leu
1               5                   10                  15

Thr

<210> SEQ ID NO 75
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Asp Tyr
            20                  25                  30

Gly Met Asn Trp Val Arg Gln Ser Pro Glu Lys Gly Leu Glu Trp Ile
        35                  40                  45

Ala Tyr Ile Ser Ser Gly Arg Gly Asn Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Trp Gly Tyr Phe Asp Val Trp Gly Thr Gly Thr Thr Val
            100                 105                 110

Thr Val Ser Ser
        115

<210> SEQ ID NO 76
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Leu Thr Phe Gly Ala Gly Thr Lys Leu Glu Leu
            100                 105                 110

Lys

<210> SEQ ID NO 77
<211> LENGTH: 113
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Pro
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gln Gly Thr Lys Leu Glu Ile
            100                 105                 110

Lys

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Phe or Tyr
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Asp or Ser
<220> FEATURE:
<221> NAME/KEY: MOD_RES
<222> LOCATION: (8)..(8)
<223> OTHER INFORMATION: Gly or Thr
<220> FEATURE:
<221> NAME/KEY: MOD_RES
<222> LOCATION: (10)..(10)
<223> OTHER INFORMATION: Asn or His

<400> SEQUENCE: 78

Gly Xaa Thr Phe Xaa Xaa Tyr Xaa Met Xaa
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Ser or Asn
<220> FEATURE:
<221> NAME/KEY: MOD_RES
<222> LOCATION: (4)..(4)
<223> OTHER INFORMATION: Ser or Pro
```

```
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Arg or Ser
<220> FEATURE:
<221> NAME/KEY: MOD_RES
<222> LOCATION: (7)..(7)
<223> OTHER INFORMATION: Asp, Ser or Gly
<220> FEATURE:
<221> NAME/KEY: MOD_RES
<222> LOCATION: (8)..(8)
<223> OTHER INFORMATION: Asn or Tyr
<220> FEATURE:
<221> NAME/KEY: MOD_RES
<222> LOCATION: (9)..(9)
<223> OTHER INFORMATION: Ile or Pro
<220> FEATURE:
<221> NAME/KEY: MOD_RES
<222> LOCATION: (10)..(10)
<223> OTHER INFORMATION: Tyr or Asn
<220> FEATURE:
<221> NAME/KEY: MOD_RES
<222> LOCATION: (12)..(12)
<223> OTHER INFORMATION: Ala or Asn
<220> FEATURE:
<221> NAME/KEY: MOD_RES
<222> LOCATION: (13)..(13)
<223> OTHER INFORMATION: Asp or Gln
<220> FEATURE:
<221> NAME/KEY: MOD_RES
<222> LOCATION: (14)..(14)
<223> OTHER INFORMATION: Thr or Lys
<220> FEATURE:
<221> NAME/KEY: MOD_RES
<222> LOCATION: (15)..(15)
<223> OTHER INFORMATION: Val or Phe
<220> FEATURE:
<221> NAME/KEY: MOD_RES
<222> LOCATION: (17)..(17)
<223> OTHER INFORMATION: Gly or Asp

<400> SEQUENCE: 79

Tyr Ile Xaa Xaa Xaa Xaa Xaa Xaa Xaa Xaa Tyr Xaa Xaa Xaa Xaa Lys
1               5                   10                  15

Xaa

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ser or Trp
<220> FEATURE:
<221> NAME/KEY: MOD_RES
<222> LOCATION: (2)..(2)
<223> OTHER INFORMATION: Trp or Gly
<220> FEATURE:
<221> NAME/KEY: MOD_RES
<222> LOCATION: (3)..(3)
<223> OTHER INFORMATION: Gly or Tyr
<220> FEATURE:
<221> NAME/KEY: MOD_RES
<222> LOCATION: (4)..(4)
<223> OTHER INFORMATION: Tyr or Ser

<400> SEQUENCE: 80
```

```
Xaa Xaa Xaa Xaa Phe Asp Val
1               5
```

<210> SEQ ID NO 81
<211> LENGTH: 105
<212> TYPE: PRT
<213> ORGANISM: Homo sapiens

<400> SEQUENCE: 81

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 82
<211> LENGTH: 30
<212> TYPE: PRT
<213> ORGANISM: Homo sapiens

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30
```

<210> SEQ ID NO 83
<211> LENGTH: 14
<212> TYPE: PRT
<213> ORGANISM: Homo sapiens

<400> SEQUENCE: 83

```
Trp Val Arg Gln Ala Pro Gly Gln Gly Leu Glu Trp Met Gly
1               5                   10
```

<210> SEQ ID NO 84
<211> LENGTH: 32
<212> TYPE: PRT
<213> ORGANISM: Homo sapiens

<400> SEQUENCE: 84

```
Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
                20                  25                  30
```

<210> SEQ ID NO 85
<211> LENGTH: 11
<212> TYPE: PRT
<213> ORGANISM: Homo sapiens

<400> SEQUENCE: 85

```
Trp Gly Gln Gly Thr Thr Val Thr Val Ser Ser
1               5                   10
```

<210> SEQ ID NO 86
<211> LENGTH: 14
<212> TYPE: PRT
<213> ORGANISM: Homo sapiens

<400> SEQUENCE: 86

```
Trp Val Arg Gln Ala Pro Gly Gln Arg Leu Glu Trp Met Gly
1               5                   10
```

<210> SEQ ID NO 87
<211> LENGTH: 32
<212> TYPE: PRT
<213> ORGANISM: Homo sapiens

<400> SEQUENCE: 87

```
Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
                20                  25                  30
```

<210> SEQ ID NO 88
<211> LENGTH: 11
<212> TYPE: PRT
<213> ORGANISM: Homo sapiens

<400> SEQUENCE: 88

```
Trp Gly Gln Gly Thr Leu Val Thr Val Ser Ser
1               5                   10
```

<210> SEQ ID NO 89
<211> LENGTH: 30
<212> TYPE: PRT
<213> ORGANISM: Homo sapiens

<400> SEQUENCE: 89

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
                20                  25                  30
```

<210> SEQ ID NO 90
<211> LENGTH: 15
<212> TYPE: PRT
<213> ORGANISM: Homo sapiens

<400> SEQUENCE: 90

```
Trp Ile Arg Gln Pro Pro Gly Lys Ala Leu Glu Trp Leu Ala His
1               5                   10                  15
```

<210> SEQ ID NO 91
<211> LENGTH: 32
<212> TYPE: PRT
<213> ORGANISM: Homo sapiens

<400> SEQUENCE: 91

```
Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
                20                  25                  30
```

```
<210> SEQ ID NO 92
<211> LENGTH: 30
<212> TYPE: PRT
<213> ORGANISM: Homo sapiens

<400> SEQUENCE: 92

Gln Val Thr Leu Arg Glu Ser Gly Pro Ala Leu Val Lys Pro Thr Gln
1               5                   10                  15

Thr Leu Thr Leu Thr Cys Thr Leu Tyr Gly Phe Ser Leu Ser
            20                  25                  30

<210> SEQ ID NO 93
<211> LENGTH: 14
<212> TYPE: PRT
<213> ORGANISM: Homo sapiens

<400> SEQUENCE: 93

Trp Ile Arg Gln Pro Pro Gly Lys Ala Leu Glu Trp Leu Ala
1               5                   10

<210> SEQ ID NO 94
<211> LENGTH: 32
<212> TYPE: PRT
<213> ORGANISM: Homo sapiens

<400> SEQUENCE: 94

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 95
<211> LENGTH: 32
<212> TYPE: PRT
<213> ORGANISM: Homo sapiens

<400> SEQUENCE: 95

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 96
<211> LENGTH: 23
<212> TYPE: PRT
<213> ORGANISM: Homo sapiens

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 97
<211> LENGTH: 15
<212> TYPE: PRT
<213> ORGANISM: Homo sapiens

<400> SEQUENCE: 97

Trp Tyr Gln Gln Lys Pro Gly Lys Val Pro Lys Leu Leu Ile Tyr
1               5                   10                  15

<210> SEQ ID NO 98
```

<211> LENGTH: 32
<212> TYPE: PRT
<213> ORGANISM: Homo sapiens

<400> SEQUENCE: 98

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 99
<211> LENGTH: 11
<212> TYPE: PRT
<213> ORGANISM: Homo sapiens

<400> SEQUENCE: 99

Phe Gly Gly Gly Thr Lys Val Glu Ile Lys Arg
1               5                   10

<210> SEQ ID NO 100
<211> LENGTH: 32
<212> TYPE: PRT
<213> ORGANISM: Homo sapiens

<400> SEQUENCE: 100

Gly Val Pro Ser Arg Ile Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 101
<211> LENGTH: 23
<212> TYPE: PRT
<213> ORGANISM: Homo sapiens

<400> SEQUENCE: 101

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 102
<211> LENGTH: 15
<212> TYPE: PRT
<213> ORGANISM: Homo sapiens

<400> SEQUENCE: 102

Trp Phe Gln Gln Arg Pro Gly Gln Ser Pro Arg Arg Leu Ile Tyr
1               5                   10                  15

<210> SEQ ID NO 103
<211> LENGTH: 32
<212> TYPE: PRT
<213> ORGANISM: Homo sapiens

<400> SEQUENCE: 103

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 104
<211> LENGTH: 23

<212> TYPE: PRT
<213> ORGANISM: Homo sapiens

<400> SEQUENCE: 104

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 105
<211> LENGTH: 15
<212> TYPE: PRT
<213> ORGANISM: Homo sapiens

<400> SEQUENCE: 105

Trp Tyr Leu Gln Lys Pro Gly Gln Ser Pro Gln Leu Leu Ile Tyr
1               5                   10                  15

<210> SEQ ID NO 106
<211> LENGTH: 11
<212> TYPE: PRT
<213> ORGANISM: Homo sapiens

<400> SEQUENCE: 106

Phe Gly Gln Gly Thr Lys Leu Glu Ile Lys Arg
1               5                   10

<210> SEQ ID NO 107
<211> LENGTH: 100
<212> TYPE: PRT
<213> ORGANISM: Homo sapiens

<400> SEQUENCE: 107

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val
            100

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (4)..(4)
<223> OTHER INFORMATION: Gln or Lys
<220> FEATURE:

```
<221> NAME/KEY: MOD_RES
<222> LOCATION: (8)..(8)
<223> OTHER INFORMATION: Asn or His
<220> FEATURE:
<221> NAME/KEY: VARIANT
<222> LOCATION: (10)..(10)
<223> OTHER INFORMATION: Gly or absent
<220> FEATURE:
<221> NAME/KEY: MOD_RES
<222> LOCATION: (12)..(12)
<223> OTHER INFORMATION: Gln or Gly
<220> FEATURE:
<221> NAME/KEY: MOD_RES
<222> LOCATION: (13)..(13)
<223> OTHER INFORMATION: Lys or Asn
<220> FEATURE:
<221> NAME/KEY: MOD_RES
<222> LOCATION: (14)..(14)
<223> OTHER INFORMATION: Asn or Thr
<220> FEATURE:
<221> NAME/KEY: MOD_RES
<222> LOCATION: (17)..(17)
<223> OTHER INFORMATION: Thr or Tyr

<400> SEQUENCE: 108

Xaa Ser Ser Xaa Ser Leu Leu Xaa Ser Xaa Asn Xaa Xaa Xaa Tyr Leu
1               5                   10                  15

Xaa

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Trp or Arg
<220> FEATURE:
<221> NAME/KEY: MOD_RES
<222> LOCATION: (2)..(2)
<223> OTHER INFORMATION: Ala or Met
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Glu or Ala

<400> SEQUENCE: 109

Xaa Xaa Ser Thr Xaa Xaa Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Gln or Met
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
```

```
<222> LOCATION: (3)..(3)
<223> OTHER INFORMATION: Asp or His
<220> FEATURE:
<221> NAME/KEY: MOD_RES
<222> LOCATION: (4)..(4)
<223> OTHER INFORMATION: Tyr or Leu
<220> FEATURE:
<221> NAME/KEY: MOD_RES
<222> LOCATION: (5)..(5)
<223> OTHER INFORMATION: Thr or Glu

<400> SEQUENCE: 110

Xaa Xaa Xaa Xaa Xaa Tyr Pro Leu Thr
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid other than Thr, Asp, Val, Leu,
      Ile or Met

<400> SEQUENCE: 111

Tyr Ile Ser Ser Gly Arg Xaa Asn Ile Tyr Tyr Ala Asp Thr Val Lys
1               5                   10                  15

Gly

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 112

Tyr Ile Ser Ser Gly Arg Xaa Asn Ile Tyr Tyr Ala Asp Thr Val Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid other than Pro

<400> SEQUENCE: 113

Lys Ser Ser Gln Ser Leu Leu Asn Xaa Gly Asn Gln Lys Asn Tyr Leu
1               5                   10                  15

Thr

<210> SEQ ID NO 114
```

```
<211> LENGTH: 15
<212> TYPE: PRT
<213> ORGANISM: Homo sapiens

<400> SEQUENCE: 114

Trp Tyr Gln Gln Lys Pro Gly Lys Ala Pro Lys Leu Leu Ile Tyr
1               5                   10                  15

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 115

His His His His His His
1               5

<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (18)..(18)
<223> OTHER INFORMATION: Ser, Met or Lys
<220> FEATURE:
<221> NAME/KEY: MOD_RES
<222> LOCATION: (24)..(24)
<223> OTHER INFORMATION: Lys or Arg
<220> FEATURE:
<221> NAME/KEY: MOD_RES
<222> LOCATION: (27)..(27)
<223> OTHER INFORMATION: Gln or Lys
<220> FEATURE:
<221> NAME/KEY: MOD_RES
<222> LOCATION: (31)..(31)
<223> OTHER INFORMATION: Asn or His
<220> FEATURE:
<221> NAME/KEY: VARIANT
<222> LOCATION: (33)..(33)
<223> OTHER INFORMATION: Gly or absent
<220> FEATURE:
<221> NAME/KEY: MOD_RES
<222> LOCATION: (35)..(35)
<223> OTHER INFORMATION: Gln or Gly
<220> FEATURE:
<221> NAME/KEY: MOD_RES
<222> LOCATION: (36)..(36)
<223> OTHER INFORMATION: Lys or Asn
<220> FEATURE:
<221> NAME/KEY: MOD_RES
<222> LOCATION: (37)..(37)
<223> OTHER INFORMATION: Asn or Thr
<220> FEATURE:
<221> NAME/KEY: MOD_RES
<222> LOCATION: (40)..(40)
<223> OTHER INFORMATION: Thr or Tyr
<220> FEATURE:
<221> NAME/KEY: MOD_RES
<222> LOCATION: (56)..(56)
<223> OTHER INFORMATION: Trp or Arg
<220> FEATURE:
<221> NAME/KEY: MOD_RES
<222> LOCATION: (57)..(57)
<223> OTHER INFORMATION: Ala or Met
<220> FEATURE:
<221> NAME/KEY: MOD_RES
<222> LOCATION: (60)..(60)
<223> OTHER INFORMATION: Arg or Leu
```

```
<220> FEATURE:
<221> NAME/KEY: MOD_RES
<222> LOCATION: (61)..(61)
<223> OTHER INFORMATION: Glu or Ala
<220> FEATURE:
<221> NAME/KEY: MOD_RES
<222> LOCATION: (95)..(95)
<223> OTHER INFORMATION: Gln or Met
<220> FEATURE:
<221> NAME/KEY: MOD_RES
<222> LOCATION: (96)..(96)
<223> OTHER INFORMATION: Asn or Gln
<220> FEATURE:
<221> NAME/KEY: MOD_RES
<222> LOCATION: (97)..(97)
<223> OTHER INFORMATION: Asp or His
<220> FEATURE:
<221> NAME/KEY: MOD_RES
<222> LOCATION: (98)..(98)
<223> OTHER INFORMATION: Tyr or Leu
<220> FEATURE:
<221> NAME/KEY: MOD_RES
<222> LOCATION: (99)..(99)
<223> OTHER INFORMATION: Thr or Glu

<400> SEQUENCE: 116

Asp Ile Val Met Thr Gln Ser Pro Ser Ser Leu Thr Val Thr Ala Gly
1               5                   10                  15

Glu Xaa Val Thr Met Ser Cys Xaa Ser Ser Xaa Ser Leu Leu Xaa Ser
            20                  25                  30

Xaa Asn Xaa Xaa Xaa Tyr Leu Xaa Trp Phe Gln Gln Lys Pro Gly Gln
        35                  40                  45

Pro Pro Lys Leu Leu Ile Tyr Xaa Xaa Ser Thr Xaa Xaa Ser Gly Val
50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Xaa Xaa
                85                  90                  95

Xaa Xaa Xaa Tyr Pro Leu Thr Phe Gly Ala Gly Thr Lys Leu Glu Leu
            100                 105                 110

Lys

<210> SEQ ID NO 117
<211> LENGTH: 116
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (27)..(27)
<223> OTHER INFORMATION: Phe or Tyr
<220> FEATURE:
<221> NAME/KEY: MOD_RES
<222> LOCATION: (30)..(30)
<223> OTHER INFORMATION: Ser or Thr
<220> FEATURE:
<221> NAME/KEY: MOD_RES
<222> LOCATION: (31)..(31)
<223> OTHER INFORMATION: Asp or Ser
<220> FEATURE:
<221> NAME/KEY: MOD_RES
<222> LOCATION: (33)..(33)
<223> OTHER INFORMATION: Gly or Thr
<220> FEATURE:
<221> NAME/KEY: MOD_RES
<222> LOCATION: (35)..(35)
<223> OTHER INFORMATION: Asn or His
<220> FEATURE:
```

```
<221> NAME/KEY: MOD_RES
<222> LOCATION: (52)..(52)
<223> OTHER INFORMATION: Ser or Asn
<220> FEATURE:
<221> NAME/KEY: MOD_RES
<222> LOCATION: (53)..(53)
<223> OTHER INFORMATION: Ser or Pro
<220> FEATURE:
<221> NAME/KEY: MOD_RES
<222> LOCATION: (54)..(54)
<223> OTHER INFORMATION: Gly or Ser
<220> FEATURE:
<221> NAME/KEY: MOD_RES
<222> LOCATION: (55)..(55)
<223> OTHER INFORMATION: Arg or Ser
<220> FEATURE:
<221> NAME/KEY: MOD_RES
<222> LOCATION: (56)..(56)
<223> OTHER INFORMATION: Asp, Ser or Gly
<220> FEATURE:
<221> NAME/KEY: MOD_RES
<222> LOCATION: (57)..(57)
<223> OTHER INFORMATION: Asn or Tyr
<220> FEATURE:
<221> NAME/KEY: MOD_RES
<222> LOCATION: (58)..(58)
<223> OTHER INFORMATION: Ile or Pro
<220> FEATURE:
<221> NAME/KEY: MOD_RES
<222> LOCATION: (59)..(59)
<223> OTHER INFORMATION: Tyr or Asn
<220> FEATURE:
<221> NAME/KEY: MOD_RES
<222> LOCATION: (61)..(61)
<223> OTHER INFORMATION: Ala or Asn
<220> FEATURE:
<221> NAME/KEY: MOD_RES
<222> LOCATION: (62)..(62)
<223> OTHER INFORMATION: Asp or Gln
<220> FEATURE:
<221> NAME/KEY: MOD_RES
<222> LOCATION: (63)..(63)
<223> OTHER INFORMATION: Thr or Lys
<220> FEATURE:
<221> NAME/KEY: MOD_RES
<222> LOCATION: (64)..(64)
<223> OTHER INFORMATION: Val or Phe
<220> FEATURE:
<221> NAME/KEY: MOD_RES
<222> LOCATION: (66)..(66)
<223> OTHER INFORMATION: Gly or Asp
<220> FEATURE:
<221> NAME/KEY: MOD_RES
<222> LOCATION: (99)..(99)
<223> OTHER INFORMATION: Ser or Trp
<220> FEATURE:
<221> NAME/KEY: MOD_RES
<222> LOCATION: (100)..(100)
<223> OTHER INFORMATION: Trp or Gly
<220> FEATURE:
<221> NAME/KEY: MOD_RES
<222> LOCATION: (101)..(101)
<223> OTHER INFORMATION: Gly or Tyr
<220> FEATURE:
<221> NAME/KEY: MOD_RES
<222> LOCATION: (102)..(102)
<223> OTHER INFORMATION: Tyr or Ser

<400> SEQUENCE: 117

Glu Val Gln Leu Val Glu Ser Gly Gly Gly Leu Val Lys Pro Gly Gly
 1               5                  10                  15

Ser Leu Lys Val Ser Cys Ala Ala Ser Gly Xaa Thr Phe Xaa Xaa Tyr
             20                  25                  30

Xaa Met Xaa Trp Val Arg Gln Ala Pro Glu Lys Gly Leu Glu Trp Ile
         35                  40                  45
```

-continued

```
Ala Tyr Ile Xaa Xaa Xaa Xaa Xaa Xaa Xaa Tyr Xaa Xaa Xaa Xaa
    50              55                  60

Lys Xaa Arg Phe Thr Ile Ser Arg Asp Asn Ala Lys Asn Thr Leu Phe
65              70                  75                  80

Leu Gln Met Thr Ser Leu Arg Ser Glu Asp Thr Ala Met Tyr Tyr Cys
            85                  90                  95

Ala Arg Xaa Xaa Xaa Xaa Phe Asp Val Trp Gly Thr Gly Thr Thr Val
        100             105                 110

Thr Val Ser Ser
        115
```

ANTI-CD40 ANTIBODIES

RELATED APPLICATIONS

The present invention claims priority to U.S. Provisional Application No. 62/168,425, filed May 29, 2015, the entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 27, 2016, is named 117813-10402_SL.txt and is 88,895 bytes in size.

FIELD OF THE INVENTION

The present invention relates to CD40 (CD40) antibodies, and antigen-binding portions thereof, and their use in the prevention and/or treatment of various diseases.

BACKGROUND OF THE INVENTION

CD40 is a tumor necrosis factor (TNF) receptor family member that plays an important role in B cell development, lymphocyte activation, and antigen presenting cells (APC) function. CD40 expression on epithelium, leukocytes, and vascular endothelium is elevated in organ-specific autoimmune diseases as well as systemic autoimmunity such as systemic lupus erythematosus (SLE). Disruption of the CD40L/CD40 signaling pathway reduces production of proinflammatory cytokines such as IL-23 and TNF, reduces T helper cell differentiation and function, and inhibits macrophage activation in patients with chronic inflammatory diseases such as Crohn's disease. The interaction of CD40 with CD40L induces both humoral and cell-mediated immune responses. CD40 regulates this ligand-receptor pair to activate B cells and other antigen-presenting cells (APC) including dendritic cells (DCs).

CD40 is a 48 kDa type I transmembrane protein (van Kooten, J Leukoc Biol. 2000 January; 67(1):2-17) that is expressed on a wide range of hematopoietic (lymphocytes, monocytes, dendritic cells) and non-hematopoietic (epithelium, endothelium, fibroblasts) cell types. CD40L is expressed primarily on activated T cells, B cells, and platelets. Much of the understanding of CD40/CD40L biology comes from the interaction between APCs (CD40 expression on either dendritic cells (DC) or B cells) and CD40L-expressing T cells. On resting B cells, CD40L engagement drives B cell activation, proliferation, and memory B cell development (Kehry, Immunol. 1996 Apr. 1; 156(7):2345-8). CD40 signaling is also required for immunoglobulin class switching and germinal center formation. The importance of the CD40/CD40L signaling pathway in B cell biology is evident in CD40- or CD40L-deficient mice which lack germinal centers and T-dependent antibody responses are suppressed. However, T-independent IgG responses remain intact in CD40−/− mice suggesting that it is cell-cell interaction that is lacking in these mice. CD40-deficient mice also have deficits in the T cell compartment. Signaling through CD40 on dendritic cells upregulates MHC class II as well as various costimulatory molecules such as CD80 and CD86 and promotes maturation of DC. Mature DC stimulate activation and survival of CD4+ T cells through production of cytokines such as IL-2 and IL-12. Inefficient T cell priming appears to be the primary cause of compromised T-dependent humoral responses in CD40L−/− mice (Grewal, Nature. 1995 Dec. 7; 378(6557):617-20). A similar B cell phenotype can be seen in humans with X-linked hyper IgM syndrome. These patients suffer from primary immunodeficiency due to mutations in the CD40L locus that abrogates CD40/CD40L signaling. These individuals have elevated IgM levels and cannot produce IgA, IgG, and IgE resulting in an increased risk of opportunistic infections (Adriana, J Clin Immunol. 2008 May; 28 Suppl 1:S62-6).

CD40 signaling pathway is central to the conversion of resting or naïve lymphocytes and APCs to an activated/mature phenotype. Although T cell priming and B cell activation can occur in the absence of CD40/CD40L signaling, this pathway is required for generating a robust adaptive immune response. Engagement of CD40 by CD40L results in the recruitment of TNF receptor associated factors (TRAFs) to the cytoplasmic domain of CD40 (Bishop, Adv Exp Med Biol. 2007; 597:131-51). Phosphorylation of various TRAF proteins results in activation of both canonical and non-canonical NFkB pathways. In addition, JAK3 association with CD40 cytoplasmic tail results in STATS activation which induces maturation of DC as well as TNF and IFNγ production. TRAF6-dependent PI3K activation is a critical survival signal in DC while TRAF2/TRAF6 have redundant functions in NFkB activation and upregulation of CD80 expression (Hostager, J Biol Chem. 2003 Nov. 14; 278(46):45382-90). TRAFs 2, 3, 5, and 6 have all been shown to play an important role in immunoglobulin class switching mediated by CD40 signaling (Leo, Proc Natl Acad Sci USA. 1999 Feb. 16; 96(4): 1421-1426).

CD40/CD40L signaling pathway has been implicated in the pathogenesis of many autoimmune diseases including systemic lupus erythematosus (SLE), inflammatory bowel disease (IBD), multiple sclerosis, rheumatoid arthritis, and Sjogren's syndrome (Law and Grewal, Adv Exp Med Biol. 2009; 647:8-36). CD40 expression is elevated on macrophages, endothelium, epithelium, and B cells in tissues damaged by chronic autoimmunity including kidney, intestine, and joints (Borcherding, Am J Pathol. 2010 April; 176(4):1816-27; Sawada-Hase, Am J Gastroenterol. 2000 June; 95(6):1516-23). Soluble CD40L is elevated in patients suffering from SLE, IBD, and Sjogren's syndrome consistent with inflammatory burden in these patients.

Some of the earliest evidence the CD40/CD40L pathway in chronic intestinal inflammation came from preclinical models where anti-CD40L mAbs protected rodents from experimental colitis (de Jong, Gastroenterology. 2000 September; 119(3):715-23; Liu, J Immunol. 2000 Jun. 1; 164 (11):6005-14; Stuber, J Exp Med 1996 Feb. 1, 183(2):693-8). Reduction in disease activity scores were associated with reduced pro-inflammatory cytokine production in the gut and protection from chronic body weight loss. Similar results were observed in animals that were genetically deficient for CD40 or CD40L (de Jong, Gastroenterology. 2000 September; 119(3):715-23). Treatment of mice with anti-CD40L mAbs after disease onset is still effective in reducing disease activity suggesting that this pathway is critical for maintenance of chronic inflammatory disease. In addition, CD40 agonist antibodies are sufficient to drive intestinal inflammation in mice that lack lymphocytes (Uhlig, Immunity 2006 August; 25(2):309-18). More recent data using CD40 siRNA also point to an important role for CD40 signaling in colitis (Arranz, J Control Release. 2013 Feb. 10; 165(3):163-72). In Crohn's disease, lamina propria monocytes and epithelium express high levels of CD40 and CD40+ monocytes are enriched in peripheral blood. Furthermore, polymorphisms in the CD40 locus have been linked to increased susceptibility to IBD. In Crohn's patients treated with anti-TNF antibodies, transcriptional profiling indicates that CD40 mRNA levels decrease in patients with an adequate drug treatment response. However, in patients with a poor response to TNF inhibitors, CD40 mRNA levels are unchanged suggesting that CD40-dependent, TNF-independent pathways may promote inflammation in these patients. Studies suggest that inhibition of CD40 mediated signaling is important in the pathogenesis of IBD as well as other autoimmune diseases. Accordingly, there remains a need for antagonist anti-CD40 antibodies, and antigen-binding portions thereof, that can be used for therapeutic purposes for treating chronic inflammatory diseases and disorders, such Crohn's disease.

SUMMARY OF THE INVENTION

This invention pertains to antagonist anti-CD40 antibodies, or antigen-binding portions thereof. Antibodies of the inventions include, but are not limited to, antagonist humanized antibodies, and antigen-binding portions thereof, that are capable of binding human CD40 and are substantially free of agonist activity.

In a first aspect, the present invention features an isolated antibody, or antigen binding portion thereof, wherein the antibody, or antigen binding fragment thereof, binds an epitope of human CD40 defined by the topographic regions Cys62-Phe67, Gln79-Cys83, Arg90-Thr99, and Thr24-Cys37 of SEQ ID NO:1. In one embodiment, the antibody, or antigen binding portion thereof, is an antagonist antibody. In one embodiment, the antibody, or antigen binding portion thereof, is an antagonist antibody which is substantially free of agonist activity.

In another embodiment, the antibody, or antigen binding portion thereof, comprises a heavy chain variable region comprising a CDR3 having the amino acid sequence of SEQ ID NO: 8 and a light chain variable region comprising a CDR3 having the amino acid sequence of SEQ ID NO: 12. In a further embodiment, the antibody, or antigen binding portion thereof, comprises a heavy chain variable region comprising a CDR2 having the amino acid sequence of SEQ ID NO: 111 and a light chain variable region comprising a CDR2 having the amino acid sequence of SEQ ID NO: 11. In another further embodiment, the antibody, or antigen binding portion thereof, comprises a heavy chain variable region comprising a CDR2 having the amino acid sequence of SEQ ID NO: 42 and a light chain variable region comprising a CDR2 having the amino acid sequence of SEQ ID NO: 11. In another embodiment, the antibody, or antigen binding portion thereof, comprises a heavy chain variable region comprising a CDR1 having the amino acid sequence of SEQ ID NO: 6 and a light chain variable region comprising a CDR1 having the amino acid sequence of SEQ ID NO: 21.

In one embodiment, the antibody, or antigen binding portion thereof, is an IgG isotype. In a further related embodiment, the antibody, or antigen binding portion thereof, is an IgG1 or an IgG4 isotype.

In one embodiment, the antibody, or antigen binding portion thereof, has an IC50 of at least 50 nM in a Jurkat cell reporter assay.

In another aspect, the present invention features an antagonist anti-CD40 antibody, or antigen-binding portion thereof, comprising a light chain variable region comprising a CDR3 having an amino acid sequence as set forth in SEQ ID NO: 12 and/or a heavy chain variable region comprising a CDR3 having an amino acid sequence as set forth in SEQ ID NO: 8. In one embodiment, the light chain variable region of the antagonistic anti-CD40 antibody, or antigen-binding portion thereof, comprises a CDR3 having the amino acid sequence as set forth in SEQ ID NO: 12 and wherein the heavy chain variable region comprises a CDR3 having the amino acid sequence as set forth in SEQ ID NO: 8. In another embodiment, the heavy chain variable region of the antagonist anti-CD40 antibody, or antigen-binding portion thereof, further comprises a CDR2 having an amino acid sequence as set forth in SEQ ID NO: 42. In another further embodiment, the light chain variable region of the antagonist anti-CD40 antibody, or antigen-binding portion thereof, further comprises a CDR2 having an amino acid sequence set forth in SEQ ID NO: 11. In another embodiment, the heavy chain variable region of the antagonist anti-CD40 antibody, or antigen-binding portion thereof, further comprises a CDR1 having an amino acid sequence as set forth in SEQ ID NO:6. In another further embodiment, the light chain variable region of the antagonist anti-CD40 antibody, or antigen-binding portion thereof, further comprises a CDR1 having an amino acid sequence as set forth in SEQ ID NO: 21.

In another embodiment, the antagonistic anti-CD40 antibody, or antigen-binding portion thereof, comprises a heavy chain variable region comprising a CDR set of SEQ ID NOs: 6, 42, and 8, and a light chain variable region comprising a CDR set of SEQ ID NOs: 21, 11, and 12.

In one embodiment, the antagonist anti-CD40 antibody, or antigen binding portion thereof, is humanized. In a further embodiment, the antagonist anti-CD40 antibody, or antigen binding portion thereof, further comprises a human acceptor framework. In a further related embodiment, the human acceptor framework comprises an amino acid sequence selected from SEQ ID NOs: 82-106. In another embodiment, the human acceptor framework comprises at least one framework region amino acid substitution, wherein the amino acid sequence of the framework is at least 65% identical to the sequence of said human acceptor framework and comprises at least 70 amino acid residues identical to said human acceptor framework. In a further embodiment, the human acceptor framework comprises at least one framework region amino acid substitution at a key residue, said key residue selected from:
  a residue adjacent to a CDR;
  a glycosylation site residue;
  a rare residue;
  a residue capable of interacting with human CD40;
  a residue capable of interacting with a CDR;
  a canonical residue;
  a contact residue between heavy chain variable region and light chain variable region;
  a residue within a Vernier zone; and
  a residue in a region that overlaps between a Chothia-defined variable heavy chain CDR1 and a Kabat-defined first heavy chain framework.

In a further related embodiment, the key residue is selected from 48H, 49H, and 36L. In one embodiment, the key residue substitution is in the variable heavy chain region and is V48I or S49A. In another embodiment, the key residue substitution is in the variable light chain region and is Y36F.

In one embodiment, the antagonist anti-CD40 antibody, or antigen binding portion thereof, comprises a heavy chain variable region comprising the amino acid sequence set forth in SEQ ID NO: 28. In another embodiment, the antagonist anti-CD40 antibody, or antigen binding portion thereof, comprises a light chain variable region comprising the amino acid sequence set forth in SEQ ID NO: 20.

In one embodiment, the antagonist anti-CD40 antibody, or antigen binding portion thereof, is substantially free of agonist activity. In another embodiment, the antagonist anti-CD40 antibody, or antigen-binding portion thereof, inhibits the binding of CD40 to CD40 ligand (CD40L) or to soluble CD40 ligand (sCD40L). In another further embodiment, the antagonist anti-CD40 antibody, or antigen-binding portion thereof, binds cyno CD40. In one embodiment, the anti-CD40 antibody, or antigen-binding portion thereof, binds human and cyno CD40, but does not bind rat, rabbit, or mouse CD40.

In another embodiment, the antagonist anti-CD40 antibody, or antigen-binding portion thereof, is capable of modulating a biological function of CD40. In a further embodiment, the antagonist anti-CD40 antibody, or antigen-binding portion thereof, is capable of neutralizing CD40. In still another further embodiment, the antagonist anti-CD40 antibody, or antigen-binding portion thereof, inhibits NF-κB activation.

In one embodiment, the antagonist anti-CD40 antibody, or antigen-binding portion thereof, has an on rate constant ($K_{on}$) to CD40 selected from at least about $10^2$ $M^{-1}s^{-1}$; at least about $10^3$ $M^{-1}s^{-1}$; at least about $10^4$ $M^{-1}s^{-1}$; at least about $10^5$ $M^{-1}s^{-1}$; and at least about $10^6$ $M^{-1}s^{-1}$; as measured by surface plasmon resonance.

In another embodiment, the antagonist anti-CD40 antibody, or antigen-binding portion thereof, has a dissociation constant ($K_D$) to CD40 selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

In another embodiment, the antagonist anti-CD40 antibody, or antigen-binding portion thereof, comprises a heavy chain immunoglobulin constant domain of a human IgM constant domain, a human IgG1 constant domain, a human IgG2 constant domain, a human IgG3 constant domain, a human IgG4 constant domain, a human IgA constant domain, or a human IgE constant domain. In a related embodiment, the heavy chain immunoglobulin constant region domain of the antagonist anti-CD40 antibody, or antigen-binding portion thereof, is a human IgG1 constant domain. In a further related embodiment, the human IgG1 constant domain of the antagonist anti-CD40 antibody, or antigen-binding portion thereof, comprises an amino acid sequence of SEQ ID NO:2 or SEQ ID NO:3.

In another embodiment, the antagonist anti-CD40 antibody, or antigen-binding portion thereof, further comprises a light chain immunoglobulin constant domain comprising a human Ig kappa constant domain or a human Ig lambda constant domain. In a related embodiment, the human Ig kappa constant domain of the antagonist anti-CD40 antibody, or antigen-binding portion thereof, comprises an amino acid sequence of SEQ ID NO:4 or wherein the human Ig lambda constant domain comprises an amino acid sequence SEQ ID NO:81.

The present invention also features, in certain embodiments, an antagonist anti-CD40 antibody, or antigen-binding portion thereof, that competes with the antibody, or antigen binding portion thereof, as set forth in any of the aspects and embodiments described herein.

In another aspect, the present invention features an antagonist anti-CD40 antibody, or antigen-binding portion thereof, that comprises a heavy chain CDR1 comprising an amino acid sequence as set forth in SEQ ID NO:6, a heavy chain CDR2 comprising an amino acid sequence as set forth in SEQ ID NO:42, a heavy chain CDR3 comprising an amino acid sequence as set forth in SEQ ID NO:8, a light chain CDR1 comprising an amino acid sequence as set forth in SEQ ID NO:21, a light chain CDR2 comprising an amino acid sequence as set forth in SEQ ID NO:11, and a light chain CDR3 comprising an amino acid sequence as set forth in SEQ ID NO:12.

In another aspect, the present invention features an antagonist anti-CD40 antibody, or antigen-binding portion thereof, comprising a heavy chain variable domain comprising an amino acid sequence set forth in SEQ ID NO: 28 and a light chain variable domain comprising an amino acid sequence set forth in SEQ ID NO: 20. In another aspect, the present invention features an antagonist anti-CD40 antibody, or antigen-binding portion thereof, comprising a heavy chain variable domain comprising an amino acid sequence having at least 90%, 95%, 96%, 97%, 98%, or 99% identity to SEQ ID NO: 28, and/or a light chain variable domain comprising an amino acid sequence having at least 90%, 95%, 96%, 97%, 98%, or 99% identity to SEQ ID NO: 20.

In another aspect, the present invention features an antagonist anti-CD40 antibody, or antigen-binding portion thereof, comprising a heavy chain comprising an amino acid sequence set forth in SEQ ID NO: 41, or a sequence having at least 90%, 95%, 96%, 97%, 98%, or 99% identity to SEQ ID NO: 41, and/or a light chain comprising an amino acid sequence set forth in SEQ ID NO: 40, or a sequence having at least 90%, 95%, 96%, 97%, 98%, or 99% identity to SEQ ID NO: 40. In one embodiment, the heavy chain of the antagonist anti-CD40 antibody, or antigen binding portion thereof, comprises an amino acid sequence set forth in SEQ ID NO: 41, and the light chain of the antagonistic anti-CD40 antibody, or antigen binding portion thereof, comprises an amino acid sequence set forth in SEQ ID NO: 40.

In another aspect, the present invention features an anti-CD40 antibody comprising a heavy chain comprising an amino acid sequence as set forth in SEQ ID NO: 41, and a light chain comprising an amino acid sequence as set forth in SEQ ID NO: 40.

In one embodiment, the antibodies, or antigen binding portions thereof, of the invention are recombinant.

The present invention also features, in certain embodiments, a pharmaceutical composition comprising the anti-CD40 antibody, or antigen binding portion thereof, as set forth in any of the aspects and embodiments described herein, and a pharmaceutically acceptable carrier.

The present invention also features, in other certain embodiments, a pharmaceutical composition comprising the anti-CD40 antibody, or antigen binding portion thereof, as set forth in any of the aspects and embodiments described herein, and a polysorbate. In a further related embodiment, the polysorbate is polysorbate 80.

In another embodiment, the pharmaceutical composition comprises a histidine buffer.

In another further embodiment, the pharmaceutical composition comprises a polyol. In a related embodiment, the polyol is selected from mannitol, sorbitol, trehalose, or sucrose.

In another embodiment, the pharmaceutical composition has a pH of about 4 to about 8. In a related embodiment, the pharmaceutical composition has a pH of about 5 to about 7.

In another embodiment, the pharmaceutical composition is lyophilized.

The present invention also features, in other embodiments, an isolated nucleic acid encoding an antagonist anti-CD40 antibody amino acid sequence of any one of the aspects and embodiments described herein. In a further embodiment, the present invention features a vector comprising the isolated nucleic acid. In a related embodiment, the vector is selected from pcDNA, pTT, pTT3, pEFBOS, pBV, pJV, and pBJ vectors.

In another embodiment, a host cell comprises the vector. In a related embodiment, the host cell is a prokaryotic cell or a eukaryotic cell. In a further embodiment, the eukaryotic cell is a protist cell, an animal cell, a plant cell, a fungal cell, a yeast cell, a mammalian cell, an avian cell, or an insect cell. In another further embodiment, the mammalian cell is a CHO cell or a COS cell.

The present invention also features, in certain embodiments, a method of producing an antagonist anti-CD40 antibody, or antigen binding portion thereof, the method comprising the steps of culturing a host cell of any one of the aspects and embodiments described herein in culture medium under conditions sufficient to produce the antagonist anti-CD40 antibody, or antigen binding portion thereof. In further embodiments, an antagonist anti-CD40 antibody, or antigen binding portion thereof, is produced by the method.

The present invention also features, in other embodiments, a method for reducing human CD40 activity, the method comprising the step of contacting human CD40 with the antibody, or antigen-binding portion thereof, of any one of the aspects and embodiments described herein, such that human CD40 activity is reduced. In a further embodiment, the method is an in vitro method.

The present invention also features, in other certain embodiments, a method for treating a human subject having a disorder in which CD40 is detrimental comprising administering an effective amount of the anti-CD40 antibody, or antigen binding portion thereof, of any one of the aspects and embodiments described herein, to the subject.

The present invention also features, in other embodiments, a method for reducing human CD40 activity in a human subject having a disorder in which CD40 activity is detrimental, the method comprising the step of administering to the human subject the antibody, or antigen binding portion thereof, of any one of aspects and embodiments described herein, such that human CD40 activity in the human subject is reduced.

In a further embodiment, the antibody, or antigen binding portion thereof, is administered before, concurrently, or after the administration of a second agent to the subject. In a further related embodiment, the second agent is selected from an antibody, or fragment thereof, capable of binding human IL-12; PGE2; LPA; NGF; CGRP; SubP; RAGE; histamine; a histamine receptor blocker; brakykinin; IL-1 alpha; IL-1beta; VEGF; PLGF; methotrexate; a corticosteroid, a glucocorticoid receptor modulator; cyclosporin, rapamycin, FK506, a non-steroidal anti-inflammatory agent, an inhaled steroid; beta-agonist; short-acting or long-acting beta-agonist; antagonist of leukotrienes or leukotriene receptors; ADVAIR; IgE inhibitor; anti-IgE antibodies; XOLAIR; phosphodiesterase inhibitor; PDE4 inhibitor; xanthine; anticholinergic drug; mast cell-stabilizing agent; Cromolyn; IL-4 inhibitor; IL-5 inhibitor; eotaxin/CCR3 inhibitors antagonists of histamine or its receptors including H1, H2, H3, and H4; antagonists of prostaglandin D or its receptors DP1 and CRTH2; TNF antagonist; a soluble fragment of a TNF receptor; ENBREL; TNF enzyme antagonist; TNF converting enzyme (TACE) inhibitor; muscarinic receptor antagonist; TGF-beta antagonist; interferon gamma; perfenidone; chemotherapeutic agent, methotrexate; leflunomide; sirolimus (rapamycin) or an analog thereof, CCI-779; COX2 or cPLA2 inhibitor; NSAID; immunomodulator; p38 inhibitor; TPL-2, MK-2 and NFkB inhibitor; budenoside; epidermal growth factor; corticosteroid; cyclosporine; sulfasalazine; aminosalicylate; 6-mercaptopurine; azathioprine; metronidazole; lipoxygenase inhibitor; mesalamine; olsalazine; balsalazide; antioxidant; thromboxane inhibitor; IL-1 receptor antagonist; anti-IL-1β antibody; anti-IL-6 antibody; growth factor; elastase inhibitor; pyridinyl-imidazole compound; antibody or agonist of LT, IL-1, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibody of CD2, CD3, CD4, CD8, CD25, CD28, CD30, CD40, CD45, CD69, CD90 or their ligand; FK506; rapamycin; mycophenolate mofetil; ibuprofen; prednisolone; phosphodiesterase inhibitor; adenosine agonist; antithrombotic agent; complement inhibitor; adrenergic agent; IRAK, NIK, IKK, p38, or MAP kinase inhibitor; IL-1β converting enzyme inhibitor; TNF-α.quadrature. converting enzyme inhibitor; T-cell signaling inhibitor; metalloproteinase inhibitor; 6-mercaptopurine; angiotensin converting enzyme inhibitor; soluble cytokine receptor; soluble p55 TNF receptor; soluble p75 TNF receptor; sIL-1RI; sIL-1RII; sIL-6R; anti-inflammatory cytokine; IL-4; IL-10; IL-11; or TGF-β.

In a further embodiment, the disorder is selected from a respiratory disorder; asthma; allergic and nonallergic asthma; asthma due to infection; asthma due to infection with respiratory syncytial virus (RSV); chronic obstructive pulmonary disease (COPD); a condition involving airway inflammation; eosinophilia; fibrosis and excess mucus production; cystic fibrosis; pulmonary fibrosis; an atopic disorder; atopic dermatitis; urticaria; eczema; allergic rhinitis; allergic enterogastritis; an inflammatory and/or autoimmune condition of the skin; an inflammatory and/or autoimmune condition of gastrointestinal organs; inflammatory bowel diseases (IBD); ulcerative colitis; Crohn's disease; an inflammatory and/or autoimmune condition of the liver; liver cirrhosis; liver fibrosis; liver fibrosis caused by hepatitis B and/or C virus; scleroderma; tumors or cancers; hepatocellular carcinoma; glioblastoma; lymphoma; Hodgkin's lymphoma; a viral infection; a bacterial infection; a parasitic infection; HTLV-1 infection; suppression of expression of protective type 1 immune responses, and suppression of expression of a protective type 1 immune response during vaccination.

In another further embodiment, the disorder is selected from an autoimmune or inflammatory disease, such as systemic lupus erythematosus (SLE), discoid lupus, lupus nephritis, sarcoidosis, inflammatory arthritis, including, but not limited to, juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, unwanted/unintended immune responses to therapeutic proteins, asthma, Churg-Strauss syndrome (allergic granulomatosis), atopic dermatitis, allergic and irritant contact dermatitis, urticaria, IgE-mediated allergy, atherosclerosis, vasculitis, idiopathic inflammatory myopathies, hemolytic disease, Alzheimer's disease, chronic inflammatory demyelinating polyneuropathy, Sjogren's, and psoriasis.

In one embodiment, an anti-CD40 antibody, or antigen-binding portion thereof, of the invention, e.g. Ab102, is used to treat an inflammatory bowel disease (IBD).

In one embodiment, an anti-CD40 antibody, or antigen-binding portion thereof, of the invention, e.g. Ab102, is used to treat ulcerative colitis.

In one embodiment, an anti-CD40 antibody, or antigen-binding portion thereof, of the invention, e.g. Ab102, is used to treat Crohn's disease.

In one embodiment, an anti-CD40 antibody, or antigen-binding portion thereof, of the invention, e.g. Ab102, is used to treat systemic lupus erythematosus (SLE).

In one embodiment, an anti-CD40 antibody, or antigen-binding portion thereof, of the invention, e.g. Ab102, is used to treat sarcoidosis.

In one embodiment, an anti-CD40 antibody, or antigen-binding portion thereof, of the invention, e.g. Ab102, is used to treat juvenile arthritis.

In one embodiment, an anti-CD40 antibody, or antigen-binding portion thereof, of the invention, e.g. Ab102, is used to treat rheumatoid arthritis.

In one embodiment, an anti-CD40 antibody, or antigen-binding portion thereof, of the invention, e.g. Ab102, is used to treat psoriatic arthritis.

In one embodiment, an anti-CD40 antibody, or antigen-binding portion thereof, of the invention, e.g. Ab102, is used to treat ankylosing spondylitis.

In one embodiment, an anti-CD40 antibody, or antigen-binding portion thereof, of the invention, e.g. Ab102, is used to treat hidradenitis suppurativa.

In one embodiment, an anti-CD40 antibody, or antigen-binding portion thereof, of the invention, e.g. Ab102, is used to treat uveitis.

In one embodiment, an anti-CD40 antibody, or antigen-binding portion thereof, of the invention, e.g. Ab102, is used to treat Sjogren's.

In one embodiment, an anti-CD40 antibody, or antigen-binding portion thereof, of the invention, e.g. Ab102, is used to treat psoriasis.

In another further embodiment, the antibody, or antigen binding fragment thereof, is administered by at least one mode selected from parenteral, subcutaneous, intramuscular, intravenous, intra-articular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

The present invention also features, in other certain embodiments, a method of determining the presence of CD40 or fragment thereof in a test sample by an immunoassay, wherein the immunoassay comprises contacting the test sample with at least one antibody, or antigen-binding portion thereof, of any of the aspects and embodiments described herein, and at least one detectable label. In a further embodiment, the method further comprises the steps of: (i) contacting the test sample with the at least one antibody, or antigen-binding portion thereof, wherein the antibody, or antigen-binding portion thereof, binds to an epitope on the CD40 or fragment thereof so as to form a first complex; (ii) contacting the complex with the at least one detectable label, wherein the detectable label binds to an epitope on the first complex, or on the CD40 or fragment thereof, that is not bound by the antibody, or antigen-binding portion thereof, to form a second complex; and (iii) detecting the presence of the CD40 or fragment thereof in the test sample based on the signal generated by the detectable label in the second complex, wherein the presence of the CD40 or fragment thereof is directly correlated with the signal generated by the detectable label. In a further related embodiment, the method further comprises the steps of: (i) contacting the test sample with the at least one antibody, or antigen-binding portion thereof, wherein the antibody, or antigen-binding portion thereof, binds to an epitope on the CD40 or fragment thereof so as to form a first complex; (ii) contacting the complex with the at least one detectable label, wherein the detectable label competes with the CD40 or fragment thereof for binding to the antibody, or antigen-binding portion thereof, so as to form a second complex; and (iii) detecting the presence of the CD40 or fragment thereof in the test sample based on the signal generated by the detectable label in the second complex, wherein the presence of the CD40 or fragment thereof is indirectly correlated with the signal generated by the detectable label.

In one embodiment, the invention provides a DVD-Ig which comprises the binding regions, e.g. CDRs, described herein. In one embodiment, the DVD-Ig of the invention comprises four polypeptide chains, wherein two polypeptide chains comprise VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, and X2 is an Fc region; and two polypeptide chains comprise VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1; wherein said four polypeptide chains of said binding protein form four functional antigen binding sites. In one embodiment, the first (and/or second) heavy chain of the DVD comprises a CDR set as set forth in SEQ ID NOs: 6, 42, and 8. In one embodiment, the first (and/or second) light chain variable region comprises a CDR set as set forth in SEQ ID NOs: 21, 11, and 12. In one embodiment, the DVD-Ig of the invention is monospecific and binds huCD40. In another embodiment, the DVD-Ig of the invention is multispecific and binds CD40 and a second molecular target.

BRIEF DESCRIPTION OF THE DRAWINGS

FIG. 1B graphically depicts the activity of the same chimeric antibody Ab1 in an agonist assay using the same agonist and antagonist controls as FIG. 1A.

FIGS. 2A and 2B graphically depict agonist activity (FIG. 2A) and antagonist activity (FIG. 2B) of humanized antibody Ab101 in comparison to antibody 4D11, antibody Blb, an IgG antibody (control), and an agonist control antibody (2141).

FIG. 3B graphically depicts B cell survival in the same mouse model administered the same agents as FIG. 3A.

FIG. 4A and FIG. 4B show an amino acid sequence alignment of anti-human CD40 murine antibody antagonists, and the alignment consensus sequences. FIG. 4A shows a sequence alignment of the variable light chains of Antibody 3 (Ab3) (SEQ ID NO:48), Ab1 (SEQ ID NO:9) and Antibody 2 (Ab2) (SEQ ID NO:76) and the variable light chain consensus sequence (SEQ ID NO: 116). FIG. 4B shows a sequence alignment of the variable heavy chains of Ab3 (SEQ ID NO:44), Ab1 (SEQ ID NO:5) and Ab2 (SEQ ID NO:75) and the variable heavy chain consensus sequence (SEQ ID NO: 117).

FIGS. 5A and 5B graphically depict representative neutralization potency (antagonist activity) (FIG. 5A) and agonist activity (FIG. 5B) of Ab102 on human CD40 in the monocyte activation assays described in Example 7. Monocyte activation corresponds with increases in TNF concentration within each assay.

FIG. 10 graphically depicts results showing that Ab102 suppressed anti KLH IgM and anti KLH IgG (dashed line) as compared to control animals treated with vehicle only (solid lines). Cynomolgus monkeys (two/sex/group) were administered Ab102 at dosages of 0 (vehicle only) or 10 mg/kg subcutaneously (SC) for 5 weeks. Keyhole limpet hemocyanin (KLH) was administered to all animals on Day 8. Serum samples were collected from each animal at −11, −7, 0, 4, 7, 10, 14 and 21 days relative to KLH administration (KLH days).

FIG. 12A shows the effect of antibody 138 on glomerular disease in mice dosed with 15 mg/kg of antibody 2×/week, 5 mg/kg of antibody 2×/week, 1.5 mg·kg of antibody 2×/week or 15 mg/kg antibody 1×/week, at day 29 and day 63. Administration of PBS vehicle alone was used as a control. Glomerular disease was assessed on a scale of 0-4. As glomerular disease severity worsened in aging MRL mice, antibody 138 maintained efficacy at minimizing glomerular disease at 5 and 15 mg/kg. Perivascular inflammation was scored on a scale 0-4 based on the following criteria: 0—up to a few rare lymphocytes; 1—a few lymphocytes forming loose aggregates; 2—lymphocytes forming discrete small aggregates; 3—polarized aggregate of lymphocytes that bulge into the lumen of the adjacent vein but fail to fully surround the arcuate artery; 4—lymphocyte aggregate fully surrounding and extending into the adventitia of the arcuate artery.

FIG. 12B depicts results showing the effect of antibody 138 on kidney perivascular (PV) inflammation in mice dosed with 15 mg/kg of antibody 2×/week, 5 mg/kg of antibody 2×/week, 1.5 mg·kg of antibody 2×/week or 15 mg/kg antibody 1×/week, at day 29 and day 63. Administration of PBS vehicle alone was used as a control. Anti-CD40 antibody at 5 and 15 mg/kg was effective at reducing perivascular (PV) infiltrates in the kidney at 29 and 63 days.

FIG. 12C shows the effect of antibody 138 on tubulointerstitial inflammation (TI) in mice dosed with 15 mg/kg of antibody 2×/week, 5 mg/kg of antibody 2×/week, 1.5 mg·kg of antibody 2×/week or 15 mg/kg antibody 1×/week, at day 29 and day 60. Administration of PBS vehicle alone was used as a control. TI was reduced early in disease.

FIG. 13A shows the effect of antibody 138 on salivary gland inflammation in mice dosed with 15 mg/kg of antibody 2×/week, 5 mg/kg of antibody 2×/week, 1.5 mg·kg of antibody 2×/week or 15 mg/kg antibody 1×/week, at day 29 and day 60. Administration of PBS vehicle alone was used as a control. Periductular inflammation was scored on a scale 0-4 based on the following criteria: 0—up to a few rare leukocytes; 1—a few leukocytes forming loose aggregates; 2—leukocytes forming discrete small aggregates; 3—polarized aggregate of leukocytes that fully surround the duct; 4—leukocytes aggregate extending into the glandular parenchyma of the salivary gland.

FIG. 13B shows the effect of antibody 138 on joint inflammation in mice dosed with 15 mg/kg of antibody 2×/week, 5 mg/kg of antibody 2×/week, 1.5 mg·kg of antibody 2×/week or 15 mg/kg antibody 1×/week, at day 29 and day 60. Administration of PBS vehicle alone was used as a control. Joint inflammation was scored for each of two paws per mouse on a scale of 0-4 based on the following criteria: 0—no inflammation; 1—a few leukocytes in joint space; 2—frequent leukocytes within joint space with mild synovial proliferation; 3—leukocytes expanding joint spaces with moderate synovial proliferation; 4—leukocytes and synovial proliferation extending and coalescing within all joint spaces with marked bone erosion and/or proliferation. The scores were added for a total possible score of 8 per mouse.

DETAILED DESCRIPTION OF THE INVENTION

Figure 1A:
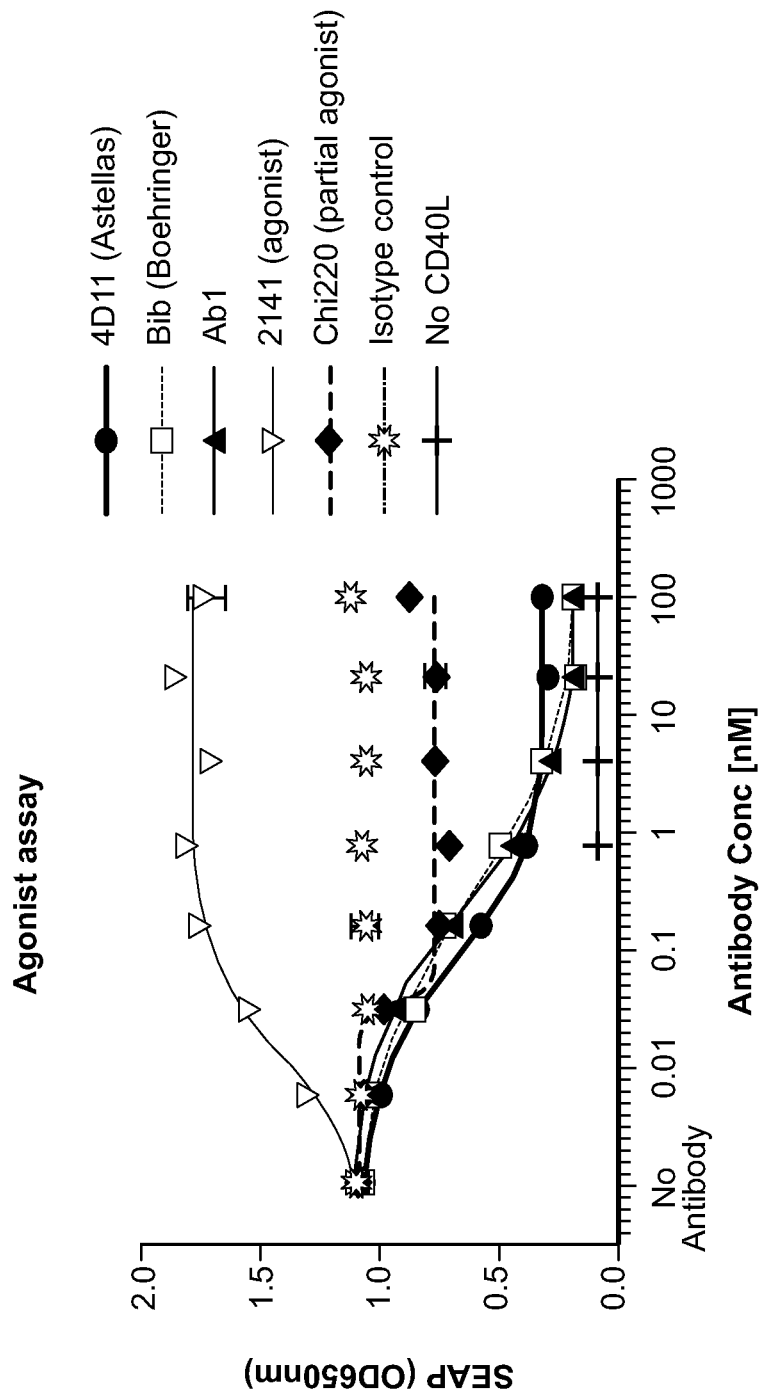
FIG. 1A graphically depicts the antagonistic activity of chimeric antibody (Antibody 1 (Ab1)) versus an agonist control and known antagonist antibodies (4D11 (Astellas) and Bib (Boehringer)).

This invention pertains to antagonist anti-CD40 antibodies, or antigen-binding portions thereof, and uses thereof. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human CD40, to inhibit human CD40/CD40L activity, either in vitro or in vivo; and to prevent or treat diseases or disorders such as chronic inflammatory disease and Crohn's disease, are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. An example of an isolated polypeptide is an isolated antibody, or antigen-binding portion thereof.

The term "recovering" as used herein, refers to the process of rendering a chemical species such as a polypeptide substantially free of naturally associated components by isolation, e.g., using protein purification techniques well known in the art.

The terms "human CD40" and "human CD40 wild type" (abbreviated herein as hCD40, hCD40wt), as used herein, refers to a type I transmembrane protein. In one embodiment, the term human CD40 is intended to include recombinant human CD40 (rhCD40), which can be prepared by standard recombinant expression methods. Table 1 provides the amino acid sequence of human CD40 (i.e., SEQ ID NO. 1), and the extracellular domain thereof (i.e., SEQ ID NO:107), which are known in the art.

TABLE 1

Sequence of human CD40

| Sequence Identifier | Protein | Sequence |
|---|---|---|
| SEQ ID NO.: 1 | Human CD40 | MVRLPLQCVLWGCLLTAVHPEPPTACREKQYLINSQCC SLCQPGQKLVSDCTEFTETECLPCGESEFLDTWNRETH CHQHKYCDPNLGLRVQQKGTSETDTICTCEEGWHCTSE ACESCVLHRSCSPGFGVKQIATGVSDTICEPCPVGFFS NVSSAFEKCHPWTSCETKDLVVQQAGTNKTDVVCGPQD RLRALVVIPIIFGILFAILLVLVFIKKVAKKPTNKAPH PKQEPQEINFPDDLPGSNTAAPVQETLHGCQPVTQEDG KESRISVQERQ |
| SEQ ID NO.: 107 | Human CD40 Extracellular Domain | EPPTACREKQYLINSQCCSLCQPGQKLVSDCTEFTET ECLPCGESEFLDTWNRETHCHQHKYCDPNLGLRVQQK GTSETDTICTCEEGWHCTSEACESCV |

"Biological activity" as used herein, refers to all inherent biological properties of the CD40 receptor. Biological properties of CD40 include but are not limited to binding CD40L; involvement in B cell development; involvement in lymphocyte activation; involvement in antigen presenting cells function; regulating activity of dendritic cells, macrophages and B cells; inducing production of inflammatory cytokines in macrophages and dendritic cells; up-regulating antigen presentation; up-regulating T cell stimulation; and promoting immunoglobulin class switching in B cells.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "agonist", as used herein, refers to a modulator that, when contacted with a molecule of interest, e.g., CD40, causes an increase in the magnitude of a certain activity or function of the molecule compared to the magnitude of the activity or function observed in the absence of the agonist.

The term "antagonist" or "inhibitor", as used herein, refers to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of human CD40 (hCD40). An antagonist antibody of hCD40 may, for example, inhibit CD86 upregulation of primary human B cells that are cultured with (or exposed to) CD40L (such as culturing the B cells with CD40L-expressing human T cells). In one embodiment, an antagonist anti-CD40 antibody, or antigen-binding portion thereof, that is substantially free of agonist activity is defined as having a level of activity that is equivalent to or within one standard deviation from a negative control in an agonist assay, such as the agonist monocyte assay described in Example 7.

The antibody, or antigen binding portion thereof, of the present invention is an antagonist antibody, or antigen binding portion thereof, which causes a decrease in CD40 activity or function as compared to CD40 activity or function in the absence of the antibody, or antigen binding portion thereof. In particular embodiments, the antibody, or antigen binding portion thereof, is substantially free of agonist activity, i.e., the antibody, or antigen binding portion thereof, does not cause an increase in the magnitude of CD40 activity or function as compared to CD40 activity or function in the absence of the antibody, or antigen binding portion thereof. Agonist and antagonist activity can also be assessed using methods known in the art, e.g., using a CD40 expressing reporter cell line expressing human CD40 linked to NFkB mediated alkaline phosphatase (AP) or a B cell assay. Further, in one embodiment, agonist and antagonist activity can be assessed using the in vitro monocyte agonist and antagonist assays described in Example 7.

The term "inhibit binding to CD40L" refers to the ability of the antibody, or antigen binding fragment thereof, to prevent the binding of CD40 to the ligand, CD40L. Such inhibition of binding to CD40L would result in diminishing or abolishing the biological activity mediated by binding of CD40 to CD40L.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen binding portion" or "antigen binding fragment" of an antibody (or simply "antibody portion" or "antibody fragment"), as used herein, refers to one or more fragments of an antibody that retain the ability to specifically bind to an antigen (e.g., hCD40). It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" or "antigen binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" or "antigen binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen-binding portions of the invention linked to a linker polypeptide or an immunoglobulin constant domain. Linker polypeptides comprise two or more amino acid residues joined by peptide bonds and are used to link one or more antigen-binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art and represented in Table 2.

TABLE 2

Sequence of human IgG heavy chain constant domain and light chain constant domain

| Protein | Sequence Identifier | Sequence<br>123456789012345678901234567890012 |
|---|---|---|
| Ig gamma-1 constant region | SEQ ID NO. :2 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPELLGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig gamma-1 constant region mutant | SEQ ID NO. :3 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPEAAGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig Kappa constant region | SEQ ID NO. :4 | TVAAPSVFIFPPSDEQLKSGTASVVCLLNNFY<br>PREAKVQWKVDNALQSGNSQESVTEQDSKDST<br>YSLSSTLTLSKADYEKHKVYACEVTHQGLSSP<br>VTKSFNRGEC |
| Ig Lambda constant region | SEQ ID NO. :81 | QPKAAPSVTLFPPSSEELQANKATLVCLISDF<br>YPGAVTVAWKADSSPVKAGVETTTPSKQSNNK<br>YAASSYLSLTPEQWKSHRSYSCQVTHEGSTVE<br>KTVAPTECS |

Still further, an antibody, or antigen-binding portion thereof, may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hCD40 is substantially free of antibodies that specifically bind antigens other than hCD40). An isolated antibody that specifically binds hCD40 may, however, have cross-reactivity to other antigens, such as CD40 molecules from other species. Moreover, an isolated antibody may be substantially free of other cellular material and/or chemicals.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The terms "Kabat numbering", "Kabat definitions and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen-binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., *J. Mol. Biol.* 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

Heavy Chain Acceptor Sequences

| SEQ ID No. | Protein region | Sequence 1234567890123456789012345678901 2 |
|---|---|---|
| 82 | VH1-18&JH6 FR1 | QVQLVQSGAEVKKPGASVKVSCKASGYTFT |
| 83 | VH1-18&JH6 FR2 | WVRQAPGQGLEWMG |
| 84 | VH1-18&JH6 FR3 | RVTMTTDTSTSTAYMELRSLRSDDTAVYYCAR |
| 85 | VH1-18&JH6 FR4 | WGQGTTVTVSS |
| 82 | 21/28&JH4 FR1 | QVQLVQSGAEVKKPGASVKVSCKASGYTFT |
| 86 | 21/28&JH4 FR2 | WVRQAPGQRLEWMG |
| 87 | 21/28&JH4 FR3 | RVTITRDTSASTAYMELSSLRSEDTAVYYCAR |
| 88 | 21/28&JH4 FR4 | WGQGTLVTVSS |
| 89 | VH2-26&JH6 FR1 | QVTLKESGPVLVKPTETLTLTCTVSGFSLS |
| 90 | VH2-26&JH6 FR2 | WIRQPPGKALEWLAH |
| 91 | VH2-26&JH6 FR3 | RLTISKDTSKSQVVLTMTNMDPVDTATYYCAR |
| 85 | VH2-26&JH6 FR4 | WGQGTTVTVSS |
| 92 | M60&JH4 FR1 | QVTLRESGPALVKPTQTLTLTCTLYGFSLS |
| 93 | M60&JH4 FR2 | WIRQPPGKALEWLA |
| 94 | M60&JH4 FR3 | RLTISKDTSKNQVVLTMTNMDPVDTATYYCAR |
| 88 | M60&JH4 FR4 | WGQGTLVTVSS |
| 82 | VH1-46&JH6 FR1 | QVQLVQSGAEVKKPGASVKVSCKASGYTFT |
| 83 | VH1-46&JH6 FR2 | WVRQAPGQGLEWMG |
| 95 | VH1-46&JH6 FR3 | RVTMTRDTSTSTVYMELSSLRSEDTAVYYCAR |
| 85 | VH1-46&JH6 FR4 | WGQGTTVTVSS |

TABLE 4

Light Chain Acceptor Sequences

| SEQ ID No. | Protein region | Sequence 1234567890123456789012345678901 2 |
|---|---|---|
| 96 | A20&JK4 FR1 | DIQMTQSPSSLSASVGDRVTITC |
| 97 | A20&JK4 FR2 | WYQQKPGKVPKLLIY |
| 98 | A20&JK4 FR3 | GVPSRFSGSGSGTDFTLTISSLQPEDVATYYC |
| 99 | A20&JK4 FR4 | FGGGTKVEIKR |
| 96 | III-3R&JK4 FR1 | DIQMTQSPSSLSASVGDRVTITC |
| 114 | III-3R&JK4 FR2 | WYQQKPGKAPKLLIY |
| 100 | III-3R&JK4 FR3 | GVPSRISGSGSGTDFTFTISSLQPEDIATYYC |
| 99 | III-3R&JK4 FR4 | FGGGTKVEIKR |
| 101 | A1&JK4 FR1 | DVVMTQSPLSLPVTLGQPASISC |
| 102 | A1&JK4 FR2 | WFQQRPGQSPRRLIY |
| 103 | A1&JK4 FR3 | GVPDRFSGSGSGTDFTLKISRVEAEDVGVYYC |
| 99 | A1&JK4 FR4 | FGGGTKVEIKR |
| 104 | O1&JK2 FR1 | DIVMTQTPLSLPVTPGEPASISC |
| 105 | O1&JK2 FR2 | WYLQKPGQSPQLLIY |
| 103 | O1&JK2 FR3 | GVPDRFSGSGSGTDFTLKISRVEAEDVGVYYC |
| 106 | O1&JK2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest (e.g., human CD40), and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets.

The term "dual variable domain" or "DVD" or "DVD-Ig" as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein (e.g., SEQ ID NOs:6, 42, and 8 (heavy chain) and 21, 11, and 12 (light chain)) are used in an anti-CD40 DVD. Examples of DVD-Ig structures are known in the art and are described, for example, in U.S. Pat. No. 7,612,181, which is incorporated by reference herein.

As used herein, the term "neutralizing" refers to neutralization of biological activity of a cytokine receptor when an antibody, or antigen binding portion thereof, specifically binds the cytokine receptor. Preferably, a neutralizing antibody, or antigen binding portion thereof, is a neutralizing antibody whose binding to hCD40 results in inhibition of a biological activity of hCD40. Preferably the neutralizing antibody, or antigen binding portion thereof, binds hCD40 and reduces a biologically activity of hCD40 by at least about 20%, 40%, 60%, 80%, 85% or more. Inhibition of a biological activity of hCD40 by a neutralizing antibody, or antigen binding portion thereof, can be assessed by measuring one or more indicators of hCD40 biological activity well known in the art.

The term "activity" includes activities such as the binding specificity/affinity of an antibody for an antigen, for example, an anti-hCD40 antibody that binds to an hCD40 antigen and/or the neutralizing potency of an antibody, for example, an anti-hCD40 antibody whose binding to hCD40 inhibits the biological activity of hCD40, e.g., binding CD40L; involvement in B cell development; involvement in lymphocyte activation; involvement in antigen presenting cells function; regulating activity of dendritic cells, macrophages and B cells; inducing production of inflammatory cytokines in macrophages and dendritic cells; up-regulating antigen presentation; up-regulating T cell stimulation; and promoting immunoglobulin class switching in B cells.

Exemplary assays for assessing the activity of the anti-CD40 antibodies of the present invention include in vitro an in vivo assays as set forth herein. Specifically, the assays may be used to determine whether an anti-CD40 antibody is an agonist or an antagonist antibody.

For example, binding to human CD40 and inhibition of CD40-CD40L interaction can be assayed using a human CD40-expressing cell line via FACS analyses. Antagonist and agonist activities can be assessed using a CD40-expressing reporter cell line expressing human CD40 linked to NFkB mediated alkaline phosphatase (AP). When signal is received through CD40, NFkB activation leads to secretion of AP which is measured by colorimetric substrate. As an exemplary antagonist assay, a CD40 reporter line can be cultured with either Jurkat cell line expressing CD40L (to provide physiological ligand interaction) or with soluble CD40L and the ability of anti-CD40 antibodies to block the NFkB signal can be assessed. As an exemplary agonist assay, a human CD40 reporter cell line can be treated with anti-CD40 antibodies and the NFkB signal measured as described above.

Alternatively, a B cell agonist assay can be utilized in which B cells are activated with low dose anti-IgM and IL4, prior to addition of a CD40 antagonist antibody. Enhancement of B cell activation can be measured as upregulation of CD86, which in turn is indicative of agonist activity. Similarly, a B cell antagonist assay can be utilized in which primary human B cells are cultured with CD40L-expressing human T cell line that leads to B cell activation and upregulation of CD86 expression via CD40/CD40L interaction Inhibition of CD86 upregulation of primary human B cells is indicative of antagonist activity.

The term "epitope" includes any polypeptide determinant capable of specific binding to a an antibody or antigen-binding portion thereof. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In various embodiments, an epitope may be a linear or sequential epitope, i.e., a linear sequence of amino acids, of the primary structure of the antigen, i.e., CD40. Alternatively, in other embodiments, an epitope may be a conformational epitope having a specific three-dimensional shape when the antigen assumes its secondary structure. For example, the conformational epitope may comprise non-linear, i.e., non-sequential, amino acids of the antigen.

In a particular embodiment, an epitope is a region of an antigen that is bound by an antibody or antigen-binding portion thereof. In certain embodiments, an antibody or antigen-binding portion thereof is said to specifically bind an antigen when it preferentially recognizes its target antigen in a complex mixture of proteins and/or macromolecules.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today*

21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human CD40 which can be generated using techniques well known in the art, such as, but not limited to, using human Ig phage libraries such as those disclosed in Jermutus et al., PCT publication No. WO 2005/007699 A2.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The term "labeled antibody" as used herein, refers to an antibody with a label incorporated that provides for the identification of the antibody, or antigen binding portion thereof. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The terms "crystal", and "crystallized" as used herein, refer to an antibody, or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as used herein refers to a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162 incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of hCD40). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hCD40). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

As used herein, the term "non-responder" is used to refer to a subject having IBD (e.g., Crohn's disease or ulcerative colitis) who has no, or limited or inadequate, improvement in their clinical disease status following treatment with a TNFα inhibitor (e.g., lack of reduction in CDAI score, lack of reduction in use of corticosteroids). In one embodiment, a TNF non-responder is a subject having IBD who fails to achieve a reduction of 100 points or more in their Crohn's Disease Activity Index (CDAI) score following treatment with a TNFα inhibitor. In one embodiment, a non-responder is a subject having IBD who fails to achieve a reduction of 100 points or more in their Crohn's Disease Activity Index (CDAI) score in a specific time frame following treatment with a TNFα inhibitor.

I. Antibodies that Bind Human CD40 (hCD40)

One aspect of the present invention provides antagonistic humanized antibodies, or antigen-binding portions thereof, that bind CD40, including human CD40 (hCD40). Other embodiments of the invention include murine monoclonal antibodies, or antigen-binding portions thereof, that bind to CD40, as well as chimeric antibodies comprising the variable regions of the anti-CD40 murine antibodies described herein. Preferably, the antibodies of the invention are antagonistic anti-CD40 (e.g., anti-human CD40) antibodies having no significant agonist activity.

1. Humanized Anti-hCD40 Antagonist Antibodies Derived from Antibody 1 (Ab1)

The invention is based, at least in part, on the identification of humanized anti-CD40 antibodies having antagonistic characteristics and, in certain embodiments, having no substantial agonist activity.

As described in Example 1, three antagonist anti-hCD40 murine antibodies were identified, i.e., Ab1 (VL sequence described in SEQ ID NO: 9 and VH sequence described in SEQ ID NO: 5), Ab2 (VL sequence described in SEQ ID NO: 76 and VH sequence described in SEQ ID NO: 75), and Ab3 (VL sequence described in SEQ ID NO: 48 and VH sequence described in SEQ ID NO: 44).

Consensus CDR sequences were determined based on alignments of the CDR amino acid sequences of murine antagonist antibodies Ab1, Ab2, and Ab3. Consensus amino acid sequences for the VH CDR1, CDR2, and CDR3 regions are described in SEQ ID NOs 78, 79 and 80, respectively, and consensus amino acid sequences for the VL CDR1, CDR2, and CDR3 amino acid sequences are described in SEQ ID NOs 108, 109 and 110, respectively. All sequences are also described below in Table 5 and in FIG. 4.

TABLE 5

Anti-CD40 Hybridoma CDR Amino Acid Sequence Alignments

| | Hybridoma | CDR1 | CDR2 | CDR3 |
|---|---|---|---|---|
| Heavy chain (SEQ ID NOS 45-47, 6-8, 6, 42, 8 and 78-80, respectively, in order of appearance) | Ab3<br>Ab1<br>Ab2<br>Consensus | GYTFTSYTMH<br>GFTFSDYGMN<br>GFTFSDYGMN<br>GFTFSDYGMN<br>Y  TS T H | YINPSSDYPNYNQKFKD<br>YISSGRSNIYYADTVKG<br>YISSGRGNIYYADTVKG<br>YISSGR NIYYADTVKG<br> NPSS YPN NQKF D | WGYSFDY<br>SWGYFDV<br>SWGYFDV<br>SWGYFDV<br>WGYS |
| Light chain (SEQ ID NOS 49-51, 10-12, 10-12 and 108-110, respectively, in order of appearance) | Ab3<br>Ab1<br>Ab2<br>Consensus | RSSKSLLHS-NGNTYLY<br>KSSQSLLNSGNQKNYLT<br>KSSQSLLNSGNQKNYLT<br>KSSQSLLNSGNQKNYLT<br>R  K   H - GNT Y | RMSTLAS<br>WASTRES<br>WASTRES<br>WASTRES<br>RM  LA | MQHLEYPLT<br>QNDYTYPLT<br>QNDYTYPLT<br>QNDYTYPLT<br>MQHLE |

The consensus amino acid sequence of the heavy chain CDR1 domain is set forth as SEQ ID NO:78 (G(F/Y)TF(S/T)(D/S)Y(G/T)M(N/H)). The consensus amino acid sequence of the variable heavy chain CDR2 domain is set forth as SEQ ID NO:79 (YI(S/N)(S/P)(G/S)(R/S) (D/S/G)(N/Y)(I/P) (Y/N)Y(A/N)(D/Q)(T/K) (V/F)K(G/D)). The consensus amino acid sequence of the variable heavy chain CDR3 domain is set forth in SEQ ID NO:80 ((S/W)(W/G)(G/Y)(Y/S)FDV).

The consensus amino acid sequence of the variable light chain CDR1 domain is set forth as SEQ ID NO:108 ((K/R)SS(Q/K)SLL(N/H)S(G/-)N(Q/G) (K/N)(N/T)YL(T/Y)). The consensus amino acid sequence of the variable light chain CDR2 domain is set for as SEQ ID NO:109 ((W/R)(A/M) ST (R/L) (E/A)S). The consensus amino acid sequence of the variable light chain CDR3 domain is set forth as SEQ ID NO:110 ((Q/M)(N/Q) (D/H)(Y/L)(T/E)YPLT).

In one embodiment, the invention provides an anti-CD40 antagonist antibody, or antigen-binding portion thereof, comprising a variable light chain comprising a CDR1 having the amino acid sequence of SEQ ID NO: 108, a CDR2 having the amino acid sequence of SEQ ID NO: 109, a CDR3 having the amino acid sequence of SEQ ID NO: 110, and comprising a variable heavy chain comprising a CDR1 having the amino acid sequence of SEQ ID NO: 78, a CDR2 having the amino acid sequence of SEQ ID NO: 79, a CDR3 having the amino acid sequence of SEQ ID NO: 80.

Following the identification of murine antibodies Ab1, Ab2, and Ab3, antibodies Ab1 and Ab3 were selected for humanization (described below in Example 2). Tables 11 and 12 provide the amino acid sequences of CDR, VH, and VL regions of humanized Ab1 and Ab3, respectively. Specifically, nine different humanized antibodies were created based on Ab3 (see Example 2 and Table 12 below). Four different humanized antibodies based on Ab1 were also created, including the following:

A) huAb1VH.1/VL.1 (VH amino acid sequence set forth as SEQ ID NO: 13 and VH CDR1, CDR2, and CDR3 sequences set forth as SEQ ID NOs: 6, 7, and 8, respectively; and VL amino acid sequence set forth as SEQ ID NO: 14 and VL CDR1, CDR2, and CDR3 sequences set forth as SEQ ID NOs: 10, 11, and 12, respectively);

B) huAb1VH.1A/VL.1 (VH amino acid sequence set forth as SEQ ID NO: 15 and VH CDR1, CDR2, and CDR3 sequences set forth as SEQ ID NOs: 6, 7, and 8, respectively; and VL amino acid sequence set forth as SEQ ID NO: 14 and VL CDR1, CDR2, and CDR3 sequences set forth as SEQ ID NOs: 10, 11, and 12, respectively);

C) huAb1VH.1/VL.1A (VH amino acid sequence set forth as SEQ ID NO: 13 and VH CDR1, CDR2, and CDR3 sequences set forth as SEQ ID NOs: 6, 7, and 8, respectively; and VL amino acid sequence set forth as SEQ ID NO: 16 and VL CDR1, CDR2, and CDR3 sequences set forth as SEQ ID NOs: 10, 11, and 12, respectively); and D) huAb1VH.1A/VL.1A (VH amino acid sequence set forth as SEQ ID NO: 15 and VH CDR1, CDR2, and CDR3 sequences set forth as SEQ ID NOs: 6, 7, and 8, respectively; VL amino acid sequence set forth as SEQ ID NO: 16 and VL CDR1, CDR2, and CDR3 sequences set forth as SEQ ID NOs: 10, 11, and 12, respectively).

Humanized versions of Ab1 were further modified in order to remove a potential deamidation site in the light chain CDR1. Six variant huAb1 antibodies were analyzed, and four of the antibodies were identified as being antagonists of CD40. The six antibodies are referred to herein as Ab1v1, Ab1v2, Ab1v3, Ab1v4, Ab1v5, and Ab1v6 (CDR and variable sequences are provided in Table 13 below). Of the six humanized Ab1 variants, huAb1v1 was selected as having particularly superior antagonist activity. The heavy chain variable sequence of huAb1v1 is provided in SEQ ID NO: 15 with CDR1, CDR2, and CDR3 sequences described in SEQ ID NOs: 6, 7, and 8, respectively. The light chain variable sequence of huAb1v1 is provided in SEQ ID NO: 20 with CDR1, CDR2, and CDR3 sequences described in SEQ ID NOs: 21, 11, and 12, respectively), the variable regions were cloned into two different IgG backgrounds resulting in two anti-CD40 antagonist antibodies, i.e., Ab101 and Ab102. Table 6 (and Table 19) provides full length heavy chain and light chain sequences for particular embodiments of the present invention relating to these IgG antibodies. In Table 16, constant regions are underlined and CDR domains are in bold.

TABLE 6

Humanized Anti-CD40 Antibodies Ab101 and Ab102 and Heavy and Light Chain Sequences Thereof

| Ab | Heavy Chain Sequence | HC SEQ ID NO: | Light Chain Sequence | LC SEQ ID NO: |
|---|---|---|---|---|
| Ab101 | EVQLVESGGGLVKPGGSLRLSCAASGFTF SDYGMNWVRQAPGKGLEWIAYISSGRGNI YYADTVKGRFTISRDNAKNSLYLQMNSLR AEDTAVYYCARSWGYFDVWGQGTTVTVSS ASTKGPSVFPLAPSSKSTSGGTAALGCLV KDYFPEPVTVSWNSGALTSGVHTFPAVLQ SSSGLYSLSSVVTVPSSSLGTQTYICNVNH KPSNTKVDKKVEPKSCDKTHTCPPCPAPE AAGGPSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSREEMTKNQVSLTCLVKGFYPSDIA VEWESNGQPENNYKTTPPVLDSDGSFFLY SKLTVDKSRWQQGNVFSCSVMHEALHNHY TQKSLSLSPGK | 39 | DIVMTQSPDSLAVSLGERATINCKSSQSL LNRGNQKNYLTWFQQKPGQPPKLLIYWAS TRESGVPDRFSGSGSGTDFTLTISSLQAE DVAVYYCQNDYTYPLTFGQGTKLEIKRTV AAPSVFIFPPSDEQLKSGTASVVCLLNNF YPREAKVQWKVDNALQSGNSQESVTEQDS KDSTYSLSSTLTLSKADYEKHKVYACEVT HQGLSSPVTKSFNRGEC | 40 |
| Ab102 | EVQLVESGGGLVKPGGSLRLSCAASGFTF SDYGMNWVRQAPGKGLEWIAYISSGRGNI YYADTVKGRFTISRDNAKNSLYLQMNSLR AEDTAVYYCARSWGYFDVWGQGTTVTVSS ASTKGPSVFPLAPSSKSTSGGTAALGCLV KDYFPEPVTVSWNSGALTSGVHTFPAVLQ SSSGLYSLSSVVTVPSSSLGTQTYICNVNH KPSNTKVDKKVEPKSCDKTHTCPPCPAPE AAGGPSVFLFPPKPKDQLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSREEMTKNQVSLTCLVKGFYPSDIA VEWESNGQPENNYKTTPPVLDSDGSFFLY SKLTVDKSRWQQGNVFSCSVLHEALHNHY TQKSLSLSPGK | 41 | DIVMTQSPDSLAVSLGERATINCKSSQSL LNRGNQKNYLTWFQQKPGQPPKLLIYWAS TRESGVPDRFSGSGSGTDFTLTISSLQAE DVAVYYCQNDYTYPLTFGQGTKLEIKRTV AAPSVFIFPPSDEQLKSGTASVVCLLNNF YPREAKVQWKVDNALQSGNSQESVTEQDS KDSTYSLSSTLTLSKADYEKHKVYACEVT HQGLSSPVTKSFNRGEC | 40 |

The heavy chain CDR2 of antibody huAb1v1 was further mutagenized resulting in seventeen variants (described below in Example 4). These huAb1v1 heavy chain CDR2 variants are referred to herein as huAb1v1CDR2v1 to huAb1v1CDR2v17. The sequences of the huAb1v1CDR2v1 to huAb1v1CDR2v17 heavy chains are provided in Table 16, where VH huAb1v1CDR2v7 was selected as the clone having particularly superior antagonistic activity against CD40, while remaining relatively free of agonist activity. The heavy chain variable sequence of huAb1v1CDR2v7 is provided in SEQ ID NO: 28 with CDR1, CDR2, and CDR3 sequences described in SEQ ID NOs: 6, 42, and 8, respectively.

Following the selection of the huAb1v1CDR2v7 VH (VH of SEQ ID NO: 28 with CDR1, CDR2, and CDR3 sequences described in SEQ ID NOs: 6, 42, and 8, respectively) and the huAb1v1 VL (VL of SEQ ID NO: 20 with CDR1, CDR2, and CDR3 sequences described in SEQ ID NOs: 21, 11, and 12, respectively), the variable regions were cloned into two different IgG backgrounds resulting in two anti-CD40 antagonist antibodies, i.e., Ab101 and Ab102. Table 6 (and Table 19) provides full length heavy chain and light chain sequences for particular embodiments of the present invention relating to these IgG antibodies. In Table 16, constant regions are underlined and CDR domains are in bold.

Accordingly, in one embodiment, the present invention is directed to an antagonist anti-CD40 antibody comprising a light chain having the amino acid sequence as set forth in SEQ ID NO:40 and a heavy chain having the amino acid sequence as set forth in SEQ ID NO: NO:39 (Ab101). In an alternative embodiment, the present invention is directed to an antagonist anti-CD40 antibody comprising a light chain having the amino acid sequence as set forth in SEQ ID NO:40 and a heavy chain having the amino acid sequence as set forth in SEQ ID NO: NO:41 (Ab102).

Thus, the invention includes murine, chimeric, and humanized anti-CD40 antibodies having antagonist activity. In certain embodiments, the present invention provides an antagonistic anti-CD40 antibody, or antigen binding portion thereof, including a light chain variable region having a CDR3 having an amino acid sequence as set forth in SEQ ID NO: 12 and/or a heavy chain variable region having a CDR3 having an amino acid sequence as set forth in SEQ ID NO: 8. In a particular embodiment, the antagonist anti-CD40 antibody, or antigen-binding portion thereof, includes a heavy chain CDR1 having an amino acid sequence as set forth in SEQ ID NO:6, a heavy chain CDR2 having an amino acid sequence as set forth in SEQ ID NO:42, a heavy chain CDR3 having an amino acid sequence as set forth in SEQ ID NO:8, a light chain CDR1 having an amino acid sequence as set forth in SEQ ID NO:21, a light chain CDR2 having an amino acid sequence as set forth in SEQ ID NO:11, and a light chain CDR3 having an amino acid sequence as set forth in SEQ ID NO:12. In a particular embodiment, the antagonist anti-CD40 antibody, or antigen-binding portion thereof, includes a heavy chain variable domain having an amino acid sequence set forth in SEQ ID NO: 28 and a light chain variable domain having an amino acid sequence set forth in SEQ ID NO: 20. In one embodiment, the antagonist anti-CD40 antibody, or antigen-binding portion thereof, includes a heavy chain having an amino acid sequence set forth in SEQ ID NO: 41; and a light chain comprising an amino acid sequence set forth in SEQ ID NO: 40. In another embodiment, the antagonist anti-CD40 antibody, or antigen-binding portion thereof, includes a heavy chain having an amino acid sequence set forth in SEQ ID NO: 39; and a light chain comprising an amino acid sequence set forth in SEQ ID NO: 40.

Antibodies having the amino acid sequences (variable or CDR) described in Tables 5, 6, 11, 12, 13, 14, 16, 17, 18, and 19 are included in the invention. Accordingly, in one aspect, the present invention is directed to an antagonist anti-CD40 antibody, or antigen-binding portion thereof, having a light chain variable region comprising (a) a CDR1 having an amino acid sequence as set forth in SEQ ID NO: 10, 17, 19, or 21; (b) a CDR2 having an amino acid sequence as set forth in SEQ ID NO: 11; and (c) a CDR3 having an amino acid sequence set forth in SEQ ID NO: 12. Alternatively or in combination, the antagonist anti-CD40 antibody, or antigen-binding portion thereof, includes a heavy chain variable region comprising (a) a CDR1 having an amino acid sequence as set forth in SEQ ID NO: 6; (b) a CDR2 having an amino acid sequence as set forth in SEQ ID NO: 7 or 42; and (c) a CDR3 having an amino acid sequence set forth in SEQ ID NO: 8.

In a particular embodiment, the antagonist anti-CD40 antibody, or antigen-binding portion thereof, has a light chain variable region comprising (a) a CDR1 having an amino acid sequence as set forth in SEQ ID NO: 10; (b) a CDR2 having an amino acid sequence as set forth in SEQ ID NO: 11; and (c) a CDR3 having an amino acid sequence set forth in SEQ ID NO: 12; and a heavy chain variable region comprising (a) a CDR1 having an amino acid sequence as set forth in SEQ ID NO: 6; (b) a CDR2 having an amino acid sequence as set forth in SEQ ID NO: 7; and (c) a CDR3 having an amino acid sequence set forth in SEQ ID NO: 8.

In another embodiment, the antagonist anti-CD40 antibody, or antigen-binding portion thereof, has a light chain variable region comprising (a) a CDR1 having an amino acid sequence as set forth in SEQ ID NO: 19; (b) a CDR2 having an amino acid sequence as set forth in SEQ ID NO: 11; and (c) a CDR3 having an amino acid sequence set forth in SEQ ID NO: 12; and a heavy chain variable region comprising (a) a CDR1 having an amino acid sequence as set forth in SEQ ID NO: 6; (b) a CDR2 having an amino acid sequence as set forth in SEQ ID NO: 7; and (c) a CDR3 having an amino acid sequence set forth in SEQ ID NO: 8.

In another embodiment, the antagonist anti-CD40 antibody, or antigen-binding portion thereof, has a light chain variable region comprising (a) a CDR1 having an amino acid sequence as set forth in SEQ ID NO: 17; (b) a CDR2 having an amino acid sequence as set forth in SEQ ID NO: 11; and (c) a CDR3 having an amino acid sequence set forth in SEQ ID NO: 12; and a heavy chain variable region comprising (a) a CDR1 having an amino acid sequence as set forth in SEQ ID NO: 6; (b) a CDR2 having an amino acid sequence as set forth in SEQ ID NO: 7; and (c) a CDR3 having an amino acid sequence set forth in SEQ ID NO: 8.

In another embodiment, the antagonist anti-CD40 antibody, or antigen-binding portion thereof, has a light chain variable region comprising (a) a CDR1 having an amino acid sequence as set forth in SEQ ID NO: 21; (b) a CDR2 having an amino acid sequence as set forth in SEQ ID NO: 11; and (c) a CDR3 having an amino acid sequence set forth in SEQ ID NO: 12; and a heavy chain variable region comprising (a) a CDR1 having an amino acid sequence as set forth in SEQ ID NO: 6; (b) a CDR2 having an amino acid sequence as set forth in SEQ ID NO: 7; and (c) a CDR3 having an amino acid sequence set forth in SEQ ID NO: 8.

In another embodiment, the antagonist anti-CD40 antibody, or antigen-binding portion thereof, has a light chain variable region comprising (a) a CDR1 having an amino acid sequence as set forth in SEQ ID NO: 21; (b) a CDR2 having an amino acid sequence as set forth in SEQ ID NO: 11; and (c) a CDR3 having an amino acid sequence set forth in SEQ ID NO: 12; and a heavy chain variable region comprising (a) a CDR1 having an amino acid sequence as set forth in SEQ ID NO: 6; (b) a CDR2 having an amino acid sequence as set forth in SEQ ID NO: 42; and (c) a CDR3 having an amino acid sequence set forth in SEQ ID NO: 8.

In another embodiment, the antagonist anti-CD40 antibody, or antigen-binding portion thereof, has a light chain variable region comprising (a) a CDR1 having an amino acid sequence as set forth in SEQ ID NO: 108; (b) a CDR2 having an amino acid sequence as set forth in SEQ ID NO: 109; and (c) a CDR3 having an amino acid sequence set forth in SEQ ID NO: 110; and a heavy chain variable region comprising (a) a CDR1 having an amino acid sequence as set forth in SEQ ID NO: 78; (b) a CDR2 having an amino acid sequence as set forth in SEQ ID NO: 79; and (c) a CDR3 having an amino acid sequence set forth in SEQ ID NO: 80.

In yet another aspect of the present invention, an antagonist anti-CD40 antibody, or antigen binding portion thereof, comprises a heavy chain variable region including an amino acid sequence as set forth in SEQ ID NOs: 5, 13, 15, or 22-38; and/or a light chain variable region including an amino acid sequence as set forth in SEQ ID NOs: 9, 14, 16, 18, 20 or 43.

In a particular embodiment, the antagonist anti-CD40 antibody, or antigen-binding portion thereof, includes a heavy chain variable region including an amino acid sequence as set forth in SEQ ID NO: 5 and a light chain variable region including an amino acid sequence as set forth in SEQ ID NO: 9.

In another embodiment, the antagonist anti-CD40 antibody, or antigen-binding portion thereof, includes a heavy chain variable region including an amino acid sequence as set forth in SEQ ID NO: 13 and a light chain variable region including an amino acid sequence as set forth in SEQ ID NO:14, 16 or 18.

In another embodiment, the antagonist anti-CD40 antibody, or antigen-binding portion thereof, includes a heavy chain variable region including an amino acid sequence as set forth in SEQ ID NO: 15 and a light chain variable region including an amino acid sequence as set forth in SEQ ID NO:14, 16, 18, 20 or 43.

In another embodiment, the antagonist anti-CD40 antibody, or antigen-binding portion thereof, includes a heavy chain variable region including an amino acid sequence as set forth in SEQ ID NO: 28 and a light chain variable region including an amino acid sequence as set forth in SEQ ID NO: 20.

The antibodies described herein, particularly antibody Ab102, have antagonistic activity without substantial agonist activity for CD40. Thus, included in the invention are antibodies that bind to the epitope recognized by antibodies Ab102 and Ab101. In a particular embodiment, the invention includes an isolated antibody, or antigen binding portion thereof, wherein said antibody, or antigen binding fragment thereof, binds human CD40 such that CD40 with said antibody, or antigen binding fragment thereof, bound to an epitope defined by the topographic regions Cys62-Phe67, Gln79-Cys83, Arg90-Thr99, and Thr24-Cys37 of SEQ ID NO:1 is inhibited from binding to the CD40 ligand (CD40L). In another aspect, the invention pertains to an antibody, or antigen binding fragment thereof, capable of binding human CD40 that binds to an epitope in human CD40 comprising three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, or all of the amino acid residues Cys62-Phe67 (Cys62, Gly63, Glu64, Ser65, Glu66, Phe67), Gln79-Cys83 (Gln79, His 80, Lys81, Tyr82, Cys83), Arg90-Thr99 (Arg90, Val91, Gln92, Gln93, Lys94, Gly95, Thr96, Ser97, Glu98 and Thr99), and Thr24-Cys37 (Thr24, Ala25, Cys26, Arg27, Glu28, Lys29, Gln30, Tyr31, Leu32, Ile33, Asn34, Ser35, Gln36, Cys37) of SEQ ID NO:1.

In another embodiment, the present invention provides a heavy chain CDR2 region having antagonist activity against CD40. In particular, residue 55 (residue X) of the VH CDR2 amino acid sequence YISSGRXNIYYADTVKG (SEQ ID NO: 112) has been identified as playing a role in increasing antagonist activity of the antibody relative to a parent CDR2 sequence having residue S55. Residues Thr, Asp, Val, Leu, Ile, and Met at position 55 of the HC CDR2 result in lower levels of antagonistic activity relative to other amino acids at position 55. In one embodiment, the invention provides an antagonist anti-CD40 antibody, or antigen binding portion thereof, comprising a heavy chain variable region comprising a CDR2 having the amino acid sequence of SEQ ID NO: 111 and a light chain variable region comprising a CDR2 having the amino acid sequence of SEQ ID NO: 11. CDR1 and CDR3 domain amino acid sequences that may be combined with SEQ ID NO: 111 in variable heavy and light antibody chains are described throughout, including, for example, Tables 13 and 18.

In a further embodiment, the present invention provides a light chain CDR1 region having a residue identified as an antagonist/agonist switch. As described below in Example 3, modification of the "NS" motif of VL CDR1 region KSSQSLLNSGNQKNYLT (SEQ ID NO: 10) at residue "S" may result in an antagonist antibody switching to an agonist antibody. Thus, in one embodiment, the invention includes an antagonist anti-CD40 antibody having a CDR1 VL region comprising SEQ ID NO: 113 (KSSQSLLNXGNQKNYLT; wherein X is not amino acid residue Pro).

The term "competing antibodies" herein refers to any number of antibodies targeting the same molecular or stably but non-covalently linked supermolecular entity, preferably the same molecule, i.e., CD40, wherein at least one is capable of specifically reducing the measurable binding of another, preferably by sterically hampering the other's access to its target epitope (described above) or by inducing and/or stabilizing a conformation in the target entity that reduces the target's affinity for the other antibody, more preferably by directly blocking access to the other's target epitope by binding to an epitope in sufficiently close vicinity of the former, overlapping with the former or identical to the former, most preferably overlapping or identical, in particular identical. Two epitopes are herein said to be "overlapping" if they share part of their chemical structures, preferably their amino acid sequences, and to be "identical", if their chemical structures, preferably their amino acid sequences, are identical.

In particular embodiments, the competing antibody, or antigen-binding portion thereof, is an antibody, or antigen-binding portion thereof, that competes with any of the antibodies presented herein. In one embodiment, the invention provides a competing antibody which can compete with antibodies described herein (e.g., Ab101 or Ab102) and binds to a topographical epitope of human CD40 including residues Cys62-Phe67, Gln79-Cys83, Arg90-Thr99, and Thr24-Cys37.

In particular embodiments, the agonist antibody comprises a heavy chain variable region including (a) a CDR1 having an amino acid sequence set forth in SEQ ID NO: 6; (b) a CDR2 having an amino acid sequence as set forth in SEQ ID NO: 7; and (c) a CDR3 having an amino acid sequence set forth in SEQ ID NO: 8; and a light chain variable region including (a) a CDR1 having an amino acid sequence as set forth in SEQ ID NO: 74; (b) a CDR2 having an amino acid sequence as set forth in SEQ ID NO: 11; and (c) a CDR3 having an amino acid sequence set forth in SEQ ID NO: 12.

In other particular embodiments, the agonist antibody comprises a heavy chain variable region including (a) a CDR1 having an amino acid sequence set forth in SEQ ID NO: 6; (b) a CDR2 having an amino acid sequence as set forth in SEQ ID NO: 7; and (c) a CDR3 having an amino acid sequence set forth in SEQ ID NO: 8; and a light chain variable region including (a) a CDR1 having an amino acid sequence as set forth in SEQ ID NO: 17; (b) a CDR2 having an amino acid sequence as set forth in SEQ ID NO: 11; and (c) a CDR3 having an amino acid sequence set forth in SEQ ID NO: 12.

In further embodiments, an agonist anti-CD40 antibody, or antigen binding portion thereof, comprises a heavy chain variable region including an amino acid sequence as set forth in SEQ ID NOs: 15 or 13; and/or a light chain variable region including an amino acid sequence as set forth in SEQ ID NOs: 77 or 43.

2. Humanized Anti-CD40 Antibodies Derived from Antibody 3 (Ab3)

Amino acid sequences for humanized versions of heavy and light chains of murine Ab3 are provided in Table 11 below. Thus, the invention further features antibodies comprising the variable and/or CDR sequences from antibody 3 (Ab3).

In one aspect, the present invention provides a humanized antibody, or antigen binding portion thereof, including a light chain variable region including (a) a CDR1 having an amino acid sequence as set forth in SEQ ID NO:49; (b) a CDR2 having an amino acid sequence as set forth in SEQ ID NO: 50; and (c) a CDR3 having an amino acid sequence set forth in SEQ ID NO: 51; and a heavy chain variable region including (a) a CDR1 having an amino acid sequence as set forth in SEQ ID NO: 45; (b) a CDR2 having an amino acid sequence as set forth in SEQ ID NO: 46; and (c) a CDR3 having an amino acid sequence set forth in SEQ ID NO: 47.

Accordingly, in one aspect, the present invention is directed to an antagonist anti-CD40 antibody, or antigen-binding portion thereof, has a light chain variable region including (a) a CDR1 having an amino acid sequence as set forth in SEQ ID NO:49; (b) a CDR2 having an amino acid sequence as set forth in SEQ ID NO: 50; and (c) a CDR3 having an amino acid sequence set forth in SEQ ID NO: 51. Alternatively or in combination, the antagonist anti-CD40 antibody, or antigen-binding portion thereof, includes a heavy chain variable region including (a) a CDR1 having an amino acid sequence as set forth in SEQ ID NO: 45; (b) a CDR2 having an amino acid sequence as set forth in SEQ ID NO: 46; and (c) a CDR3 having an amino acid sequence set forth in SEQ ID NO: 47.

In yet another aspect of the present invention, an antagonist anti-CD40 antibody, or antigen binding portion thereof, comprises a heavy chain variable region including an amino acid sequence as set forth in SEQ ID NOs: 44, 52, 54 or 55; and/or a light chain variable region including an amino acid sequence as set forth in SEQ ID NOs: 48, 53, 56 or 57.

In a particular embodiment, the antagonist anti-CD40 antibody, or antigen-binding portion thereof, includes a heavy chain variable region including an amino acid sequence as set forth in SEQ ID NO: 44 and a light chain variable region including an amino acid sequence as set forth in SEQ ID NO: 48.

In another embodiment, the antagonist anti-CD40 antibody, or antigen-binding portion thereof, includes a heavy chain variable region including an amino acid sequence as set forth in SEQ ID NO: 52 and a light chain variable region including an amino acid sequence as set forth in SEQ ID NO:53, 56 or 57.

In another embodiment, the antagonist anti-CD40 antibody, or antigen-binding portion thereof, includes a heavy chain variable region including an amino acid sequence as set forth in SEQ ID NO: 54 and a light chain variable region including an amino acid sequence as set forth in SEQ ID NO:53, 56 or 57.

In another embodiment, the antagonist anti-CD40 antibody, or antigen-binding portion thereof, includes a heavy chain variable region including an amino acid sequence as set forth in SEQ ID NO: 55 and a light chain variable region including an amino acid sequence as set forth in SEQ ID NO:53, 56 or 57.

3. Anti CD40 Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454, each of which are incorporated herein by reference in their entireties) by splicing genes from a mouse antibody molecule of appropriate antigen specificity together with genes from a human antibody molecule of appropriate biological activity can be used.

In another aspect, the present invention is directed to an antagonist anti-CD40 antibody, or antigen-binding portion thereof, having a light chain variable region including (a) a CDR1 having an amino acid sequence as set forth in SEQ ID NO:10; (b) a CDR2 having an amino acid sequence as set forth in SEQ ID NO: 11; and (c) a CDR3 having an amino acid sequence set forth in SEQ ID NO: 12; and a heavy chain variable region including (a) a CDR1 having an amino acid sequence as set forth in SEQ ID NO: 6; (b) a CDR2 having an amino acid sequence as set forth in SEQ ID NO: 42; and (c) a CDR3 having an amino acid sequence set forth in SEQ ID NO: 8. In a particular embodiment, the antagonist anti-CD40 antibody, or antigen binding portion thereof, has a light chain variable region including the amino acid sequence set forth in SEQ ID NO:76 and a heavy chain variable region including the amino acid sequence set forth in SEQ ID NO:75.

In another aspect, the present invention is directed to an antagonist anti-CD40 antibody, or antigen-binding portion thereof, having a light chain variable region including (a) a CDR1 having an amino acid sequence as set forth in SEQ ID NO:49; (b) a CDR2 having an amino acid sequence as set forth in SEQ ID NO: 50; and (c) a CDR3 having an amino acid sequence set forth in SEQ ID NO: 51; and a heavy chain variable region including (a) a CDR1 having an amino acid sequence as set forth in SEQ ID NO: 45; (b) a CDR2 having an amino acid sequence as set forth in SEQ ID NO: 46; and (c) a CDR3 having an amino acid sequence set forth in SEQ ID NO: 47. In a particular embodiment, the antagonist anti-CD40 antibody, or antigen binding portion thereof, has a light chain variable region including the amino acid sequence set forth in SEQ ID NO:48 and a heavy chain variable region including the amino acid sequence set forth in SEQ ID NO:44.

In another aspect, the present invention is directed to an antagonist anti-CD40 antibody, or antigen-binding portion thereof, having a light chain variable region including (a) a CDR1 having an amino acid sequence as set forth in SEQ ID NO:10; (b) a CDR2 having an amino acid sequence as set forth in SEQ ID NO: 11; and (c) a CDR3 having an amino acid sequence set forth in SEQ ID NO: 12; and a heavy chain variable region including (a) a CDR1 having an amino acid sequence as set forth in SEQ ID NO: 6; (b) a CDR2 having an amino acid sequence as set forth in SEQ ID NO: 7; and (c) a CDR3 having an amino acid sequence set forth in SEQ ID NO: 8. In a particular embodiment, the antagonist anti-CD40 antibody, or antigen binding portion thereof, has a light chain variable region including the amino acid sequence set forth in SEQ ID NO:9 and a heavy chain variable region including the amino acid sequence set forth in SEQ ID NO:5.

The foregoing isolated anti-CD40 antibody CDR sequences establish a novel family of CD40 antibodies, or antigen binding portions thereof, isolated in accordance with this invention, and including antibodies that include the CDR sequences listed in Tables 5, 11-13, and 15-18. To generate and to select CDRs of the invention having preferred CD40 binding and/or neutralizing activity with respect to hCD40, standard methods known in the art for generating antibodies of the present invention and assessing the CD40 binding and/or neutralizing characteristics of those antibodies may be used, including but not limited to those specifically described herein.

4. Characterizing Antibodies of the Invention

Anti-CD40 antibodies of the present invention are antagonist antibodies and may exhibit a high capacity to reduce or to neutralize CD40 activity, e.g., as assessed by any one of several in vitro and in vivo assays known in the art and as described herein. In certain embodiments, the anti-CD40 antibodies of the invention are antagonistic and are substantially free of agonist activity. Antagonist and agonist activity may be determined by assays known in the art, including those described herein. For example, binding to human CD40 and inhibition of CD40-CD40L interaction can be assayed using a human CD40-expressing cell line via FACS analyses.

In one embodiment, CD40 antagonist or agonist activity of an anti-CD40 antibody is determined using a reporter cell line. For example, antagonist and agonist activities can be assessed using a CD40-expressing reporter cell line expressing human CD40 linked to NFkB mediated alkaline phosphatase (AP). When signal is received through CD40, NFkB activation leads to secretion of AP which is measured by colorimetric substrate. As an exemplary antagonist assay, a CD40 reporter line can be cultured with either Jurkat cell line expressing CD40L (to provide physiological ligand interaction) or with soluble CD40L, where the ability of the anti-CD40 antibody to block the NFkB signal (little to no presence of AP as determined by standard methods) can be assessed. As an exemplary agonist assay, a human CD40 reporter cell line can be treated with anti-CD40 antibodies and the NFkB signal measured (seen as AP presence above a negative control) as described above. An example of a CD40 reporter cell line is HEK-Blue™ CD40L Cells (InvivoGen), which serve to measure the bioactivity of CD40L through secretion of embryonic alkaline phosphatase (SEAP) upon NF-κB activation following CD40 stimulation. CD40L-CD40 interaction can be monitored by assessing the levels of SEAP using QUANTI-Blue (InvivoGen).

In one embodiment, an anti-CD40 antagonist antibody, or antigen-binding fragment thereof, of the invention has an IC50 of 0.4 nM or less, as determined by an antagonist soluble CD40L reporter assay. In one embodiment, an anti-CD40 antagonist antibody, or antigen-binding fragment thereof, of the invention has an IC50 of 51 nM or less, as determined by an antagonist CD40 reporter assay in a Jurkat cell line. In one embodiment, an anti-CD40 antagonist antibody, or antigen-binding fragment thereof, of the invention has an IC50 of 3.4 nM or less, as determined by an antagonist CD40 reporter assay in a Jurkat cell line. In one embodiment, an anti-CD40 antagonist antibody, or antigen-binding fragment thereof, of the invention has an IC50 of 0.9 nM or less, as determined by an antagonist CD40 reporter assay in a Jurkat cell line.

In one embodiment, CD40 antagonist or agonist activity of an anti-CD40 antibody is determined using a B cell agonist assay. For example, a B cell agonist assay can be utilized in which B cells are activated with low dose anti-IgM and IL4, prior to addition of a CD40 antagonist antibody. Enhancement of B cell activation can be measured as upregulation of CD86, which in turn is indicative of agonist activity. Similarly, a B cell antagonist assay can be utilized in which primary human B cells are cultured with CD40L-expressing human T cell line that leads to B cell activation and upregulation of CD86 expression via CD40/CD40L interaction Inhibition of CD86 upregulation of primary human B cells is indicative of antagonist activity.

In one embodiment, CD40 antagonist or agonist activity of an anti-CD40 antibody is determined using an antibody-dependent cell-mediated cytotoxicity (ADCC) mediated assay. Antagonist and agonist activities can be assessed by the ability of the antibody to mediate ADCC. An antagonistic CD40 antibody will be an effective mediator of ADCC, whereas an agonist antibody will not have ADCC activity. Antibody-Dependent Cellular Cytotoxicity (ADCC) refers to a type of cytotoxicity induced by activation of macrophages, NK cells, neutrophil cells, etc., which recognize target cells by binding to the constant region of the antibody via Fc receptors expressed on their surface. Complement-Dependent Cytotoxicity (CDC) refers to a type of cytotoxicity induced by activation of a complement system which occurs through binding of an antibody to an antigen. A reduction in ADCC and CDC activities means reduction in those activities as compared with, for example, a control anti-CD40 antagonist antibody such as the monoclonal antibody produced by hybridoma 4D11 (Accession No. FERM BP-7758). EP1707627B1, incorporated by reference in its entirety herein, describes assays to determine ADCC and CDC activity.

Additionally, the biological activity of dendritic cells (DCs) stimulated with immobilized anti-CD40 Ab can be used to assay agonist activity. DCs are believed to be the most potent antigen presenting cells that are capable of picking up Ags in nonlymphoid tissues and carrying them to secondary lymphoid organs to prime T cells in response to maturation stimuli such as danger and help signals. By contrast, the presentation of Ags by DCs without activation results in the elimination of effector T cells that have a cognate TCR or induction of regulatory T cells in secondary lymphoid tissues. Thus, the presence or absence of maturation signals for immature DCs in peripheral tissues acts as a switch to induce either an adaptive immune response or tolerance. The major CD4+ T cell help signal for DC maturation is provided by the interaction between CD40 expressed on DCs and CD40 ligand (L) on activated CD4+ T cells. Thus, CD40 stimulation induces the migration of DCs into secondary lymphoid tissues by up-regulating the expression of CCR7. Watanabe et al. 2003 *J Immunol;* 171:5828-5836 describes assays which may be used to determine whether anti-CD40 antibodies can activate DCs in order to determine agonistic and antagonistic activity. Such exemplary assays include determination of the expression of MHC class I/II Ag and costimulatory molecules on BM-DCs stimulated with immobilized anti-CD40 Ab, in vivo migration activity of BM-DCs stimulated with immobilized anti-CD40 Abs, in vitro migration activity and CCR7 expression of BM-DCs stimulated with immobilized anti-CD40 Ab.

In one embodiment, agonist activity of an anti-CD40 antibody, or antigen binding portion thereof, is determined using an in vitro monocyte activation assay, such as the assay described below in Example 7. An in vitro monocyte activation assay includes exposing monocytes to an anti-CD40 antibody, or antigen-binding portion thereof, where if the antibody, or antigen-binding portion thereof, is an activator of CD40 (agonist) then there is a resulting increase in TNF production. Using an in vitro monocyte activation assay, an antagonist anti-CD40 antibody, or antigen binding portion thereof, that is substantially free of agonist activity would result in the absence or minimal production of TNF, as described in Example 7.

In one embodiment, an antagonist anti-CD40 antibody, or antigen binding portion thereof, that is substantially free of agonist activity has activity that is within one standard deviation of a negative control in an in vitro CD40 agonist assay, e.g., agonist monocyte assay described in Example 7.

Agonist assays are further described in U.S. Pat. No. 5,786,456, US2011/0243932 and EP1707627B1, each of which are incorporated by reference in their entireties herein. Antagonist assays for testing antibody function are further described in U.S. Pat. No. 7,361,345, US2011/0243932 and EP1707627B1, each of which is incorporated by reference herein.

In preferred embodiments, the isolated antibody, or antigen-binding portion thereof, binds human CD40, wherein the antibody, or antigen-binding portion thereof, dissociates from human CD40 with a $k_{off}$ rate constant of about 0.1 s$^{-1}$ or less, as determined by surface plasmon resonance, or which inhibits human CD40 activity with an IC$_{50}$ of about 1×10$^{-6}$ M or less. Alternatively, the antibody, or an antigen-binding portion thereof, may dissociate from human CD40 with a $k_{off}$ rate constant of about 1×10$^{-2}$ s$^{-1}$ or less, as determined by surface plasmon resonance, or may inhibit human CD40 activity with an IC$_{50}$ of about 1×10$^{-7}$ M or less. Alternatively, the antibody, or an antigen-binding portion thereof, may dissociate from human CD40 with a $k_{off}$ rate constant of about 1×10$^{-3}$ s$^{-1}$ or less, as determined by surface plasmon resonance, or may inhibit human CD40 with an IC$_{50}$ of about 1×10$^{-8}$ M or less. Alternatively, the antibody, or an antigen-binding portion thereof, may dissociate from human CD40 with a $k_{off}$ rate constant of about 1×10$^{-4}$ s$^{-1}$ or less, as determined by surface plasmon resonance, or may inhibit CD40 activity with an IC$_{50}$ of about 1×10$^{-9}$ M or less. Alternatively, the antibody, or an antigen-binding portion thereof, may dissociate from human CD40 with a $k_{off}$ rate constant of about 1×10$^{-5}$ s$^{-1}$ or less, as determined by surface plasmon resonance, or may inhibit CD40 with an IC$_{50}$ of about 1×10$^{-10}$ M or less. Alternatively, the antibody, or an antigen-binding portion thereof, may dissociate from human CD40 with a $k_{off}$ rate constant of about 1×10$^{-5}$ s$^{-1}$ or less, as determined by surface plasmon resonance, or may inhibit CD40 activity with an IC$_{50}$ of about 1×10$^{-11}$ M or less.

The antibodies were humanized as described in the Examples below. Framework back-mutations were introduced into the CDR-grafted antibody sequences by de novo synthesis of the variable domain or by mutagenic oligonucleotide primers and polymerase chain reaction, or by both allowing different combinations of back mutations and other mutations for each of the CDR-grafts. The humanized variable regions of the murine monoclonal CD40 antibodies were cloned into IgG expression vectors for functional characterization.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

5. Generation of Anti-CD40 Humanized Antibodies

As described above, humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.htm; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immunology.html. www.immunologylink.com/; pathbox.wustl.edu/.about.h-center/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.ic-net.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl.html; www.recab.uni-hd.de/immuno.bme.nwu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh ch/.about.honegger/AHOseminar/Slide01.html; www.cryst.bbk.ac.uk/.about.ubcg07s/; www.nimr mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.abo-ut.fmolina/Web-pages/Pept/spottech.html; www.jerini.de/fr roducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

Examples of anti-CD40 humanized antibodies are provided in Sections 1 and 2 above and in the Examples below.

II. Production of Antibodies and Antibody-Producing Cell Lines

Antibodies of the present invention may be made by any of a number of techniques known in the art.

1. Anti-CD40 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1). Briefly, mice can be immunized with a CD40 antigen. In a preferred embodiment, the CD40 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a CD40 antigen, antibodies and/or antibody-producing cells may be obtained from the animal. An anti-CD40 antibody-containing serum is obtained from the animal by bleeding or sacrificing the animal. The serum may be used as it is obtained from the animal, an immunoglobulin fraction may be obtained from the serum, or the anti-CD40 antibodies may be purified from the serum. Serum or immunoglobulins obtained in this manner are polyclonal, thus having a heterogeneous array of properties.

Once an immune response is detected, e.g., antibodies specific for the antigen CD40 are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding CD40. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using CD40, or a portion thereof, or a cell expressing CD40. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-CD40 antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-CD40 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

2. Anti-CD40 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) Proc. Natl. Acad. Sci. USA 93:7843-7848. In this method, single cells secreting antibodies of interest, e.g., lymphocytes derived from any one of the immunized animals described in Section 1, are screened using an antigen-specific hemolytic plaque assay, wherein the antigen CD40, a subunit of CD40, or a fragment thereof, is coupled to sheep red blood cells using a linker, such as biotin, and used to identify single cells that secrete antibodies with specificity for CD40. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to CD40. The amplified immunoglobulin sequences further can be manipulated in vitro, such as by in vitro affinity maturation methods such as those described in PCT Publication WO 97/29131 and PCT Publication WO 00/56772.

3. Anti-CD40 Monoclonal Antibodies Using Transgenic Animals

In another embodiment of the instant invention, antibodies are produced by immunizing a non-human animal comprising some, or all, of the human immunoglobulin locus with a CD40 antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

4. Anti-CD40 Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with CD40, or a portion of CD40, such as the extracellular domain. Alternatively, the recombinant antibody library may be from a naïve subject, i.e., one who has not been immunized with CD40, such as a human antibody library from a human subject who has not been immunized with human CD40. Antibodies of the invention are selected by screening the recombinant antibody library with the peptide comprising human CD40 to thereby select those antibodies that recognize CD40. Methods for conducting such screening and selection are well known in the art, such as described in the references in the preceding paragraph. To select antibodies of the invention having particular binding affinities for hCD40, such as those that dissociate from human CD40 with a particular $k_{off}$ rate constant, the art-known method of surface plasmon resonance can be used to select antibodies having the desired $k_{off}$ rate constant. To select antibodies of the invention having a particular neutralizing activity for hCD40, such as those with a particular an $IC_{50}$, standard methods known in the art for assessing the inhibition of hCD40 activity may be used.

In one aspect, the invention pertains to an isolated antibody, or an antigen-binding portion thereof, that binds human CD40. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., Gene 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780, 225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup et al. (U.S. Pat. No. 6,699,658) incorporated herein by reference.

5. Production of Recombinant CD40 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Another embodiment of the invention provides a glycosylated antibody, or an antigen-binding portion thereof, wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the present invention is directed to generating glycosylation site mutants in which the O- or N-linked glycosylation site of the antibody, or an antigen-binding portion thereof, has been mutated. One skilled in the art can generate such mutants using standard well-known technologies. Glycosylation site mutants that retain the biological activity, but have increased or decreased binding activity, are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated antibody, or an antigen-binding portion thereof, comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

In addition to the antibodies, or antigen binding portions thereof, the present invention is also directed to an anti-idiotypic (anti-Id) antibody specific for such antibodies, or antigen binding portions thereof, of the invention. An anti-Id antibody is an antibody, which recognizes unique determinants generally associated with the antigen-binding region of another antibody. The anti-Id can be prepared by immunizing an animal with the antibody, or antigen binding portion thereof, or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

III. Uses of Antagonistic Anti-CD40 Antibodies

Given their ability to bind to human CD40, the anti-human CD40 antibodies, or portions thereof, of the invention can be used to detect human CD40 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting human CD40 in a biological sample comprising contacting a biological sample with an antibody, or antibody portion, of the invention and detecting either the antibody (or antibody portion) bound to human CD40 or unbound antibody (or antibody portion), to thereby detect human CD40 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human CD40 can be assayed in biological fluids by a competition immunoassay utilizing rhCD40 standards labeled with a detectable substance and an unlabeled anti-human CD40 antibody. In this assay, the biological sample, the labeled rhCD40 standards and the anti-human CD40 antibody are combined and the amount of labeled rhCD40 standard bound to the unlabeled antibody is determined. The amount of human CD40 in the biological sample is inversely proportional to the amount of labeled rhCD40 standard bound to the anti-CD40 antibody. Similarly, human CD40 can also be assayed in biological fluids by a competition immunoassay utilizing rhCD40 standards labeled with a detectable substance and an unlabeled anti-human CD40 antibody.

The antibodies and antibody portions of the invention preferably are capable of neutralizing human CD40 activity both in vitro and in vivo. Accordingly, such antibodies and antibody portions of the invention can be used to inhibit hCD40 activity, e.g., in a cell culture containing hCD40, in human subjects or in other mammalian subjects having CD40 with which an antibody of the invention cross-reacts. In one embodiment, the invention provides a method for inhibiting hCD40 activity comprising contacting hCD40 with an antibody or antibody portion of the invention such that hCD40 activity is inhibited. For example, in a cell culture containing, or suspected of containing hCD40, an antibody or antibody portion of the invention can be added to the culture medium to inhibit hCD40 activity in the culture.

In another embodiment, the invention provides a method for reducing hCD40 activity in a subject, advantageously from a subject suffering from a disease or disorder in which CD40 activity is detrimental. The invention provides methods for reducing CD40 activity in a subject suffering from such a disease or disorder, which method comprises administering to the subject an antibody or antibody portion of the invention such that CD40 activity in the subject is reduced. Preferably, the CD40 is human CD40, and the subject is a human subject. Alternatively, the subject can be a mammal expressing a CD40 to which an antibody of the invention is capable of binding. Still further the subject can be a mammal into which CD40 has been introduced (e.g., by administration of CD40 or by expression of a CD40 transgene). An antibody of the invention can be administered to a human subject for therapeutic purposes. Moreover, an antibody of the invention can be administered to a non-human mammal expressing a CD40 with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which CD40 activity is detrimental" is intended to include diseases and other disorders in which the presence of CD40 in a subject suffering from the disorder has been shown to be or is suspected of being either responsible for the pathophysiology of the disorder or a factor that contributes to a worsening of the disorder. Accordingly, a disorder in which CD40 activity is detrimental is a disorder in which reduction of CD40 activity is expected to alleviate the symptoms and/or progression of the disorder. Such disorders may be evidenced, for example, by an increase in the concentration of CD40 in a biological fluid of a subject suffering from the disorder (e.g., an increase in the concentration of CD40 in serum, plasma, synovial fluid, etc. of the subject), which can be detected, for example, using an anti-CD40 antibody as described above. Non-limiting examples of disorders that can be treated with the antibodies of the invention, and variants thereof, or antigen binding fragments thereof, include those disorders discussed in the section below pertaining to pharmaceutical compositions of the antibodies of the invention. For example, suitable disorders include, but are not limited to, systemic lupus erythematosus (SLE), discoid lupus, lupus nephritis, sarcoidosis, juvenile arthritis, rheumatoid arthritis, psoriatic arthritis, Reiter's syndrome, ankylosing spondylitis, gouty arthritis, rejection of an organ or tissue transplant, graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, asthma, Churg-Strauss syndrome (allergic granulomatosis), atopic dermatitis, allergic and irritant contact dermatitis, urticaria, IgE-mediated allergy, atherosclerosis, vasculitis, idiopathic inflammatory myopathies, hemolytic disease, Alzheimer's disease, and chronic inflammatory demyelinating polyneuropathy. In a particular embodiment, the disease or disorder is a chronic inflammatory disorder. In a particular embodiment, the disorder in which CD40 activity is detrimental is an inflammatory bowel disease (IBD), including, but not limited to, Crohn's disease or ulcerative colitis.

In other embodiments, the anti-CD40 antibody, or antigen binding portion, of the invention is used to treat a disorder in which TNFα activity is detrimental, including, but not limited to, rheumatoid arthritis, ulcerative colitis, hidradenitis suppurativa, juvenile idiopathic arthritis, psoriatic arthritis, psoriasis, ankylosing spondylitis, and Crohn's disease. In one embodiment, the disorder in which TNFα activity is detrimental is uveitis.

In one embodiment, an anti-CD40 antibody, or antigen-binding portion thereof, of the invention, e.g. Ab102, is used to treat a human subject having an inflammatory bowel disease (IBD).

In one embodiment, an anti-CD40 antibody, or antigen-binding portion thereof, of the invention, e.g. Ab102, is used to treat ulcerative colitis.

In one embodiment, an anti-CD40 antibody, or antigen-binding portion thereof, of the invention, e.g. Ab102, is used to treat Crohn's disease.

In one embodiment, an anti-CD40 antibody, or antigen-binding portion thereof, of the invention, e.g. Ab102, is used to treat systemic lupus erythematosus (SLE).

In one embodiment, an anti-CD40 antibody, or antigen-binding portion thereof, of the invention, e.g. Ab102, is used to treat sarcoidosis.

In one embodiment, an anti-CD40 antibody, or antigen-binding portion thereof, of the invention, e.g. Ab102, is used to treat a human subject having juvenile arthritis.

In one embodiment, an anti-CD40 antibody, or antigen-binding portion thereof, of the invention, e.g. Ab102, is used to treat rheumatoid arthritis.

In one embodiment, an anti-CD40 antibody, or antigen-binding portion thereof, of the invention, e.g. Ab102, is used to treat psoriatic arthritis.

In one embodiment, an anti-CD40 antibody, or antigen-binding portion thereof, of the invention, e.g. Ab102, is used to treat a human subject having ankylosing spondylitis.

In one embodiment, an anti-CD40 antibody, or antigen-binding portion thereof, of the invention, e.g. Ab102, is used to treat hidradenitis suppurativa.

In one embodiment, an anti-CD40 antibody, or antigen-binding portion thereof, of the invention, e.g. Ab102, is used to treat uveitis.

In one embodiment, an anti-CD40 antibody, or antigen-binding portion thereof, of the invention, e.g. Ab102, is used to treat Sjogren's.

In one embodiment, an anti-CD40 antibody, or antigen-binding portion thereof, of the invention, e.g. Ab102, is used to treat psoriasis.

In one embodiment, an anti-CD40 antibody, or antigen-binding portion thereof, of the invention, e.g. Ab102, is used to treat atopic dermatitis.

In one embodiment, an anti-CD40 antibody, or antigen-binding portion thereof, of the invention, e.g. Ab102, is used to treat scleroderma.

Anti-CD40 mAbs of the present invention will have the potential to treat both biologic naïve patients and anti-TNF inadequate responder populations due to the central role of CD40 in both innate and adaptive immune responses. The present invention provides a treatment capable of inhibiting CD40 signaling suppresses molecular pathways such as TNF and IL-23 production and adhesion/co-stimulatory molecule expression that maintain chronic inflammation in the gut. Based on expression profiling of anti-TNF treated Crohn's patients, treatment with anti-CD40 may have the potential to extend beyond the anti-TNF responder population to treat a broader segment of Crohn's patients. In certain embodiments, the invention provides a method of treating a subpopulation of IBD patients who fail to respond to anti-TNF therapy. Such IBD patients may have Crohn's disease or ulcerative colitis and have either failed to respond to or have had a limited response to treatment with a TNFα inhibitor, such as, but not limited to, infliximab, adalimumab, certolizumab pegol, or golimumab. The anti-CD40 antagonist antibodies described herein may be used, in to treat a TNF non-responder who has Crohn's disease or ulcerative colitis. In certain embodiments, the invention includes a method of treating a treat patient, e.g., an adult patient, with moderately to severely active Crohn's disease who is an anti-TNF non-responder.

Antibodies of the invention, or antigen-binding portions thereof, can be used alone or in combination to treat such diseases. It should be understood that the antibodies of the invention or antigen-binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition, e.g., an agent which affects the viscosity of the composition. It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more CD40 antagonists, e.g., anti-CD40 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In one embodiment, an anti-CD40 antibody, or antigen-binding portion thereof, of the invention, e.g. Ab102, is used in combination with a second agent to treat an inflammatory bowel disease (IBD). In certain embodiments, the second agent is mesalamine, balsalazide, azathioprine, 6-MP, methotrexate, infliximab, certolizumab, adalimumab, golimumab, natalizumab, vedolizumab, ustekinumab, or combinations thereof.

In one embodiment, an anti-CD40 antibody, or antigen-binding portion thereof, of the invention, e.g. Ab102, is used in combination with a second agent to treat SLE, where the second agent is nitropaste/nitroglycerin, nifedipine, sildenafil, tadalifil, or combinations thereof.

In one embodiment, an anti-CD40 antibody, or antigen-binding portion thereof, of the invention, e.g. Ab102, is used in combination with a second agent to treat SLE, where the second agent is a corticosteroid, an endogenous steroid producer, an NSAID, an anti-inflammatory agent, a disease-modifying antirheumatic drug (DMARD), an immunosuppressive agent, an anti-coagulant, or combinations thereof.

In one embodiment, an anti-CD40 antibody, or antigen-binding portion thereof, of the invention, e.g. Ab102, is used in combination with a corticosteroid to treat SLE. Examples of corticosteroids that may be used include prednisolone, methylprednisolone, prednisone, or combinations thereof.

In one embodiment, an anti-CD40 antibody, or antigen-binding portion thereof, of the invention, e.g. Ab102, is used in combination with an agent that effects endogenous steroid production, e.g., corticotropin (Acthar), to treat SLE.

In one embodiment, an anti-CD40 antibody, or antigen-binding portion thereof, of the invention, e.g. Ab102, is used in combination with a topical or injected therapy to treat SLE. An example of such a therapy includes, but is not limited to, cortisone, hydrocortisone, pimecrolimus cream, tacrolimus ointment, imiquimod, or combinations thereof.

In one embodiment, an anti-CD40 antibody, or antigen-binding portion thereof, of the invention, e.g. Ab102, is used in combination with a nonsteroidal anti-inflammatory drug (NSAID) to treat SLE. An example of an NSAID that may be used in a combination therapy includes, but is not limited to, indomethacin, nabumetone, celecoxib, ibuprofen, naproxen, diclofenac, or combinations thereof.

In one embodiment, an anti-CD40 antibody, or antigen-binding portion thereof, of the invention, e.g. Ab102, is used in combination with an anti-inflammatory drug to treat SLE. In further embodiments, the anti-inflammatory drug is acetaminophen and/or a salicylates.

In one embodiment, an anti-CD40 antibody, or antigen-binding portion thereof, of the invention, e.g. Ab102, is used in combination with a disease-modifying antirheumatic drugs (DMARD) to treat SLE. An example of a DMARD includes, but is not limited to, hydroxychloroquine (Plaquenil), chloroquine, methotrexate (Rheumatrex), leflunomide (Arava), sulfasalazine, or combinations thereof.

In one embodiment, an anti-CD40 antibody, or antigen-binding portion thereof, of the invention, e.g. Ab102, is used in combination with Belimumab (Benlysta), Rituximab (Rituxan), intravenous Ig, or combinations thereof.

In one embodiment, an anti-CD40 antibody, or antigen-binding portion thereof, of the invention, e.g. Ab102, is used in combination with an immunosuppressive agent to treat SLE. Examples of an immunosuppressive agent include, but are not limited to, azathioprine (Imuran), cyclophosphamide (Cytoxan), cyclosporine, tacrolimus, and mycophenolate.

In one embodiment, an anti-CD40 antibody, or antigen-binding portion thereof, of the invention, e.g. Ab102, is used in combination with an anti-coagulant agent to treat SLE. Examples of an anticoagulant agent include, but are not limited to, aspirin, heparin, warfarin, and enoxaparin (Lovenox).

Further examples of preferred additional therapeutic agents that can be co-administered and/or formulated with one or more CD40 antagonists, e.g., anti-CD40 antibodies or fragments thereof. Such combinations can be used to treat CD40 related disorders as set forth herein. Additional examples of therapeutic agents that can be co-administered and/or formulated with one or more anti-CD40 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; nonsteroidal anti-inflammatory drugs (NSAIDs); immunomodulators; p38 inhibitors; TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and endothelin-1, as well as the receptors of these cytokines and growth factors. Antibodies of the invention, or antigen-binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade; preferred examples include TNF antagonists like chimeric, humanized or human TNF antibodies, adalimumab, (HUMIRA; D2E7; PCT Publication No. WO 97/29131), CA2 (REMICADE), CDP 571, and soluble p55 or p75 TNF receptors, derivatives, thereof, (p75TNFR1gG (ENBREL) or p55TNFR1gG (LENERCEPT), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application features a method of treating (e.g., curing, suppressing, ameliorating, delaying or preventing the onset of, or preventing recurrence or relapse of) or preventing a disorder in which CD40 activity is detrimental, in a subject. The method includes: administering to the subject a CD40 binding agent (particularly an antagonist), e.g., an anti-CD40 antibody or fragment thereof as described herein, in an amount sufficient to treat or prevent the CD40-associated disorder. The CD40 antagonist, e.g., the anti-CD40 antibody or fragment thereof, can be administered to the subject, alone or in combination with other therapeutic modalities as described herein.

In another aspect, this application provides a method for detecting the presence of CD40 in a sample in vitro (e.g., a biological sample, such as serum, plasma, tissue, biopsy). The subject method can be used to diagnose a disorder, e.g., an inflammatory disorder. The method includes: (i) contacting the sample or a control sample with the anti-CD40 antibody or fragment thereof as described herein; and (ii) detecting formation of a complex between the anti-CD40 antibody or fragment thereof, and the sample or the control sample, wherein a statistically significant change in the formation of the complex in the sample relative to the control sample is indicative of the presence of CD40 in the sample.

In yet another aspect, this application provides a method for detecting the presence of CD40 in vivo (e.g., in vivo imaging in a subject). The subject method can be used to diagnose a disorder, e.g., a CD40-associated disorder. The method includes: (i) administering the anti-CD40 antibody or fragment thereof as described herein to a subject or a control subject under conditions that allow binding of the antibody or fragment to CD40; and (ii) detecting formation of a complex between the antibody or fragment and CD40, wherein a statistically significant change in the formation of the complex in the subject relative to the control subject is indicative of the presence of CD40.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled antibody, or an antigen-binding portion thereof, wherein an antibody or antibody portion of the invention is derivatized or linked to one or more functional molecule(s) (e.g., another peptide or protein). For example, a labeled antibody, or an antigen-binding portion thereof, of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized antibody, or an antigen-binding portion thereof. Preferably the invention relates to crystals of whole anti-CD40 antibodies and fragments thereof as disclosed herein, and formulations and compositions comprising such crystals. In one embodiment the crystallized antibody, or an antigen-binding portion thereof, has a greater half-life in vivo than the soluble counterpart of the antibody, or an antigen-binding portion thereof. In another embodiment the antibody, or an antigen-binding portion thereof, retains biological activity after crystallization.

Crystallized antibody, or an antigen-binding portion thereof, of the invention may be produced according methods known in the art and as disclosed in WO 02072636, incorporated herein by reference.

IV. Pharmaceutical Compositions

The invention also provides pharmaceutical compositions comprising an antibody, or antigen-binding portion thereof, of the invention and a pharmaceutically acceptable carrier.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which CD40 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as silastic membranes, polymers, fibrous matrices (e.g., TISSUEL), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679, 377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotherphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as HYLENEX (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

In one embodiment, the invention includes a pharmaceutical composition comprising an antibody of the invention, e.g., antibody Ab102, histidine and a polysorbate, e.g., polysorbate 80. In one embodiment, the invention includes a pharmaceutical composition comprising an antibody comprising a heavy chain comprising the amino acids of SEQ ID NO: 41 and a light chain comprising the amino acids of SEQ ID NO: 40, histidine and a polysorbate, e.g., polysorbate 80. In certain embodiments, the pharmaceutical composition is lyophilized.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In other embodiments, an antibody or antibody portion of the invention may be conjugated to a polymer-based species such that said polymer-based species may confer a sufficient size upon said antibody or antibody portion of the invention such that said antibody or antibody portion of the invention benefits from the enhanced permeability and retention effect (EPR effect) (See also PCT Publication No. WO2006/042146A2 and U.S. Publication Nos. 2004/0028687A1, 2009/0285757A1, and 2011/0217363A1, and U.S. Pat. No. 7,695,719 (each of which is incorporated by reference herein in its entirety and for all purposes).

Supplementary active compounds can also be incorporated into the compositions. In certain embodiments, an antibody or antibody portion of the invention is formulated with and/or co-administered with one or more additional therapeutic agents that are useful for treating disorders in which CD40 activity is detrimental. For example, an anti-hCD40 antibody or antibody portion of the invention may be formulated and/or co-administered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to CD40 or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley &Sons, N Y (1993); and Kriegler, Gene Transfer and Expression, A Laboratory Manual, Stockton Press, NY (1990). Detailed description of various methods of gene therapy is provided in US20050042664 A1 which is incorporated herein by reference.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Antagonist Anti-Human CD40 (hCD40) Monoclonal Antibodies

In order to identify CD40 specific antagonist antibodies, hybridoma technology was used to isolate murine monoclonal anti-CD40 antibodies.

Briefly, mice were immunized with human CD40 antigen and adjuvant. After immunization, which included several administrations of the antigen over several weeks, serum from each immunized animal was collected. The serum was then tested using standard ELISA and flow cytometry assays to identify serum having antibodies that were able to detect CD40. Once the presence of CD40-specific antibodies was detected in the mouse serum based on the binding assays, the mouse spleen was harvested and antibody-producing cells were isolated according to standard techniques. The splenocytes were then fused by known techniques to form antibody-producing myeloma cells. After fusion, hybridomas were screened by ELISA and flow cytometry to determine the various antibody CD40 blocking and neutralization characteristics.

Following screening, while the majority of antibodies were identified as having agonist activity, three of the murine monoclonal antibodies (Ab1, Ab2 and Ab3) were identified as having antagonist activity to CD40 without substantial agonist activity. The heavy and light chain amino acid sequences of these three murine antibodies are described below in Tables 7 to 9. CDRs within the variable heavy (VH) and variable light (VL) chains are shown by bold text (CDR1, CDR2, and CDR3, respectively).

TABLE 7

VH and VL amino acid sequences of murine antibody 1 (Ab 1)

| SEQ ID NO. | Clone name | Antibody Region | Residue description | Amino acid sequence |
|---|---|---|---|---|
| 5 | Ab1 | VH | | EVQLVESGGGLVKPGGSLKVSCAASGFTFS DYGMNWVRQAPEKGLEWIAYISSGRSNIYY ADTVKGRFTISRDNAKNTLFLQMTSLRSED TAMYYCARSWGYFDVWGIGTTVTVSS |
| 6 | Ab1 | CDR-H1 | Residues 26-35 of SEQ ID NO.: 5 | GFTFSDYGMN |
| 7 | Ab1 | CDR-H2 | Residues 50-66 of SEQ ID NO.: 5 | YISSGRSNIYYADTVKG |
| 8 | Ab1 | CDR-H3 | Residues 99-105 of SEQ ID NO.: 5 | SWGYFDV |
| 9 | Ab1 | VL | | DIVMTQSPSSLTVTAGEMVTMSCKSSQSLL NSGNQKNYLTWFQQKPGQPPKLLIYWASTR ESGVPDRFAGSGSGTDFTLTISSVQAEDLA VYYCQNDYTYPLTFGAGTKLEIK |
| 10 | Ab1 | CDR-L1 | Residues 24-40 of SEQ ID NO.: 9 | KSSQSLLNSGNQKNYLT |
| 11 | Ab1 | CDR-L2 | Residues 56-62 of SEQ ID NO.: 9 | WASTRES |
| 12 | Ab1 | CDR-L3 | Residues 95-103 of SEQ ID NO.: 9 | QNDYTYPLT |

TABLE 8

VH and VL amino acid sequences of murine antibody 3 (Ab3)

| SEQ ID NO. | Clone name | Antibody Region | Residue description | Amino acid sequence |
|---|---|---|---|---|
| 44 | Ab3 | VH | | QVQLQQSGAELARPGASVKMSCKAFGYTFT SYTMHWVKQRPGQGLEWIGYINPSSDYPNY NQKFKDKATLTADKSSTAMMQLSSLTSED SAVYYCARWGYSFDYWGQGTTLTVSS |
| 45 | Ab3 | CDR-H1 | Residues 26-35 of SEQ ID NO.: 44 | GYTFTSYTMH |
| 46 | Ab3 | CDR-H2 | Residues 50-66 of SEQ ID NO.: 44 | YINPSSDYPNYNQKFKD |
| 47 | Ab3 | CDR-H3 | Residues 99-105 of SEQ ID NO.: 44 | WGYSFDY |
| 48 | Ab3 | VL | | DIVMTQAAPSVSVIPGESVSISCRSSKSLL HSNGNTYLYWFLQRPGQSPQYLIYRMSTLA SGVPDRFSGSGSGTAFTLRISRVEAEDVGV YYCMQHLEYPLTFGAGTKLELK |
| 49 | Ab3 | CDR-L1 | Residues 24-39 of SEQ ID NO.: 48 | RSSKSLLHSNGNTYLY |
| 50 | Ab3 | CDR-L2 | Residues 55-61 of SEQ ID NO.: 48 | RMSTLAS |
| 51 | Ab3 | CDR-L3 | Residues 94-102 of SEQ ID NO.: 48 | MQHLEYPLT |

TABLE 9

VH and VL amino acid sequences of murine antibody 2 (Ab2)

| SEQ ID NO. | Clone name | Antibody Region | Residue description | Amino acid sequence |
|---|---|---|---|---|
| 75 | Ab2 | VH | | EVQLVESGGGLVKPGGSLKVSCAASGFTFS DYGMNWVRQSPEKGLEWIAYISSGRGNIYY ADTVKGRFTISRDNAKNTLFLQMTSLRSED TAMYYCARSWGYFDVWGTGTTVTVSS |
| 6 | Ab2 | CDR-H1 | Residues 26-35 of SEQ ID NO.: 75 | GFTFSDYGMN |
| 42 | Ab2 | CDR-H2 | Residues 50-66 of SEQ ID NO.: 75 | YISSGRGNIYYADTVKG |
| 8 | Ab2 | CDR-H3 | Residues 99-105 of SEQ ID NO.: 75 | SWGYFDV |
| 76 | Ab2 | VL | | DIVMTQSPSSLTVTAGEKVTMSCKSSQSLL NSGNQKNYLTWFQQKPGQPPKLLIYWASTR ESGVPDRFTGSGSGTDFTLTISSVQAEDLA VYYCQNDYTYPLTFGAGTKLELK |
| 10 | Ab2 | CDR-L1 | Residues 24-40 of SEQ ID NO.: 76 | KSSQSLLNSGNQKNYLT |
| 11 | Ab2 | CDR-L2 | Residues 56-62 of SEQ ID NO.: 76 | WASTRES |
| 12 | Ab2 | CDR-L3 | Residues 95-103 of SEQ ID NO.: 76 | QNDYTYPLT |

Consensus sequences of the CDR regions from the three anti-CD40 antagonist murine monoclonal antibodies (Ab1, Ab2 and Ab3) were identified and are provided above in Table 5. Alignments of the variable region amino acid sequences of the three murine antibodies are also provided in FIGS. 4A (light chain) and 4B (heavy chain).

The murine heavy and light chain variable regions (VH and VL) of the three antibodies were cloned using reverse transcriptase-PCR (RT-PCR). These VH and VL regions (described above in Tables 7 to 9) were subsequently cloned into vectors comprising human immunoglobulin (Ig) constant regions, and then expressed in mammalian host cells as chimeric antibodies. These human chimeric antibodies (human constant and murine variable regions) were then characterized using in vitro assays to determine whether they each had an antagonist and/or agonist effect.

FACS analysis was used to determine whether the three chimeric anti-CD40 antibodies could bind either huCD40 or cyno CD40 expressed on Human Embryonic Kidney (HEK) cells. While each of the three chimeric antibodies could bind human CD40 expressed on HEK cells, only two of the chimeric antibodies recognized cyno-chimeric Antibody 3 (chAb3) did not bind to cyno CD40. The results of the FACS binding study are summarized in Table 10.

FACS analysis was also used to determine whether the three chimeric antibodies could inhibit binding of soluble CD40 ligand (sCD40L) to CD40. Using CD40 expressing HEK cells, IC50 values were measured. As described in Table 10, each of the chimeric antibodies was able to block CD40 binding to its ligand.

In addition to binding assays, antagonist and agonist activities were measured using a CD40-expressing reporter cell line expressing human CD40 linked to NFkB mediated alkaline phosphatase (AP). In the CD40-expressing reporter cell line assay, when signal is received through CD40, NFkB activation leads to secretion of AP which is measured by colorimetric substrate. To determine antagonist activity, the CD40 reporter cell line (HEK) was cultured with either with Jurkat cell line expressing CD40L (to provide physiological ligand interaction) or with soluble CD40L (e.g., His-CD40L referenced in Table 10). The ability of anti-CD40 antibodies to block the NFkB signal was measured. To measure agonist activity, human CD40 reporter cell line was directly treated with anti-CD40 antibodies and NFkB signal was measured. Representative CD40 antagonist and agonist assay data for the three chimeric antibodies are summarized in Table 10 and FIGS. 1A and 1B.

TABLE 10

Summary of Functional Characteristics of anti-CD40 Chimeric Antibodies

| Chimeric CD40 Antibodies (hCg1-LALA) | HEK huCD40 FACS binding | HEK cyCD40 FACS binding | HEK CD40 FACS Blocking IC50 nM | Agonist: HEK huCD40 reporter assay | Antagonist: His-CD40L reporter assay IC50 nM | Antagonist: Jurkat/Reporter assay IC50 nM |
|---|---|---|---|---|---|---|
| chimeric Ab1 (chAb1) | Yes | Yes | 2.3 | No | 0.4 | 51 |
| chimeric Ab3 (chAb3) | Yes | No | 1.4 | No | 0.2 | 0.9 |

TABLE 10-continued

Summary of Functional Characteristics of anti-CD40 Chimeric Antibodies

| Chimeric CD40 Antibodies (hCg1-LALA) | HEK huCD40 FACS binding | HEK cyCD40 FACS binding | HEK CD40 FACS Blocking IC50 nM | Agonist: HEK huCD40 reporter assay | Antagonist: His-CD40L reporter assay IC50 nM | Antagonist: Jurkat/Reporter assay IC50 nM |
|---|---|---|---|---|---|---|
| chimeric Ab2 (chAb2) | Yes | Yes | 1.4 | No | 0.3 | 3.4 |

As described in Table 10 and FIG. 1, the anti-CD40 chimeric antibodies showed antagonist activity with no detectable agonist activity. Based on the results from the above experiments, the heavy and light chain variable regions from anti-CD40 antagonist antibodies Ab1, and Ab3 were selected for humanization.

Example 2

Humanization of Antagonist Anti-CD40 Antibodies Ab1 and Ab3

Humanization of Antagonist Anti-CD40 Antibody Ab1

Humanized antibodies were generated based on the variable heavy (VH) and variable light (VL) CDR sequences of Ab1. Specifically, human germline sequences were selected for constructing CDR-grafted, humanized Ab1 antibodies, where the CDR domains of the VH and VL chains of Ab1 was grafted onto different human heavy and light chain acceptor sequences. Based on the alignments with the VH and VL sequences of monoclonal antibody Ab1, the following human sequences were selected as acceptors:
1. IGHV3-21*01 and IGHJ6*01 for constructing heavy chain acceptor sequences
2. IGHV3-48*01 and IGHJ6*01 as an alternative acceptor for constructing heavy chain
3. IGKV4-1*01 and IGKJ2*01 for constructing light chain acceptor sequences
4. IGKV2-40*01 and IGKJ2*01 as an alternative acceptor for constructing light chain CDR-grafted antibodies were then prepared by grafting the corresponding VH and VL CDRs of Ab1 into the acceptor sequences described in 1-4 above.

To generate a humanized antibody with framework back-mutation(s), framework mutations were identified and introduced into the CDR-grafted antibodies. These mutations were introduced using standard techniques, including de novo synthesis of the variable domain with the backmutation(s) and mutagenic oligonucleotide primers in polymerase chain reactions. Different combinations of back mutations and other mutations were constructed for each of the CDR-grafted antibodies (containing the CDRs of antibody Ab1) as follows. (Note: Residue numbers for the below-mentioned mutations are based on the Kabat numbering system.)

For the heavy chains of the CDR-grafted antibodies, one or more of the following Vernier and VH/VL interfacing residues were back mutated: V48I and/or S49A.

For light chains of the CDR-grafted antibodies, the following Vernier and VH/VL interfacing residue was back mutated: Y36F.

Descriptions of the variable regions of the humanized antibodies derived from murine monoclonal Ab1 are provided below:
Humanized Ab1 (huAb1VH.1) is a CDR-grafted Ab1 VH containing IGHV3-21*01 and IGHJ6*01 framework sequences;
Humanized Ab1VH.1a (huAb1VH.1A) is a humanized heavy chain comprising the amino acid sequences of huAb1VH.1 with the following two framework back-mutations: V48I, S49A;
Humanized Ab1VL.1 (huAb1VL.1) is a CDR-grafted Ab1 VL containing IGKV4-1*01 and IGKJ2*01 framework sequences; and
Humanized Ab1VL.1a (huAb1VL.1A) is a humanized light chain based on huAb1VL.1 and contains 1 proposed framework back-mutations: Y36F.

Note: IGHV3-21_IGHJ6 refers to an antibody comprising variable sequences corresponding to IGHV3-21*01 and IGHJ6*01.

The humanized variable regions were then cloned into IgG expression vectors for functional characterization of four different humanized antibodies based on the following heavy and light chain variable region combinations:
A. huAb1VH.1/VL.1
B. huAb1VH.1A/VL.1
C. huAb1VH.1/VL.1A
D. huAb1VH.1A/VL.1A The variable region and CDR amino acid sequences of the foregoing humanized antibodies are described in Table 11 below.

TABLE 11

VH and VL sequences of humanized versions of antibody 1 (huAb1)

| SEQ ID NO: | Clone | Antibody Region | Residues | Amino acid sequence |
|---|---|---|---|---|
| 13 | huAb1VH.1/VL.1 VH | VH | | EVQLVESGGGLVKPGGSLRLSCAASGFTF SDYGMNWVRQAPGKGLEWVSYISSGRSNI YYADTVKGRFTISRDNAKNSLYLQMNSLR AEDTAVYYCARSWGYFDVWGQGTTVTVSS |
| 6 | huAb1VH.1/VL.1 | CDR-H1 | Residues 26-35 of SEQ ID NO.: 13 | GFTFSDYGMN |

TABLE 11-continued

VH and VL sequences of humanized versions of antibody 1 (huAb1)

| SEQ ID NO: | Clone | Antibody Region | Residues | Amino acid sequence |
|---|---|---|---|---|
| 7 | huAb1VH.1/VL.1 | CDR-H2 | Residues 50-66 of SEQ ID NO.: 13 | YISSGRSNIYYADTVKG |
| 8 | huAb1VH.1/VL.1 | CDR-H3 | Residues 99-105 of SEQ ID NO.: 13 | SWGYFDV |
| 14 | huAb1VH.1/VL.1 VL | VL | | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYTYPLTFGQGTKLEIK |
| 10 | huAb1VH.1/VL.1 | CDR-L1 | Residues 24-40 of SEQ ID NO.: 14 | KSSQSLLNSGNQKNYLT |
| 11 | huAb1VH.1/VL.1 | CDR-L2 | Residues 56-62 of SEQ ID NO.: 14 | WASTRES |
| 12 | huAb1VH.1/VL.1 | CDR-L3 | Residues 95-103 of SEQ ID NO.: 14 | QNDYTYPLT |
| 15 | huAb1VH.1A/VL.1 | VH | | EVQLVESGGGLVKPGGSLRLSCAASGFTFSDYGMNWVRQAPGKGLEWIAYISSGRSNIYYADTVKGRFTISRDNAKNSLYLQMNSLRAEDTAVYYCARSWGYFDVWGQGTTVTVSS |
| 6 | huAb1VH.1A/VL.1 | CDR-H1 | Residues 26-35 of SEQ ID NO.: 15 | GFTFSDYGMN |
| 7 | huAb15VH.1A/VL.1 | CDR-H2 | Residues 50-66 of SEQ ID NO.: 15 | YISSGRSNIYYADTVKG |
| 8 | huAb1VH.1A/VL.1 | CDR-H3 | Residues 99-105 of SEQ ID NO.: 15 | SWGYFDV |
| 14 | huAb1VH.1A/VL.1 | VL | | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYTYPLTFGQGTKLEIK |
| 10 | huAb1VH.1A/VL.1 | CDR-L1 | Residues 24-40 of SEQ ID NO.: 14 | KSSQSLLNSGNQKNYLT |
| 11 | huAb1VH.1A/VL.1 | CDR-L2 | Residues 56-62 of SEQ ID NO.: 14 | WASTRES |
| 12 | huAb1VH.1A/VL.1 | CDR-L3 | Residues 95-103 of SEQ ID NO.: 14 | QNDYTYPLT |
| 13 | huAb1VH.1/VL.1A VH | VH | | EVQLVESGGGLVKPGGSLRLSCAASGFTFSDYGMNWVRQAPGKGLEWVSYISSGRSNIYYADTVKGRFTISRDNAKNSLYLQMNSLRAEDTAVYYCARSWGYFDVWGQGTTVTVSS |
| 6 | huAb1VH.1/VL.1A | CDR-H1 | Residues 26-35 of SEQ ID NO.: 13 | GFTFSDYGMN |
| 7 | huAb1VH.1/VL.1A | CDR-H2 | Residues 50-66 of SEQ ID NO.: 13 | YISSGRSNIYYADTVKG |
| 8 | huAb1VH.1/VL.1A | CDR-H3 | Residues 99-105 of SEQ ID NO.: 13 | SWGYFDV |
| 16 | huAb1VH.1/VL.1A VL | VL | | DIVMTQSPDSLAVSLGERATINCKSSQSLLNSGNQKNYLTWFQQKPGQPPKLLIYWASTRESGVPDRFSGSGSGTDFTLTISSLQAEDVAVYYCQNDYTYPLTFGQGTKLEIK |
| 10 | huAb1VH.1/VL.1A | CDR-L1 | Residues 24-40 of SEQ ID NO.: 16 | KSSQSLLNSGNQKNYLT |
| 11 | huAb1VH.1/VL.1A | CDR-L2 | Residues 56-62 of SEQ ID NO.: 16 | WASTRES |
| 12 | huAb1VH.1/VL.1A | CDR-L3 | Residues 95-103 of SEQ ID NO.: 16 | QNDYTYPLT |

TABLE 11-continued

VH and VL sequences of humanized versions of antibody 1 (huAb1)

| SEQ ID NO: | Clone | Antibody Region | Residues | Amino acid sequence |
|---|---|---|---|---|
| 15 | huAb1VH.1A/VL.1A VH | VH | | EVQLVESGGGLVKPGGSLRLSCAASGFTF SDYGMNWVRQAPGKGLEWIAYISSGRSNI YYADTVKGRFTISRDNAKNSLYLQMNSLR AEDTAVYYCARSWGYFDVWGQGTTVTVSS |
| 6 | huAb1VH.1A/VL.1A | CDR-H1 | Residues 26-35 of SEQ ID NO.: 15 | GFTFSDYGMN |
| 7 | huAb1VH.1A/VL.1A | CDR-H2 | Residues 50-66 of SEQ ID NO.: 15 | YISSGRSNIYYADTVKG |
| 8 | huAb1VH.1A/VL.1A | CDR-H3 | Residues 99-105 of SEQ ID NO.: 15 | SWGYFDV |
| 16 | huAb1VH.1A/VL.1A VL | VL | | DIVMTQSPDSLAVSLGERATINCKSSQSL LNSGNQKNYLTWFQQKPGQPPKLLIYWAS TRESGVPDRFSGSGSGTDFTLTISSLQAE DVAVYYCQNDYTYPLTFGQGTKLEIK |
| 10 | huAb1VH.1A/VL.1A | CDR-L1 | Residues 24-40 of SEQ ID NO.: 16 | KSSQSLLNSGNQKNYLT |
| 11 | huAb1VH.1A/VL.1A | CDR-L2 | Residues 56-62 of SEQ ID NO.: 16 | WASTRES |
| 12 | huAb1VH.1A/VL.1A | CDR-L3 | Residues 95-103 of SEQ ID NO.: 16 | QNDYTYPLT |

As described above, the CDRs of the humanized versions of the VH and VL regions of Ab1 were identical to the murine Ab1 antibody.

Humanization of Antagonist Anti-CD40 Antibody 3 (Ab3)

Humanized antibodies were also generated based on the variable heavy (VH) and variable light (VL) CDR sequences of Ab3. Human germline sequences were selected for constructing CDR-grafted, humanized Ab3 antibodies, where the CDR domains of the VH and VL chains of Ab3 were grafted onto different human heavy and light chain acceptor sequences. Based on the alignments with the VH and VL sequences of monoclonal antibody Ab3, the following human sequences were selected as acceptors:

1. IGHV3-69*06 and IGHJ6*01 for constructing heavy chain acceptor sequences
2. IGHV1-18*01 and IGHJ6*01 as an alternative acceptor for constructing heavy chain
3. IGKV2-29*02 and IGKJ2*01 for constructing light chain acceptor sequences
4. IGKV2-28*01 and IGKJ2*01 as an alternative acceptor for constructing light chain CDR-grafted antibodies were prepared by grafting the corresponding VH and VL CDRs of Ab3 into the acceptor sequences described in 1-4 above.

To generate humanized antibody with framework back-mutation(s), a number of framework mutations were identified and introduced into the CDR-grafted antibodies. These mutations were introduced using standard techniques, including de novo synthesis of the variable domain with the backmutation(s) and mutagenic oligonucleotide primers in polymerase chain reactions. Different combinations of mutations, including back mutations, were constructed for each of the CDR-grafted antibodies (containing the CDRs of antibody Ab3). (Note: Residue numbers for the below-mentioned mutations are based on the Kabat numbering system.).

For heavy chains Ab3, one or more of the following Vernier and VH/VL interfacing residues were back mutated: M48I, V67A, I69L. In addition, changes to Q1E were considered. The Q1E mutation was introduced in order to prevent pyroglutamate formation.

For light chains Ab3, one or more of the following Vernier and VH/VL interfacing residues were back mutated: Y36F, L46Y.

Descriptions of the variable regions of the humanized antibodies derived from murine monoclonal Ab3 are described below:

huAb3VH.1z is a CDR-grafted, humanized Ab3 VH containing IGHV1-69*06 and IGHJ6*01 framework sequences.

huAb3VH.1 is based on huAb3VH.1z with a Q1E change to prevent pyroglutamate formation huAb3VH.1A is a humanized design based on huAb3VH.1 and contains 3 additional framework backmutations: M48I, V67A, I69L.

huAb3VH.1b is an intermediate design between huAb3VH.1 and huAb3VH.1A and contains 1 proposed framework back-mutation: I69L.

huAb3VL.1 is a CDR-grafted, humanized Ab3 VL containing IGKV2-28*01 and IGKJ2*01 framework sequences.

huAb3VL.1A is a humanized design based on huAb3VL.1 and contains 2 framework back-mutations: Y36F, L46Y.

huAb3VL.1B is an intermediate design between huAb3VL.1 and huAb3VL.1A. It contains 1 proposed framework back-mutation: L46Y.

Note also that *IGHV1-69_IGHJ6 is made up of IGHV1-69*06 and IGHJ6*01 germline sequences.

The humanized variable regions were then cloned into IgG expression vectors for functional characterization of nine different humanized antibodies based on the following combinations of heavy and light chain variable regions:

A. huAb3VH.1/VL.1
B. huAb3VH.1B/VL.1
C. huAb3VH.1A/VL.1
D. huAb3VH.1/VL.1A
E. huAb3VH.1B/VL.1A
F. huAb3VH.1A/VL.1A
G. huAb3VH.1/VL.1B
H. huAb3VH.1B/VL.1B
I. huAb3VH.1A/VL.1B

The variable region and CDR amino acid sequences of the foregoing humanized antibodies are described in Table 12 below.

TABLE 12

Amino acid sequences of VH and VL regions of humanized Ab3 antibodies

| SEQ ID NO: | Clone | Antibody Region | Residues | Amino acid sequence |
|---|---|---|---|---|
| 52 | huAb3VH.1/VL.1 | VH | | EVQLVQSGAEVKKPGSSVKVSCKASGYTF TSYTMHWVRQAPGQGLEWMGYINPSSDYP NYNQKFKDRVTITADKSTSTAYMELSSLR SEDTAVYYCARWGYSFDYWGQGTTVTSS |
| 45 | huAb3VH.1/VL.1 | CDR-H1 | Residues 26-35 of SEQ ID NO.: 52 | GYTFTSYTMH |
| 46 | huAb3VH.1/VL.1 | CDR-H2 | Residues 50-66 of SEQ ID NO.: 52 | YINPSSDYPNYNQKFKD |
| 47 | huAb3VH.1/VL.1 | CDR-H3 | Residues 99-105 of SEQ ID NO.: 52 | WGYSFDY |
| 53 | huAb3VH.1/VL.1 | VL | | DIVMTQSPLSLPVTPGEPASISCRSSKSL LHSNGNTYLYWYLQKPGQSPQLLIYRMST LASGVPDRFSGSGSGTDFTLKISRVEAED VGVYYCMQHLEYPLTFGQGTKLEIK |
| 49 | huAb3VH.1/VL.1 | CDR-L1 | Residues 24-39 of SEQ ID NO.: 53 | RSSKSLLHSNGNTYLY |
| 50 | huAb3VH.1/VL.1 | CDR-L2 | Residues 55-61 of SEQ ID NO.: 53 | RMSTLAS |
| 51 | huAb3VH.1/VL.1 | CDR-L3 | Residues 94-102 of SEQ ID NO.: 53 | MQHLEYPLT |
| 54 | huAb3VH.1B/VL.1 | VH | | EVQLVQSGAEVKKPGSSVKVSCKASGYTF TSYTMHWVRQAPGQGLEWMGYINPSSDYP NYNQKFKDRVTLTADKSTSTAYMELSSLR SEDTAVYYCARWGYSFDYWGQGTTVTSS |
| 45 | huAb3VH.1B/VL.1 | CDR-H1 | Residues 26-35 of SEQ ID NO.: 54 | GYTFTSYTMH |
| 46 | huAb3VH.1B/VL.1 | CDR-H2 | Residues 50-66 of SEQ ID NO.: 54 | YINPSSDYPNYNQKFKD |
| 47 | huAb3VH.1B/VL.1 | CDR-H3 | Residues 99-105 of SEQ ID NO.: 54 | WGYSFDY |
| 53 | huAb3VH.1B/VL.1 | VL | | DIVMTQSPLSLPVTPGEPASISCRSSKSL LHSNGNTYLYWYLQKPGQSPQLLIYRMST LASGVPDRFSGSGSGTDFTLKISRVEAED VGVYYCMQHLEYPLTFGQGTKLEIK |
| 49 | huAb3VH.1B/VL.1 | CDR-L1 | Residues 24-39 of SEQ ID NO.: 53 | RSSKSLLHSNGNTYLY |
| 50 | huAb3VH.1B/VL.1 | CDR-L2 | Residues 55-61 of SEQ ID NO.: 53 | RMSTLAS |
| 51 | huAb3VH.1B/VL.1 | CDR-L3 | Residues 94-102 of SEQ ID NO.: 53 | MQHLEYPLT |
| 55 | huAb3VH.1A/VL.1 | VH | | EVQLVQSGAEVKKPGSSVKVSCKASGYTF TSYTMHWVRQAPGQGLEWIGYINPSSDYP NYNQKFKDRATLTADKSTSTAYMELSSLR SEDTAVYYCARWGYSFDYWGQGTTVTSS |
| 45 | huAb3VH.1A/VL.1 | CDR-H1 | Residues 26-35 of SEQ ID NO.: 55 | GYTFTSYTMH |
| 46 | huAb3VH.1A/VL.1 | CDR-H2 | Residues 50-66 of SEQ ID NO.: 55 | YINPSSDYPNYNQKFKD |

TABLE 12-continued

Amino acid sequences of VH and VL regions of humanized Ab3 antibodies

| SEQ ID NO: | Clone | Antibody Region | Residues | Amino acid sequence |
|---|---|---|---|---|
| 47 | huAb3VH.1A/VL.1 | CDR-H3 | Residues 99-105 of SEQ ID NO.: 55 | WGYSFDY |
| 53 | huAb3VH.1A/VL.1 | VL | | DIVMTQSPLSLPVTPGEPASISCRSSKSL LHSNGNTYLYWYLQKPGQSPQLLIYRMST LASGVPDRFSGSGSGTDFTLKISRVEAED VGVYYCMQHLEYPLTFGQGTKLEIK |
| 49 | huAb3VH.1A/VL.1 | CDR-L1 | Residues 24-39 of SEQ ID NO.: 53 | RSSKSLLHSNGNTYLY |
| 50 | huAb37VH.1A/VL.1 | CDR-L2 | Residues 55-61 of SEQ ID NO.: 53 | RMSTLAS |
| 51 | huAb3VH.1A/VL.1 | CDR-L3 | Residues 94-102 of SEQ ID NO.: 53 | MQHLEYPLT |
| 52 | huAb3VH.1/VL.1A | VL | | EVQLVQSGAEVKKPGSSVKVSCKASGYTF TSYTMHWVRQAPGQGLEWMGYINPSSDYP NYNQKFKDRVTITADKSTSTAYMELSSLR SEDTAVYYCARWGYSFDYWGQGTTVTVSS |
| 45 | huAb3VH.1/VL.1A | CDR-H1 | Residues 26-35 of SEQ ID NO.: 52 | GYTFTSYTMH |
| 46 | huAb3VH.1/VL.1A | CDR-H2 | Residues 50-66 of SEQ ID NO.: 52 | YINPSSDYPNYNQKFKD |
| 47 | huAb3VH.1/VL.1A | CDR-H3 | Residues 99-105 of SEQ ID NO.: 52 | WGYSFDY |
| 56 | huAb3VH.1/VL.1A | VL | | DIVMTQSPLSLPVTPGEPASISCRSSKSL LHSNGNTYLYWFLQKPGQSPQYLIYRMST LASGVPDRFSGSGSGTDFTLKISRVEAED VGVYYCMQHLEYPLTFGQGTKLEIK |
| 49 | huAb3VH.1/VL.1A | CDR-L1 | Residues 24-39 of SEQ ID NO.: 56 | RSSKSLLHSNGNTYLY |
| 50 | huAb3VH.1/VL.1A | CDR-L2 | Residues 55-61 of SEQ ID NO.: 56 | RMSTLAS |
| 51 | huAb3VH.1/VL.1A | CDR-L3 | Residues 94-102 of SEQ ID NO.: 56 | MQHLEYPLT |
| 54 | huAb3VH.1B/VL.1A | VH | | EVQLVQSGAEVKKPGSSVKVSCKASGYTF TSYTMHWVRQAPGQGLEWMGYINPSSDYP NYNQKFKDRVTLTADKSTSTAYMELSSLR SEDTAVYYCARWGYSFDYWGQGTTVTVSS |
| 45 | huAb3VH.1B/VL.1A | CDR-H1 | Residues 26-35 of SEQ ID NO.: 54 | GYTFTSYTMH |
| 46 | huAb3VH.1B/VL.1A | CDR-H2 | Residues 50-66 of SEQ ID NO.: 54 | YINPSSDYPNYNQKFKD |
| 47 | huAb3VH.1B/VL.1A | CDR-H3 | Residues 99-105 of SEQ ID NO.: 54 | WGYSFDY |
| 56 | huAb3VH.1B/VL.1A | VL | | DIVMTQSPLSLPVTPGEPASISCRSSKSL LHSNGNTYLYWFLQKPGQSPQYLIYRMST LASGVPDRFSGSGSGTDFTLKISRVEAED VGVYYCMQHLEYPLTFGQGTKLEIK |
| 49 | huAb3VH.1B/VL.1A | CDR-L1 | Residues 24-39 of SEQ ID NO.: 56 | RSSKSLLHSNGNTYLY |
| 50 | huAb3VH.1B/VL.1A | CDR-L2 | Residues 55-61 of SEQ ID NO.: 56 | RMSTLAS |
| 51 | huAb3VH.1B/VL.1A | CDR-L3 | Residues 94-102 of SEQ ID NO.: 56 | MQHLEYPLT |

TABLE 12-continued

Amino acid sequences of VH and VL regions of humanized Ab3 antibodies

| SEQ ID NO: | Clone | Antibody Region | Residues | Amino acid sequence |
|---|---|---|---|---|
| 55 | huAb3VH.1A/VL.1A | VH | | EVQLVQSGAEVKKPGSSVKVSCKASGYTF TSYTMHWVRQAPGQGLEWIGYINPSSDYP NYNQKFKDRATLTADKSTSTAYMELSSLR SEDTAVYYCARWGYSFDYWGQGTTVTVSS |
| 45 | huAb3VH.1A/VL.1A | CDR-H1 | Residues 26-35 of SEQ ID NO.: 55 | GYTFTSYTMH |
| 46 | huAb3VH.1A/VL.1A | CDR-H2 | Residues 50-66 of SEQ ID NO.: 55 | YINPSSDYPNYNQKFKD |
| 47 | huAb3VH.1A/VL.1A | CDR-H3 | Residues 99-105 of SEQ ID NO.: 55 | WGYSFDY |
| 56 | huAb3VH.1A/VL.1A | VL | | DIVMTQSPLSLPVTPGEPASISCRSSKSL LHSNGNTYLYWFLQKPGQSPQYLIYRMST LASGVPDRFSGSGSGTDFTLKISRVEAED VGVYYCMQHLEYPLTFGQGTKLEIK |
| 49 | huAb3VH.1A/VL.1A | CDR-L1 | Residues 24-39 of SEQ ID NO.: 56 | RSSKSLLHSNGNTYLY |
| 50 | huAb37VH.1A/VL.1A | CDR-L2 | Residues 55-61 of SEQ ID NO.: 56 | RMSTLAS |
| 51 | huAb3VH.1A/VL.1A | CDR-L3 | Residues 94-102 of SEQ ID NO.: 56 | MQHLEYPLT |
| 52 | huAb3VH.1/VL.1B | VH | | EVQLVQSGAEVKKPGSSVKVSCKASGYTF TSYTMHWVRQAPGQGLEWMGYINPSSDYP NYNQKFKDRVTITADKSTSTAYMELSSLR SEDTAVYYCARWGYSFDYWGQGTTVTVSS |
| 45 | huAb3VH.1/VL.1B | CDR-H1 | Residues 26-35 of SEQ ID NO.: 52 | GYTFTSYTMH |
| 46 | huAb3VH.1/VL.1B | CDR-H2 | Residues 50-66 of SEQ ID NO.: 52 | YINPSSDYPNYNQKFKD |
| 47 | huAb3VH.1/VL.1B | CDR-H3 | Residues 99-105 of SEQ ID NO.: 52 | WGYSFDY |
| 57 | huAb3VH.1/VL.1B | VL | | DIVMTQSPLSLPVTPGEPASISCRSSKSL LHSNGNTYLYWYLQKPGQSPQYLIYRMST LASGVPDRFSGSGSGTDFTLKISRVEAED VGVYYCMQHLEYPLTFGQGTKLEIK |
| 49 | huAb3VH.1/VL.1B | CDR-L1 | Residues 24-39 of SEQ ID NO.: 57 | RSSKSLLHSNGNTYLY |
| 50 | huAb3VH.1/VL.1B | CDR-L2 | Residues 55-61 of SEQ ID NO.: 57 | RMSTLAS |
| 51 | huAb3VH.1/VL.1B | CDR-L3 | Residues 94-102 of SEQ ID NO.: 57 | MQHLEYPLT |
| 54 | huAb3VH.1B/VL.1B | VH | | EVQLVQSGAEVKKPGSSVKVSCKASGYTF TSYTMHWVRQAPGQGLEWMGYINPSSDYP NYNQKFKDRVTLTADKSTSTAYMELSSLR SEDTAVYYCARWGYSFDYWGQGTTVTVSS |
| 45 | huAb3VH.1B/VL.1B | CDR-H1 | Residues 26-35 of SEQ ID NO.: 54 | GYTFTSYTMH |
| 46 | huAb3VH.1B/VL.1B | CDR-H2 | Residues 50-66 of SEQ ID NO.: 54 | YINPSSDYPNYNQKFKD |
| 47 | huAb3VH.1B/VL.1B | CDR-H3 | Residues 99-105 of SEQ ID NO.: 54 | WGYSFDY |
| 57 | huAb3VH.1B/VL.1B | VL | | DIVMTQSPLSLPVTPGEPASISCRSSKSL LHSNGNTYLYWYLQKPGQSPQYLIYRMST LASGVPDRFSGSGSGTDFTLKISRVEAED VGVYYCMQHLEYPLTFGQGTKLEIK |

TABLE 12-continued

Amino acid sequences of VH and VL regions of humanized Ab3 antibodies

| SEQ ID NO: | Clone | Antibody Region | Residues | Amino acid sequence |
|---|---|---|---|---|
| 49 | huAb3VH.1B/VL.1B | CDR-L1 | Residues 24-39 of SEQ ID NO.: 57 | RSSKSLLHSNGNTYLY |
| 50 | huAb3VH.1B/VL.1B | CDR-L2 | Residues 55-61 of SEQ ID NO.: 57 | RMSTLAS |
| 51 | huAb3VH.1B/VL.1B | CDR-L3 | Residues 94-102 of SEQ ID NO.: 57 | MQHLEYPLT |
| 55 | huAb3VH.1A/VL.1B | VH | | EVQLVQSGAEVKKPGSSVKVSCKASGYTF TSYTMHWVRQAPGQGLEWIGYINPSSDYP NYNQKFKDRATLTADKSTSTAYMELSSLR SEDTAVYYCARWGYSFDYWGQGTTVTVSS |
| 45 | huAb3VH.1A/VL.1B | CDR-H1 | Residues 26-35 of SEQ ID NO.: 55 | GYTFTSYTMH |
| 46 | huAb3VH.1A/VL.1B | CDR-H2 | Residues 50-66 of SEQ ID NO.: 55 | YINPSSDYPNYNQKFKD |
| 47 | huAb3VH.1A/VL.1B | CDR-H3 | Residues 99-105 of SEQ ID NO.: 55 | WGYSFDY |
| 57 | huAb3VH.1A/VL.1B | VL | | DIVMTQSPLSLPVTPGEPASISCRSSKSL LHSNGNTYLYWYLQKPGQSPQYLIYRMST LASGVPDRFSGSGSGTDFTLKISRVEAED VGVYYCMQHLEYPLTFGQGTKLEIK |
| 49 | huAb3VH.1A/VL.1B | CDR-L1 | Residues 24-39 of SEQ ID NO.: 57 | RSSKSLLHSNGNTYLY |
| 50 | huAb37VH.1A/VL.1B | CDR-L2 | Residues 55-61 of SEQ ID NO.: 57 | RMSTLAS |
| 51 | huAb3VH.1A/VL.1B | CDR-L3 | Residues 94-102 of SEQ ID NO.: 57 | MQHLEYPLT |

As described above, the CDRs of the humanized versions of the VH and VL regions of Ab3 were identical to the murine Ab3 antibody.

As Ab3 did not bind to cyno CD40 (see Example 1), humanized versions of Ab1 were selected for further analysis.

Example 3

Modification of VL CDR1 of Humanized Ab1 Antibodies

Examination of the humanized Ab1 VH and VL antibody sequences described above identified a potential deamidation sequence motif (an "NS" motif) exposed in the CDR1 of the light chain. The "NS" motif site that was identified can lead to deamidation and hydrolysis, and lead to a succinimide-intermediate and aspartyl-ASP or iso-ASP. Thus, the sequence motif was engineered out of the humanized Ab1 VL CDR1 sequences. Removing the "NS" motif would allow for improved antibody manufacturing.

The further engineering of humanized Ab1 resulted in six different antibodies. Notably, four retained the antagonist activity, while two became agonist antibodies (huAb1v4 and huAb1v3). As shown in Table 14, huAb1v4 and huAb1v3 showed agonist activity as determined by a huCD40 reporter assay, while displaying no antagonist activity as determined in a Jurkat/Reporter assay. The VH and VL amino acid sequences, as well as the CDRs, of the variant humanized Ab1 antibodies (huAb1v1 to huAb1v6) are described below in Table 13.

TABLE 13

Humanized Ab1 antibody variant (huAb1v#) VH and VL amino acid sequence

| SEQ ID NO.: | Clone | Antibody Region | Residues | Amino Acid Sequence |
|---|---|---|---|---|
| 13 | huAb1v3 | VH | | EVQLVESGGGLVKPGGSLRLSCAASGFTF SDYGMNWVRQAPGKGLEWVSYISSGRSNI YYADTVKGRFTISRDNAKNSLYLQMNSLR AEDTAVYYCARSWGYFDVWGQGTTVTVSS |
| 6 | huAb1v3 | CDR-H1 | Residues 26-35 of SEQ ID NO.: 13 | GFTFSDYGMN |

TABLE 13-continued

Humanized Ab1 antibody variant (huAb1v#)
VH and VL amino acid sequence

| SEQ ID NO.: | Clone | Antibody Region | Residues | Amino Acid Sequence |
|---|---|---|---|---|
| 7 | huAb1v3 | CDR-H2 | Residues 50-66 of SEQ ID NO.: 13 | YISSGRSNIYYADTVKG |
| 8 | huAb1v3 | CDR-H3 | Residues 99-105 of SEQ ID NO.: 13 | SWGYFDV |
| 43 | huAb1v3 | VL | | DIVMTQSPDSLAVSLGERATINCKSSQSL LNLGNQKNYLTWFQQKPGQPPKLLIYWAS TRESGVPDRFSGSGSGTDFTLTISSLQAE DVAVYYCQNDYTYPLTFGQGTKLEIK |
| 17 | huAb1v3 | CDR-L1 | Residues 24-40 of SEQ ID NO.: 43 | KSSQSLLNLGNQKNYLT |
| 11 | huAb1v3 | CDR-L2 | Residues 56-62 of SEQ ID NO.: 43 | WASTRES |
| 12 | huAb1v3 | CDR-L3 | Residues 95-103 of SEQ ID NO.: 43 | QNDYTYPLT |
| 15 | huAb1v4 | VH | | EVQLVESGGGLVKPGGSLRLSCAASGFTF SDYGMNWVRQAPGKGLEWIAYISSGRSNI YYADTVKGRFTISRDNAKNSLYLQMNSLR AEDTAVYYCARSWGYFDVWGQGTTVTVSS |
| 6 | huAb1v4 | CDR-H1 | Residues 26-35 of SEQ ID NO.: 15 | GFTFSDYGMN |
| 7 | huAb1v4 | CDR-H2 | Residues 50-66 of SEQ ID NO.: 15 | YISSGRSNIYYADTVKG |
| 8 | huAb1v4 | CDR-H3 | Residues 99-105 of SEQ ID NO.: 15 | SWGYFDV |
| 77 | huAb1v4 | VL | | DIVMTQSPDSLAVSLGERATINCKSSQSL LNPGNQKNYLTWFQQKPGQPPKLLIYWAS TRESGVPDRFSGSGSGTDFTLTISSLQAE DVAVYYCQNDYTYPLTFGQGTKLEIK |
| 74 | huAb1v4 | CDR-L1 | Residues 24-40 of SEQ ID NO.: 77 | KSSQSLLNPGNQKNYLT |
| 11 | huAb1v4 | CDR-L2 | Residues 56-62 of SEQ ID NO.: 77 | WASTRES |
| 12 | huAb1v4 | CDR-L3 | Residues 95-103 of SEQ ID NO.: 77 | QNDYTYPLT |
| 15 | huAb1v5 | VH | | EVQLVESGGGLVKPGGSLRLSCAASGFTF SDYGMNWVRQAPGKGLEWIAYISSGRSNI YYADTVKGRFTISRDNAKNSLYLQMNSLR AEDTAVYYCARSWGYFDVWGQGTTVTVSS |
| 6 | huAb1v5 | CDR-H1 | Residues 26-35 of SEQ ID NO.: 5 | GFTFSDYGMN |
| 7 | huAb1v5 | CDR-H2 | Residues 50-66 of SEQ ID NO.: 15 | YISSGRSNIYYADTVKG |
| 8 | huAb1v5 | CDR-H3 | Residues 99-105 of SEQ ID NO.: 15 | SWGYFDV |
| 18 | huAb1v5 | VL | | DIVMTQSPDSLAVSLGERATINCKSSQSL LNTGNQKNYLTWFQQKPGQPPKLLIYWAS TRESGVPDRFSGSGSGTDFTLTISSLQAE DVAVYYCQNDYTYPLTFGQGTKLEIK |
| 19 | huAb1v5 | CDR-L1 | Residues 24-40 of SEQ ID NO.: 18 | KSSQSLLNTGNQKNYLT |
| 11 | huAb1v5 | CDR-L2 | Residues 56-62 of SEQ ID NO.: 18 | WASTRES |

TABLE 13-continued

Humanized Ab1 antibody variant (huAb1v#)
VH and VL amino acid sequence

| SEQ ID NO.: | Clone | Antibody Region | Residues | Amino Acid Sequence |
|---|---|---|---|---|
| 12 | huAb1v5 | CDR-L3 | Residues 95-103 of SEQ ID NO.: 18 | QNDYTYPLT |
| 15 | huAb1v6 | VH | | EVQLVESGGGLVKPGGSLRLSCAASGFTF SDYGMNWVRQAPGKGLEWIAYISSGRSNI YYADTVKGRFTISRDNAKNSLYLQMNSLR AEDTAVYYCARSWGYFDVWGQGTTVTVSS |
| 6 | huAb1v6 | CDR-H1 | Residues 26-35 of SEQ ID NO.: 15 | GFTFSDYGMN |
| 7 | huAb1v6 | CDR-H2 | Residues 50-66 of SEQ ID NO.: 15 | YISSGRSNIYYADTVKG |
| 8 | huAb1v6 | CDR-H3 | Residues 99-105 of SEQ ID NO.: 15 | SWGYFDV |
| 43 | huAb1v6 | VL | | DIVMTQSPDSLAVSLGERATINCKSSQSL LNLGNQKNYLTWFQQKPGQPPKLLIYWAS TRESGVPDRFSGSGSGTDFTLTISSLQAE DVAVYYCQNDYTYPLTFGQGTKLEIK |
| 17 | huAb1v6 | CDR-L1 | Residues 24-40 of SEQ ID NO.: 43 | KSSQSLLNLGNQKNYLT |
| 11 | huAb1v6 | CDR-L2 | Residues 56-62 of SEQ ID NO.: 43 | WASTRES |
| 12 | huAb1v6 | CDR-L3 | Residues 95-103 of SEQ ID NO.: 43 | QNDYTYPLT |
| 15 | huAb1v1 | VH | | EVQLVESGGGLVKPGGSLRLSCAASGFTF SDYGMNWVRQAPGKGLEWIAYISSGRSNI YYADTVKGRFTISRDNAKNSLYLQMNSLR AEDTAVYYCARSWGYFDVWGQGTTVTVSS |
| 6 | huAb1v1 | CDR-H1 | Residues 26-35 of SEQ ID NO.: 15 | GFTFSDYGMN |
| 7 | huAb1v1 | CDR-H2 | Residues 50-66 of SEQ ID NO.: 15 | YISSGRSNIYYADTVKG |
| 8 | huAb1v1 | CDR-H3 | Residues 99-105 of SEQ ID NO.: 15 | SWGYFDV |
| 20 | huAb1v1 | VL | | DIVMTQSPDSLAVSLGERATINCKSSQSL LNRGNQKNYLTWFQQKPGQPPKLLIYWAS TRESGVPDRFSGSGSGTDFTLTISSLQAE DVAVYYCQNDYTYPLTFGQGTKLEIK |
| 21 | huAb1v1 | CDR-L1 | Residues 24-40 of SEQ ID NO.: 20 | KSSQSLLNRGNQKNYLT |
| 11 | huAb1v1 | CDR-L2 | Residues 56-62 of SEQ ID NO.: 20 | WASTRES |
| 12 | huAb1v1 | CDR-L3 | Residues 95-103 of SEQ ID NO.: 20 | QNDYTYPLT |
| 13 | huAb1v2 | VH | | EVQLVESGGGLVKPGGSLRLSCAASGFTF SDYGMNWVRQAPGKGLEWVSYISSGRSNI YYADTVKGRFTISRDNAKNSLYLQMNSLR AEDTAVYYCARSWGYFDVWGQGTTVTVSS |
| 6 | huAb1v2 | CDR-H1 | Residues 26-35 of SEQ ID NO.: 13 | GFTFSDYGMN |
| 7 | huAb1v2 | CDR-H2 | Residues 50-66 of SEQ ID NO.: 13 | YISSGRSNIYYADTVKG |
| 8 | huAb1v2 | CDR-H3 | Residues 99-105 of SEQ ID NO.: 13 | SWGYFDV |

TABLE 13-continued

Humanized Ab1 antibody variant (huAb1v#)
VH and VL amino acid sequence

| SEQ ID NO.: | Clone | Antibody Region | Residues | Amino Acid Sequence |
|---|---|---|---|---|
| 18 | huAb1v2 | VL | | DIVMTQSPDSLAVSLGERATINCKSSQSL LNTGNQKNYLTWFQQKPGQPPKLLIYWAS TRESGVPDRFSGSGSGTDFTLTISSLQAE DVAVYYCQNDYTYPLTFGQGTKLEIK |
| 19 | huAb1v2 | CDR-L1 | Residues 24-40 of SEQ ID NO.: 18 | KSSQSLLNTGNQKNYLT |
| 11 | huAb1v2 | CDR-L2 | Residues 56-62 of SEQ ID NO.: 18 | WASTRES |
| 12 | huAb1v2 | CDR-L3 | Residues 95-103 of SEQ ID NO.: 18 | QNDYTYPLT |

In addition to the modification of the "NS" motif in the VL CDR1, variants huAb1v2 and huAb1v3 described above in Table 13 have additional framework mutations in their VH domains.

Table 14 below provides a summary of the variant binding, agonist, and antagonist activities. Descriptions of the assays can be found above in Example 2. The "NS" motif that was mutated in the VL CDR1 is underlined in Table 14 below. As described in Table 14, antibodies huAb1v4 (containing a "P" mutation in the VL CDR1 domain) and huAb1v3 (containing a "L" mutation in the VL CDR1 domain and framework mutations within the VH region) exhibited agonist activity despite being derived from a parent antibody having antagonist activity.

Example 4

Engineering of HC CDR2 of Anti-CD40 Antibody huAb1v1

From the variants described in Example 3, antibody huAb1v1 was selected for further analysis. In order to further improve the potency of this antibody, variants of the huAb1v1 heavy chain (HC) were produced containing mutations within the HC CDR2 domain. Seventeen additional variants were made (referred to as huAb1v1CDR2v1 to v17). The variant HC regions were paired with the huAb1v1 LC (SEQ ID NO: 20) for activity studies to determine agonist and antagonist activity. Seventeen variant heavy chains were made, and in vitro activity studies showed that generally the variants retained their antagonistic activity and diverse potency compared to huAb1v1. Table 15 shows that

TABLE 14

Sequence and Functional Summary for Variant Humanized Antibodies

| Humanized 163-2.1F2.2B5 variants | VL LCDR1 Sequence (KSSQSLL<u>NS</u>GNQKNYLT (SEQ ID NO: 10)) | Blocking of sCD40L | Agonist: huCD40 reporter assay IC50 nM | Antagonist: Jurkat/ Reporter assay IC50 nM |
|---|---|---|---|---|
| huAb1v4 | KSSQSLL<u>NP</u>GNQKNYLT (SEQ ID NO: 74) | Yes | 49 | No |
| huAb1v6 | KSSQSLL<u>NL</u>GNQKNYLT (SEQ ID NO: 17) | Yes | No | 85.0 |
| huAb1v1 | KSSQSLL<u>NR</u>GNQKNYLT (SEQ ID NO: 21) | Yes | No | 55 |
| huAb1v2* | KSSQSLL<u>NT</u>GNQKNYLT (SEQ ID NO: 19) | Yes | No | >100 |
| huAb1v5 | KSSQSLL<u>NT</u>GNQKNYLT (SEQ ID NO: 19) | Yes | No | >100 |
| huAb1v3* | KSSQSLL<u>NL</u>GNQKNYLT (SEQ ID NO: 17) | Yes | 79 | No |

*Additional framework differences in VH

Humanized anti-CD40 antibody huAb1v1 was selected for further study and improvement.

while the antibody variants maintained antagonistic activity, the potency of each variant varied.

TABLE 15

Functional Summary for huAb1v1 CDR2 HC variants.

| Engineered huAb1v1CDR2 variants | Antagonist: Jurkat/Reporter assay (IC50 nM) |
| --- | --- |
| huAb1v1CDR2v17 | 503.8 |
| huAb1v1CDR2v16 | 30.15 |
| huAb1v1CDR2v15 | 339.7 |
| huAb1v1CDR2v14 | 21.86 |
| huAb1v1CDR2v13 | 62.44 |
| huAb1v1CDR2v12 | 236.1 |
| huAb1v1CDR2v11 | >1000 |
| huAb1v1CDR2v10 | 23.04 |
| huAb1v1CDR2v9 | 7.06 |
| huAb1v1CDR2v8 | >1000 |
| huAb1v1CDR2v7 | 2.69 |
| huAb1v1CDR2v6 | >1000 |
| huAb1v1CDR2v5 | >1000 |
| huAb1v1CDR2v4 | 563.4 |
| huAb1v1CDR2v3 | 218.7 |
| huAb1v1CDR2v2 | >1000 |
| huAb1v1CDR2v1 | >1000 |

All huAb1v1 HC variants were mutated in position S55, as described below in Table 16 (position 55 is underlined).

TABLE 16

Amino Acid Sequences of Additional VH Regions (Variants of huAb1v1VH)

| SEQ ID NO: | Clone | VH |
| --- | --- | --- |
| 15 | huAb1v1 | EVQLVESGGGLVKPGGSLRLSCAASGFTFS DYGMNWVRQAPGKGLEWIAYISSGRSNIYY ADTVKGRFTISRDNAKNSLYLQMNSLRAED TAVYYCARSWGYFDVWGQGTTVTVSS |
| 22 | huAb1v1CDR2v1 | EVQLVESGGGLVKPGGSLRLSCAASGFTFS DYGMNWVRQAPGKGLEWIAYISSGRTNIYY ADTVKGRFTISRDNAKNSLYLQMNSLRAED TAVYYCARSWGYFDVWGQGTTVTVSS |
| 23 | huAb1v1CDR2v2 | EVQLVESGGGLVKPGGSLRLSCAASGFTFS DYGMNWVRQAPGKGLEWIAYISSGRDNIYY ADTVKGRFTISRDNAKNSLYLQMNSLRAED TAVYYCARSWGYFDVWGQGTTVTVSS |
| 24 | huAb1v1CDR2v3 | EVQLVESGGGLVKPGGSLRLSCAASGFTFS DYGMNWVRQAPGKGLEWIAYISSGRENIYY ADTVKGRFTISRDNAKNSLYLQMNSLRAED TAVYYCARSWGYFDVWGQGTTVTVSS |
| 25 | huAb1v1CDR2v4 | EVQLVESGGGLVKPGGSLRLSCAASGFTFS DYGMNWVRQAPGKGLEWIAYISSGRRNIYY ADTVKGRFTISRDNAKNSLYLQMNSLRAED TAVYYCARSWGYFDVWGQGTTVTVSS |
| 26 | huAb1v1CDR2v5 | EVQLVESGGGLVKPGGSLRLSCAASGFTFS DYGMNWVRQAPGKGLEWIAYISSGRVNIYY ADTVKGRFTISRDNAKNSLYLQMNSLRAED TAVYYCARSWGYFDVWGQGTTVTVSS |
| 27 | huAb1v1CDR2v6 | EVQLVESGGGLVKPGGSLRLSCAASGFTFS DYGMNWVRQAPGKGLEWIAYISSGRLNIYY ADTVKGRFTISRDNAKNSLYLQMNSLRAED TAVYYCARSWGYFDVWGQGTTVTVSS |
| 28 | huAb1v1CDR2v7 | EVQLVESGGGLVKPGGSLRLSCAASGFTFS DYGMNWVRQAPGKGLEWIAYISSGRGNIYY ADTVKGRFTISRDNAKNSLYLQMNSLRAED TAVYYCARSWGYFDVWGQGTTVTVSS |
| 29 | huAb1v1CDR2v8 | EVQLVESGGGLVKPGGSLRLSCAASGFTFS DYGMNWVRQAPGKGLEWIAYISSGRINIYY ADTVKGRFTISRDNAKNSLYLQMNSLRAED TAVYYCARSWGYFDVWGQGTTVTVSS |
| 30 | huAb1v1CDR2v9 | EVQLVESGGGLVKPGGSLRLSCAASGFTFS DYGMNWVRQAPGKGLEWIAYISSGRQNIYY ADTVKGRFTISRDNAKNSLYLQMNSLRAED TAVYYCARSWGYFDVWGQGTTVTVSS |
| 31 | huAb1v1CDR2v10 | EVQLVESGGGLVKPGGSLRLSCAASGFTFS DYGMNWVRQAPGKGLEWIAYISSGRWNIYY ADTVKGRFTISRDNAKNSLYLQMNSLRAED TAVYYCARSWGYFDVWGQGTTVTVSS |
| 32 | huAb1v1CDR2v11 | EVQLVESGGGLVKPGGSLRLSCAASGFTFS DYGMNWVRQAPGKGLEWIAYISSGRMNIYY ADTVKGRFTISRDNAKNSLYLQMNSLRAED TAVYYCARSWGYFDVWGQGTTVTVSS |
| 33 | huAb1v1CDR2v12 | EVQLVESGGGLVKPGGSLRLSCAASGFTFS DYGMNWVRQAPGKGLEWIAYISSGRKNIYY ADTVKGRFTISRDNAKNSLYLQMNSLRAED TAVYYCARSWGYFDVWGQGTTVTVSS |
| 34 | huAb1v1CDR2v13 | EVQLVESGGGLVKPGGSLRLSCAASGFTFS DYGMNWVRQAPGKGLEWIAYISSGRHNIYY ADTVKGRFTISRDNAKNSLYLQMNSLRAED TAVYYCARSWGYFDVWGQGTTVTVSS |
| 35 | huAb1v1CDR2v14 | EVQLVESGGGLVKPGGSLRLSCAASGFTFS DYGMNWVRQAPGKGLEWIAYISSGRFNIYY ADTVKGRFTISRDNAKNSLYLQMNSLRAED TAVYYCARSWGYFDVWGQGTTVTVSS |
| 36 | huAb1v1CDR2v15 | EVQLVESGGGLVKPGGSLRLSCAASGFTFS DYGMNWVRQAPGKGLEWIAYISSGRYNIYY ADTVKGRFTISRDNAKNSLYLQMNSLRAED TAVYYCARSWGYFDVWGQGTTVTVSS |
| 37 | huAb1v1CDR2v16 | EVQLVESGGGLVKPGGSLRLSCAASGFTFS DYGMNWVRQAPGKGLEWIAYISSGRANIYY ADTVKGRFTISRDNAKNSLYLQMNSLRAED TAVYYCARSWGYFDVWGQGTTVTVSS |
| 38 | huAb1v1CDR2v17 | EVQLVESGGGLVKPGGSLRLSCAASGFTFS DYGMNWVRQAPGKGLEWIAYISSGRPNIYY ADTVKGRFTISRDNAKNSLYLQMNSLRAED TAVYYCARSWGYFDVWGQGTTVTVSS |

Table 17 below provides a comparison of the HC CDR2 regions of the above-described huAb1v1 variants, after engineering of the S55 residue (in bold/underlined). The VH CDR2 region of huAb1v1 corresponds to amino acid residues 50-66 of SEQ ID NO:15.

TABLE 17

Alignment of huAb1v1 HC CDR2 variants at position 55

| Variant VH CDR2 | HC CDR2 SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| huAb1v1 | 7 | Y | I | S | S | G | R | S | N | I | Y | Y | A | D | T | V | K | G |
| huAb1v1CDR2v1 | 58 | Y | I | S | S | G | R | T | N | I | Y | Y | A | D | T | V | K | G |
| huAb1v1CDR2v2 | 59 | Y | I | S | S | G | R | D | N | I | Y | Y | A | D | T | V | K | G |
| huAb1v1CDR2v3 | 60 | Y | I | S | S | G | R | E | N | I | Y | Y | A | D | T | V | K | G |
| huAb1v1CDR2v4 | 61 | Y | I | S | S | G | R | R | N | I | Y | Y | A | D | T | V | K | G |
| huAb1v1CDR2v5 | 62 | Y | I | S | S | G | R | V | N | I | Y | Y | A | D | T | V | K | G |
| huAb1v1CDR2v6 | 63 | Y | I | S | S | G | R | L | N | I | Y | Y | A | D | T | V | K | G |
| *huAb1v1CDR2v7* | 42 | *Y* | *I* | *S* | *S* | *G* | *R* | G | *N* | *I* | *Y* | *Y* | *A* | *D* | *T* | *V* | *K* | *G* |
| huAb1v1CDR2v8 | 64 | Y | I | S | S | G | R | I | N | I | Y | Y | A | D | T | V | K | G |
| huAb1v1CDR2v9 | 65 | Y | I | S | S | G | R | Q | N | I | Y | Y | A | D | T | V | K | G |
| huAb1v1CDR2v10 | 66 | Y | I | S | S | G | R | W | N | I | Y | Y | A | D | T | V | K | G |
| huAb1v1CDR2v11 | 67 | Y | I | S | S | G | R | M | N | I | Y | Y | A | D | T | V | K | G |
| huAb1v1CDR2v12 | 68 | Y | I | S | S | G | R | K | N | I | Y | Y | A | D | T | V | K | G |
| huAb1v1CDR2v13 | 69 | Y | I | S | S | G | R | H | N | I | Y | Y | A | D | T | V | K | G |
| huAb1v1CDR2v14 | 70 | Y | I | S | S | G | R | F | N | I | Y | Y | A | D | T | V | K | G |
| huAb1v1CDR2v15 | 71 | Y | I | S | S | G | R | Y | N | I | Y | Y | A | D | T | V | K | G |
| huAb1v1CDR2v16 | 72 | Y | I | S | S | G | R | A | N | I | Y | Y | A | D | T | V | K | G |
| huAb1v1CDR2v17 | 73 | Y | I | S | S | G | R | P | N | I | Y | Y | A | D | T | V | K | G |

Heavy chain variable region huAb1v1CDR2v7 was selected as having particularly advantageous properties over the other variants that were produced and described above in Tables 15-17. Notably, huAb1v1CDR2v7 has a mutation in its HC CDR2 identified as S55G. Specifically, an antibody containing the VL of antibody huAb1v1 (SEQ ID NO: 20; see Table 13) and VH huAb1v1CDR2v7 was determined to have a 20× increased antagonistic activity in comparison to antibody huAb1v1.

The VL of huAbv1 and the VH of huAb1v1CDR2v7 were expressed in the context of two different human IgG1 constant regions. One IgG1 constant region was selected because its effector function was diminished (hCg1,z,non-a L234A, L235A or LALA) and the other IgG1 constant region was selected because both its effector function was diminished and it had a set of mutations that enhance FcRn binding (hCg1,z,non-a L234A, L235A-T250Q, M428L or LALA-QL). Tables 18 and 19 below provide the amino acid sequence information for the heavy and light chains of anti-human CD40 antibodies Ab101 (VL huAbv1/VH huAb1v1CDR2v7/hCg1/k-LALA) and Ab102 (VL huAbv1/VH huAb1v1CDR2v7/hCg1/k-LALA-QL) Amino acid residues of individual CDRs of each VH or VL sequence are indicated in bold. Constant regions are underlined in Table 19.

TABLE 18

VH and VL amino acid sequences of Ab101 and Ab102 anti-hCD40 antibodies.

| SEQ ID NO | Protein region | | Sequence |
|---|---|---|---|
| 28 | Ab101 | VH | EVQLVESGGGLVKPGGSLRLSCAASGFTFS DYGMNWVRQAPGKGLEWIAYISSGRGNIYY ADTVKGRFTISRDNAKNSLYLQMNSLRAED TAVYYCARSWGYFDVWGQGTTVTVSS |
| 6 | | CDR-H1 Residues 26-35 of SEQ ID NO.: 28 | GFTFSDYGMN |
| 42 | | CDR-H2 Residues 50-66 of SEQ ID NO.: 28 | YISSGRGNIYYADTVKG |

TABLE 18-continued

VH and VL amino acid sequences of Ab101 and Ab102 anti-hCD40 antibodies.

| SEQ ID NO | | Protein region | | Sequence |
|---|---|---|---|---|
| 8 | | CDR-H3 | Residues 99-105 of SEQ ID NO.: 28 | SWGYFDV |
| 20 | Ab101 | VL | | DIVMTQSPDSLAVSLGERATINCKSSQSLLNRGNQKNYLTWFQQKPGQPPKLLIYWASTRESGVPDRFSGSGSGTDFTLTISSLQAEDVAVYYCQNDYTYPLTFGQGTKLEIK |
| 21 | | CDR-L1 | Residues 24-40 of SEQ ID NO.: 20 | KSSQSLLNRGNQKNYLT |
| 11 | | CDR-L2 | Residues 56-62 of SEQ ID NO.: 20 | WASTRES |
| 12 | | CDR-L3 | Residues 85-93 of SEQ ID NO.: 20 | QNDYTYPLT |
| 28 | Ab102 | VH | | EVQLVESGGGLVKPGGSLRLSCAASGFTFSDYGMNWVRQAPGKGLEWIAYISSGRGNIYYADTVKGRFTISRDNAKNSLYLQMNSLRAEDTAVYYCARSWGYFDVWGQGTTVTVSS |
| 6 | | CDR-H1 | Residues 26-35 of SEQ ID NO.: 28 | GFTFSDYGMN |
| 42 | | CDR-H2 | Residues 50-66 of SEQ ID NO.: 28 | YISSGRGNIYYADTVKG |
| 8 | | CDR-H3 | Residues 99-105 of SEQ ID NO.: 28 | SWGYFDV |
| 20 | Ab102 | VL | | DIVMTQSPDSLAVSLGERATINCKSSQSLLNRGNQKNYLTWFQQKPGQPPKLLIYWASTRESGVPDRFSGSGSGTDFTLTISSLQAEDVAVYYCQNDYTYPLTFGQGTKLEIK |
| 21 | | CDR-L1 | Residues 24-40 of SEQ ID NO.: 20 | KSSQSLLNRGNQKNYLT |
| 11 | | CDR-L2 | Residues 56-62 of SEQ ID NO.: 20 | WASTRES |
| 12 | | CDR-L3 | Residues 85-93 of SEQ ID NO.: 20 | QNDYTYPLT |

TABLE 19

Amino acid sequences of Heavy Chain (HC) and Light Chain (LC) Ab101 and Ab102 anti-hCD40 antibodies.

| Clone | SEQ ID NO: | VH |
|---|---|---|
| Ab101-HC | 39 | EVQLVESGGGLVKPGGSLRLSCAASGFTFSDYGMNWVRQAPGKGLEWIAYISSGRGNIYYADTVKGRFTISRDNAKNSLYLQMNSLRAEDTAVYYCARSWGYFDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| Ab101-LC | 40 | DIVMTQSPDSLAVSLGERATINCKSSQSLLNRGNQKNYLTWFQQKPGQPPKLLIYWASTRESGVPDRFSGSGSGTDFTLTISSLQAEDVAVYYCQNDYTYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Ab102-HC | 41 | EVQLVESGGGLVKPGGSLRLSCAASGFTFSDYGMNWVRQAPGKGLEWIAYISSGRGNIYYADTVKGRFTISRDNAKNSLYLQMNSLRAEDTAVYYCARSWGYFDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDQLMISRTPEVTCVVVDVSHEDPEVKFNWYVDGVEVHNAKTKPREEQYNSTYRVVSVLTVLHQDWLNGKEYKCKVSNKALPAPIEKTISKAK |

TABLE 19-continued

Amino acid sequences of Heavy Chain (HC) and
Light Chain (LC) Ab101 and Ab102 anti-hCD40
antibodies.

| Clone | SEQ ID NO: | VH |
|---|---|---|
| | | GQPREPQVYTLPPSREEMTKNQVSLTCLVKGFYP SDIAVEWESNGQPENNYKTTPPVLDSDGSFFLYSK LTVDKSRWQQGNVFSCSVLHEALHNHYTQKSLSL SPGK |
| Ab102-LC | 40 | DIVMTQSPDSLAVSLGERATINCKSSQSLLNRGN QKNYLTWFQQKPGQPPKLLIYWASTRESGVPDR FSGSGSGTDFTLTISSLQAEDVAVYYCQNDYTYP LTFGQGTKLEIKRTVAAPSVFIFPPSDEQLKSGTAS VVCLLNNFYPREAKVQWKVDNALQSGNSQESVT EQDSKDSTYSLSSTLTLSKADYEKHKVYACEVTH QGLSSPVTKSFNRGEC |

Example 5

Functional Characterization of Humanized Antagonist Anti-hCD40 Antibodies Ab101 and Ab102

In Vitro Analysis

Humanized anti-CD40 antibodies Ab101 and Ab102 both showed antagonist activity similar to the findings in the reporter assay described in Example 1. Since residual agonist activity is related to potential risks, a B cell agonist assay was developed. In this assay, the antibodies are assessed for inhibition of CD86 upregulation in human B cells. Human B cells constitutively express CD40 and signaling through CD40 leads to activation of B cells as measured by upregulation of CD86 on the surface. B cells were activated with low dose anti-IgM and IL4 and CD40 antagonist antibodies were added. Enhancement of B cell activation was measured as upregulation of CD86, which was observed in the presence of agonist CD40 but not antagonist CD40 Ab suggesting undetectable agonist activity of lead candidate in vitro. To measure antagonist activity, primary human B cells were cultured with CD40L-expressing human T cell line that leads to B cell activation and upregulation of CD86 expression via CD40/CD40L interaction. Ability of antagonist CD40 to inhibit CD86 upregulation of primary human B cells was measured and showed strong antagonist activity of anti-CD40 antibody Ab101, as shown in FIG. 2B. FIG. 2A shows that antibody Ab101 does not have agonist activity. Notably, as described in FIG. 2B, antibody Ab101 had an $IC_{50}$ value of 1.337 in comparison to antagonist antibody Blb (Boehringer Ingelheim) which had an $IC_{50}$ value of 4.213 and agonist antibody AD11 (Astellas) which had an $IC_{50}$ value of 0.1906. Thus, antibody Ab101 (and Ab102 given the identical variable regions) is a strong antagonist of CD40 and shows no substantial in vitro agonist activity.

In Vivo Analysis

In order to test the in vivo activity of antibody Ab101, a model of human antibody generation and B cell survival was established. Briefly, when human PBMCs isolated from healthy donors were transferred into immunocompromised scid mice, the generation of human IgG in response to mouse antigens was measurable 14 days later. Additionally, FACS analysis of splenocytes from these mice indicated human B cell engraftment and survival. An antigen specific response was measured by including a challenge with tetanus toxoid (TetTox) vaccine and measuring anti-TetTox specific IgG (Naito, 2000; Jeurissen, 2004).

Figure 3A:
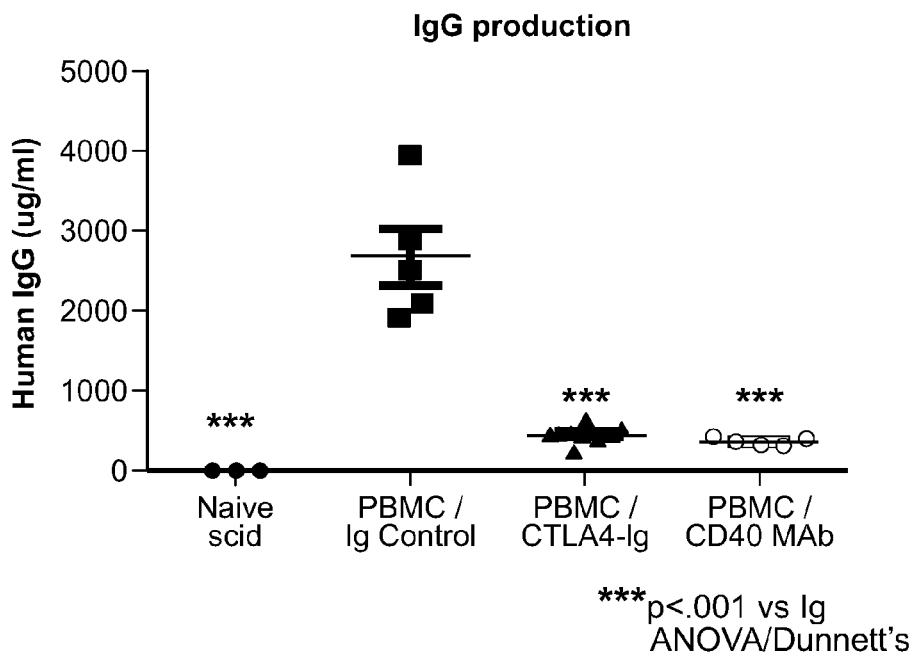
FIGS. 3A and 3B graphically depict IgG production in huscid mice who have received human PBMCs in combination with an Ig control, a CTLA4-Ig fusion, or the Ab101 antibody.
Figure 3B:
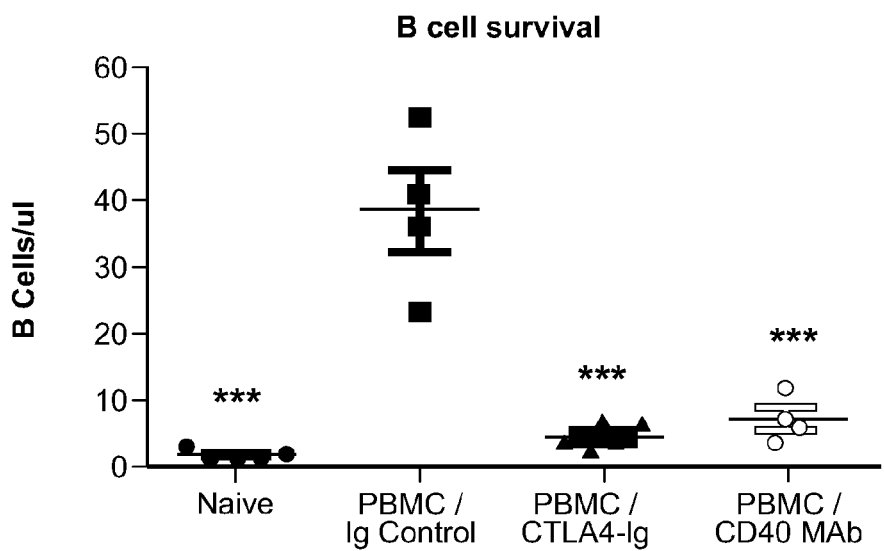

Treatment of these huscid mice with weekly doses of anti-human CD40 (Ab101, 5 mg/kg IP) resulted in >85% inhibition of human IgG production (FIG. 3A) and B cell survival (FIG. 3B), clearly demonstrating the antibody is active in vivo. Specifically, FIG. 3A shows that antibody Ab101 was able to inhibit IgG production in comparison to the Ig control, and FIG. 3B indicates that administration of antibody Ab101 in the above huscid model inhibited B cell survival.

Example 6

Epitope Analysis of Fab Ab102

Using Fab Ab102, crystallography studies were performed to determine the epitope to which Fab Ab101 binds. As described above, the VH and VL sequences of antibodies Ab101 and Ab102 are the same, and, therefore, the use of Fab Ab102 in the following crystal structure study is representative of the binding features of both antibodies Ab101 and Ab102.

Crystal structures were determined for Ab102 Fab alone and for Ab101 Fab complexed to CD40 antigen. Crystals were obtained and data was collected at the IMCA-CAT 17ID beamline. A crystal structure of Ab102 Fab was solved to 1.74 Å resolution and the Ab102 Fab/CD40 complex structure was solved to 2.84 Å resolution. The crystal structures provided the identification of the 3D conformational epitope of Ab102 Fab.

Identification of 3D Conformational Epitope of Ab102 Fab

The contacts between Ab102 Fab and CD40 involve both critical hydrogen bond and hydrophobic interactions which stabilize the interface. A list of molecular contacts (measuring under 4.0 Å) were generated using the program NCONT in the CCP4 suite of programs. The contacts were measured between the two separate crystallographic CD40 monomers and the corresponding bound light and heavy chains of the Ab102 Fab. Additional contacts were observed between the Ab102 Fab and a crystallographic CD40 dimer (the dimer created by crystal contacts). Based on this information the epitope of Ab102 Fab binding comprises of the topographical region defined by Cys62-Phe67, Gln79-Cys83, Arg90-Thr99, Thr24-Cys37 of CD40.

Materials and Methods

Preparation and Purification of CD40 Antigen:

A DNA sequence encoding the human CD40 extracellular domain (amino acids 1-193) was cloned into pHybE vector followed by an in-frame C-terminal Tev protease cleavage site and hexahistidine tag (SEQ ID NO: 115). The plasmid was transfected into HEK293 6e cells (MRL) at 1×10e6 cells/ml using the transfection reagent Polyethylenimine (PEI, Polysciences Inc) at a PEI:DNA ratio of 4:1. The transfected cell culture was fed with tryptone-N1 (to 0.5%) at 24 h post-transfection. On day 7 post-transfection, the transfected cell culture was cleared by centrifugation followed by filtration through 0.2 u PES filter (Corning). Cleared medium was buffer exchanged to PBS, pH 7.4 using a Kvick TFF system equipped with 10 kDa membranes (GE Healthcare) and loaded on a 5 ml HisTrap FF column (GE Healthcare) equilibrated with PBS, pH 7.4. The column was washed with 25 mm imidazole in PBS, pH 7.4 and bound protein was eluted with 250 mM imidazole in PBS, pH 7.4. Eluted protein was concentrated using Amicon Ultra-15 centrifugal filter devices (Millipore) with 10 kDa molecular weight cut-off, and further purified by SEC on a 26/60 Superdex 200 column (GE Healthcare) equilibrated and run with PBS, pH 7.4. Fractions containing CD40 were pooled, concentration measured by absorbance at 280 nm, and samples analyzed by SEC, SDS-PAGE, and mass spectrometry. [CD40(h)(21-193)]-Tev-His6 ("His6" disclosed as SEQ ID NO: 115) was stored in aliquots at −80° C.

Preparation and Purification of CD40 Ab102 Fab Fragment:

Fab fragment of CD40 Ab102 was prepared by papain cleavage of the parent mAb as detailed below. Papain was activated with 50 mM cysteine in PBS, pH 7.4 buffer. mAb CD40 Ab102 [hu IgG1/k] LALA QL in PBS, pH 7.4 buffer was mixed with papain at 1:100 weight ratio of papain to mAb and incubated for 1 h at 37° C. The reaction was quenched with 5 mM iodoacetamide. The mixture was purified on 10 ml Mab SelectSure resin (GE Healthcare) where the Fab fragment was collected as flow through. The flow through was concentrated using an Ultrafree-15 Biomax 10 kDa molecular weight cut-off (MWCO) centrifugal device (Millipore). The concentrated mixture was purified on 2.6 cm×60 cm Sephacryl 200 HiPrep column (GE Healthcare) pre-equilibrated in 50 mM HEPES, 50 mM NaCl, pH 7.5 buffer. Fractions containing Fab fragment (monitored by UV absorbance at 280 nm) were pooled and frozen at −80° C. Sample purity was assessed by analytical SEC, SDS-PAGE and mass spectrometry.

CD40/CD40 Ab102 Fab Complex Preparation:

Recombinant human CD40 was expressed in mammalian expression system and subsequently purified using techniques well known in the art. Recombinant human CD40 and CD40 Ab102 Fab protein were mixed at a 1.1:1 molar ratio and incubated for 4 h at 4° C. The complex sample was loaded onto a 2.6 cm×60 cm Sephacryl 200 HiPrep column (GE Healthcare) pre-equilibrated in 50 mM HEPES, 50 mM NaCl, pH 7.5 buffer at 1 ml/min Fractions containing the complex (monitored by UV absorbance at 280 nm) were pooled and concentrated to 18 mg/ml using an Ultrafree-15 Biomax 10 kDa molecular weight cut-off (MWCO) centrifugal device (Millipore). Sample purity was assessed by analytical SEC and SDS-PAGE.

Ab102 Fab Crystallization:

Fab alone was supplied at 22.5 mg/ml in 50 mM HEPES, 50 mM NaCl, pH 7.5. Crystals grew by vapor diffusion at 23° C. The reservoir contained 25% (w/v) PMME 550, 0.1 M MES pH 6.5, 0.01 M zinc sulfate. The drop was made by adding equal volumes of protein and reservoir solution. Crystals grew as thick prisms and were cryo-protected using the reservoir solution with the addition of 10% (v/v) propylene glycol. Crystals were harvested, swished through cryo-solution and cryo-cooled directly in liquid nitrogen. Diffraction data to 1.74 Å were collected under gaseous nitrogen at 100 K at the 17ID beamline at the Advanced Photon Source at Argonne National Laboratories (Argonne Ill.).

Ab102 Fab Complexed to CD40 Antigen Crystallization:

The Fab complex was supplied at 18 mg/ml in 50 mM HEPES, 50 mM NaCl, pH 7.5. The antigen construct used was [CD40 (h) (21-193)]-TEV-6His ("His6" disclosed as SEQ ID NO: 115). Crystals grew by vapor diffusion at 23° C. The reservoir contained 2 M ammonium sulfate, 0.1 M phosphate-citrate pH 4.2. The drop was made by adding equal volumes of protein and reservoir solution. Crystals grew as thin rods and were cryo-protected using 2.5 M lithium sulfate. Crystals were harvested, swished through cryo-solution and cryo-cooled directly in liquid nitrogen. Diffraction data to 2.84 Å were collected under gaseous nitrogen at 100 K at the 17ID beamline at the Advanced Photon Source at Argonne National Laboratories (Argonne Ill.).

Structure Determination of Ab102 Fab and Ab102 Fab CD40 Complex

Diffraction data for both crystal structures were processed using the program autoPROC from Global Phasing Ltd.

The Ab102 Fab dataset was processed in the space group $C222_1$ with the following unit cell dimensions: a=64.65 b=130.4 c=132.6. A maximum likelihood molecular replacement solution was determined using the program PHASER using an Fab search model reported previously (Protein Data Bank entry 3Q0S). Coordinates for 1 Fab molecule were generated based on the molecular replacement solution. Preliminary refinement of the resulting solution was conducted using REFMAC and the program BUSTER. Iterative protein model building was conducted using the program COOT and examination of 2Fo-Fc and Fo-Fc electron-density maps. Refinement concluded with the addition of water molecules using BUSTER. Final refinement statistics reported $R_{free}/R_{work}$ values of 0.23/0.19.

The Ab102 Fab CD40 complex dataset was processed in the space group $P2_12_12$ with the following unit cell dimensions: a=173.3 b=76.0 c=126.1. A maximum likelihood molecular replacement solution was determined using the program PHASER using the previously solved Ab102 Fab reported above. Coordinates for 2 Fab molecules were found based on the molecular replacement solution. Preliminary refinement of the resulting solution was conducted using REFMAC and the program BUSTER. The model for CD40 was built manually using the program COOT and examination of 2Fo-Fc and Fo-Fc electron-density maps. Refinement concluded with the addition of water molecules using BUSTER. Final refinement statistics reported $R_{free}/R_{work}$ values of 0.25/0.20.

Example 7

Neutralization Potency and Agonist Activity of Ab102 in the Monocyte Activation Assay The following methods were used in this example which examined the antagonist and agonist activity of Ab102 in vitro.

Antagonist Assay: The ability of Ab102 to block CD40-mediated monocyte activation was assessed in an antagonist assay. Purified monocytes were mixed with 1 μg/mL MEGACD40L (Enzo) in the presence of 80 ng/mL GM-CSF and 80 ng/mL IFNγ at a concentration of $2\times10^6$/mL. 50 μL was added per well in a 96-well U-bottom tissue culture (TC) plate. Dilutions of tested materials were prepared in culture medium, and 50 μL of dilutions were added to human monocytes obtained from a donor. Cells were cultured at 37° C., 5% $CO_2$ for two days before supernatants were harvested for cytokine (TNF) analysis using Meso Scale Discovery (MSD) immunoassay platform.

Agonist Assay: The ability of Ab102 to induce monocyte activation through CD40 was assessed. MEGACD40L (Enzo) was used as a positive control for monocyte activation. Purified human monocytes were diluted to $2\times10^6$/mL in culture medium in the presence of 80 ng/mL GM-CSF and 80 ng/mL IFNγ, and 50 μL/well was added in a 96-well U bottom TC plate. Dilutions of tested materials were prepared in culture medium, and 50 μL of dilutions were added to the monocytes. Cells were cultured at 37° C., 5% $CO_2$ for two days before supernatants were harvested for cytokine (TNF) analysis using Meso Scale Discovery (MSD) immunoassay platform.

As myeloid cells play an important role in the pathogenesis of Crohn's disease, the above-mentioned monocyte-based assays were developed to evaluate the functional activity of Ab102. CD40 signaling induces the activation of monocytes and thereby the production of inflammatory cytokines such as TNF. Representative monocyte antagonist and agonist assays for Ab102 are shown in FIGS. 5A and 5B, respectively. As shown in FIG. 5A, Ab102 blocked the expression of TNF in a concentration-dependent manner. In the agonist assay format, soluble CD40L induced the production of TNF from monocytes with an $EC_{50}$ of 1.9 nM, while Ab102 did not induce TNF production at concentrations up to 200 nM. As described in FIG. 5B, Ab102 levels of TNF were similar to those of the negative control (non-relevant IgG) showing little to no detectable TNF production. Consistent results were obtained from three different donors with the IC50 values shown in Table 20 below.

TABLE 20

Summary of Functional Assessment of Ab102 in Monocyte Activation Assay

| Reagent | Experiment | Antagonist $IC_{50}$ (nM) |
|---|---|---|
| Ab102 | 1 | 0.06 |
|  | 2 | 0.23 |
|  | 3 | 0.11 |
|  | Average ± SD | 0.13 ± 0.08 |

In sum, results from testing Ab102 in both the antagonist and the agonist assays described above showed that Ab102 is an antagonist anti-CD40 antibody that is substantially free of agonist activity with no measurable agonist activity.

Example 8

Cross-Reactivity of Ab102

The cross-reactivity of Ab102 with CD40 from various species was tested. Using standard techniques, Alexa 647 labeled Ab102 demonstrated similar binding kinetics to both human and cynomolgus monkey CD40 on the surface of B cells with an EC50 value of 0.89±0.17 nM on human cells and 1.4±0.15 nM on cynomolgus monkey cells, as shown in Table 21, below. Binding of Ab102 to mouse, rat, and rabbit CD40 could not be detected at concentrations up to 30 µg/mL (200 nM).

TABLE 21

Summary of Ab102 Binding to Various CD40 on the Surface of B Cells

| Reagent | Species | $EC_{50}$ (nM) |
|---|---|---|
| Ab102 | Human | 0.89 ± 0.17 |
|  | Monkey | 1.4 + 0.15 |
|  | Mouse | ND |
|  | Rat | ND |
|  | Rabbit | ND |

In sum, Ab102 bound to human and cynomolgous monkey CD40, but showed no detectable binding to mouse, rat, or rabbit CD40 using standard binding assays.

Example 9

Use of Mouse Anti-CD40 Antibody 138 to Treat T-Cell Transfer Colitis

The following methods were used in an in vivo study to determine the ability of a mouse anti-CD40 antibody (anti-body 138) to treat colitis. Anti-murine CD40 antibody 138 has similar characteristics to Ab102, e.g., antibody 138 is an antagonist antibody with no substantial agonist activity like Ab102. Thus, antibody 138 is representative of Ab102 activity in the mouse model of Example 9. The following describes an in vivo T cell transfer model of colitis.

Isolation and Injection of Naïve T Cells

On Day 0, spleens were collected from balb/c mice and placed in RPMI media supplemented with 4% fetal bovine serum (complete media) on ice. A single cell suspension was obtained by mechanical disruption and passing through a 100 µm cell strainer into RPMI media supplemented with 4% fetal bovine serum (complete media). Cells were collected by centrifugation (1250 rpm for 10 minutes at 4° C.) and re-suspension in Robosep Buffer (Stem Cell Technologies). Cell concentration was measured using a Moxi Mini Cell Counter (Orflo) and adjusted to $1 \times 10^8$ cells/mL in Robosep buffer. CD4+ T cells were isolated using a negative selection magnetic bead kit (Stem Cell Technologies) according to the manufacturer's directions. Cells were further purified by FACS to yield populations of $CD4^+ CD45RB^{high}$ and $CD4^+CD45RB^{low}$ which were collected as the brightest 42% and the dullest 12% of cells, respectively. Cells were counted and adjusted to $1 \times 10^6$ cells/ml, and 0.5 mL ($1 \times 10^5$ cells) were injected intraperitoneally (IP) into SCID mice.

Treatment

Mouse anti-CD40 antibody 138 was then administered at various doses IP in PBS twice/week to SCID mice (described above) starting either at the time of cell injection (prophylactic treatment) or after disease was confirmed by endoscopy (therapeutic treatment). In addition, a number of control groups were included. Groups received either 1) 15 mg/kg IP of antibody 951 (a non-relevant IgG) in PBS twice/week, or 2) antibody 138 (an antibody that blocks CD40L) IP in PBS, twice/week. Additionally, in the T-cell transfer (TCT) studies, either an anti-p40 (IL-12/23) antibody or an anti-TNF monoclonal antibody was administered as clinically relevant control comparators.

Endoscopy

At various times following cell injection into the mice, disease was assessed by colonoscopy. Following anesthesia with isoflurane, a flexible gavage needle was slowly inserted into the anus and 300 µL PBS was slowly injected to remove fecal pellets. Animals were allowed to recover from anesthesia and ambulate to facilitate passing of any remaining pellets (approximately five minutes). Mice were again anesthetized with isoflurane and the endoscopy probe (Karl Storz) was inserted into the anus to a depth of 3 cm. Photo images were captured at 3, 2 and 1 cm from the anal verge. Images were scored at a later time using the scale detailed in Table 22 below. Scores for each parameter at each of the three distances were combined to produce the Murine Endoscopic Disease Activity Index (MEDAI) Sum Score, shown in Table 22. The maximum score that could be obtained using the MEDAI Sum Score was 24.

In the case of therapeutic dosing, endoscopic scoring three weeks after cell injection was used to confirm disease and group animals for treatment.

TABLE 22

MEDAI Endoscopic Scoring

| Parameter | Score | Description |
|---|---|---|
| Exudate | 0 | Normal |
| | 1 | covers <50% of colon circumference |
| | 2 | covers >50% of colon circumference |
| Vascularity | 0 | Normal |
| | 1 | vessels disconnected, small vessels not visible |
| | 2 | large vessels not visible, starburst pattern |
| | 3 | surface bleeding apparent, vessels appear leaky |
| Mucosal Granularity | 0 | Normal |
| | 1 | slight cobblestone appearance |
| | 2 | pronounced and extensive cobblestone appearance |
| | 3 | mucosal protrusion, reduced lumen |

Histology

GI samples were submitted in cassettes in the stretch segmented whole colon orientation, which allowed for analysis of the entire colon length and processed for formalin-fixed paraffin-embedded (FFPE). Blocks were sectioned at 5 micron, and mounted on glass slides prior to performing immunohistochemistry to detect ionized calcium binding adaptor molecule 1 (IBA1) using anti-IBA1 antibody (Cat. No. 019-19741; Wako Pure Chemical Industries, Ltd.). The IBA1 marker was used to identify macrophages in the tissue sections. Slides were counterstained with methyl green, dehydrated, and mounted with a glass coverslip.

Slides were then scanned at 4× by the Vectra imaging system and 4× low power mosaic images were reviewed prior to selection of areas to image at 20×.

Vectra imagining rescanned slides and captured the selected 20× high power high resolution images which were then subjected to image analysis algorithms in the inForm software (Perkin Elmer). The inForm algorithm set that was used has three algorithms: the first thresholds the staining for IBA1 and CD3 in spectrally imaged files, to eliminate background/extraneous stain. The subsequent algorithms segment the tissue into tissues of interest (lamina propria, epithelium, muscularis, submucosa and background), and quantifies either CD3 or IBA1 in the RGB images produced from the first algorithm.

InForm data was exported to text files which were merged into single data files for either tissue segmentation or cell segmentation data.

Based on the validation of antagonist activity in the acute models, a model of chronic colitis was used to establish proof of concept. Three studies were conducted to test the effect of blocking colitis following transfer of naïve T cells into an immunocompromised host (SCID mouse). A single dose level was investigated in both prophylactic and therapeutic treatment mode while a full dose response was examined in prophylactic mode.

Figure 6:
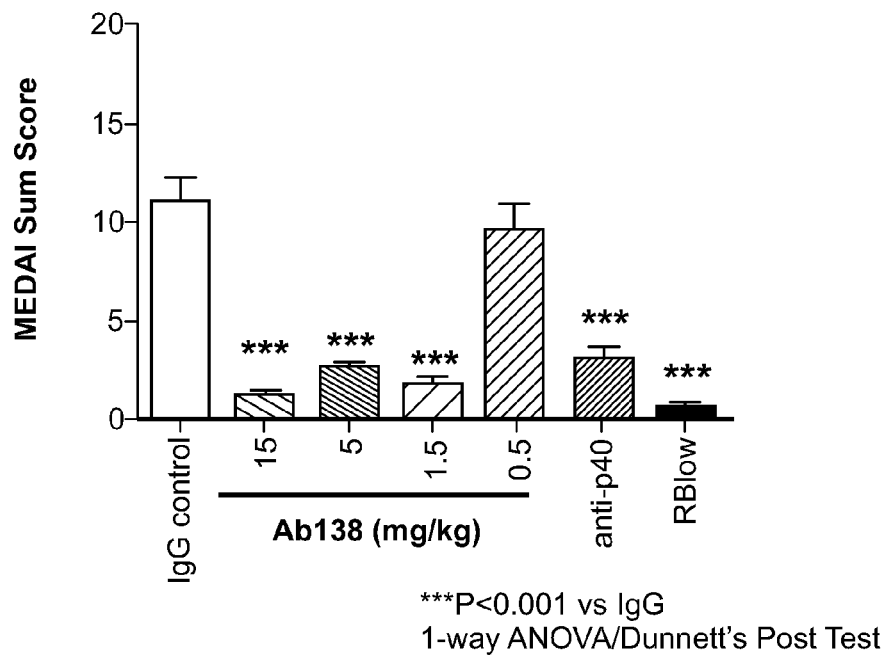
FIG. 6 graphically depicts the dose responsive inhibition of endoscopy score with prophylactic administration of antibody 138 (Ab138). Antibody 138 was tested at doses of 15, 5, 1.5 and 0.5 mg/kg. An IgG negative control was used. Anti p40IL-12/23 treatment was used as a positive control. Disease is mediated by CD45Rbhi cells that are transferred to animals. RBlow refers to the negative control group. CD45RBlow cells do not mediate disease.
Figure 7:
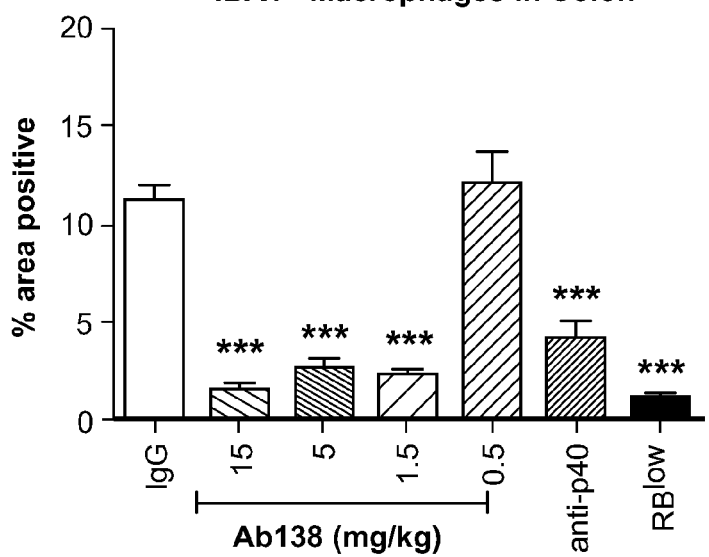
FIG. 7 graphically depicts the results of immunohistochemical analysis to determine IBA1+ macrophages in the colon with administration of antibody 138 (Ab138). Histological analysis of colonic sections showed a decrease in macrophages (general measure of inflammation). An IgG negative control was used. Anti p40IL-12/23 treatment was used as a positive control.
Figure 8:
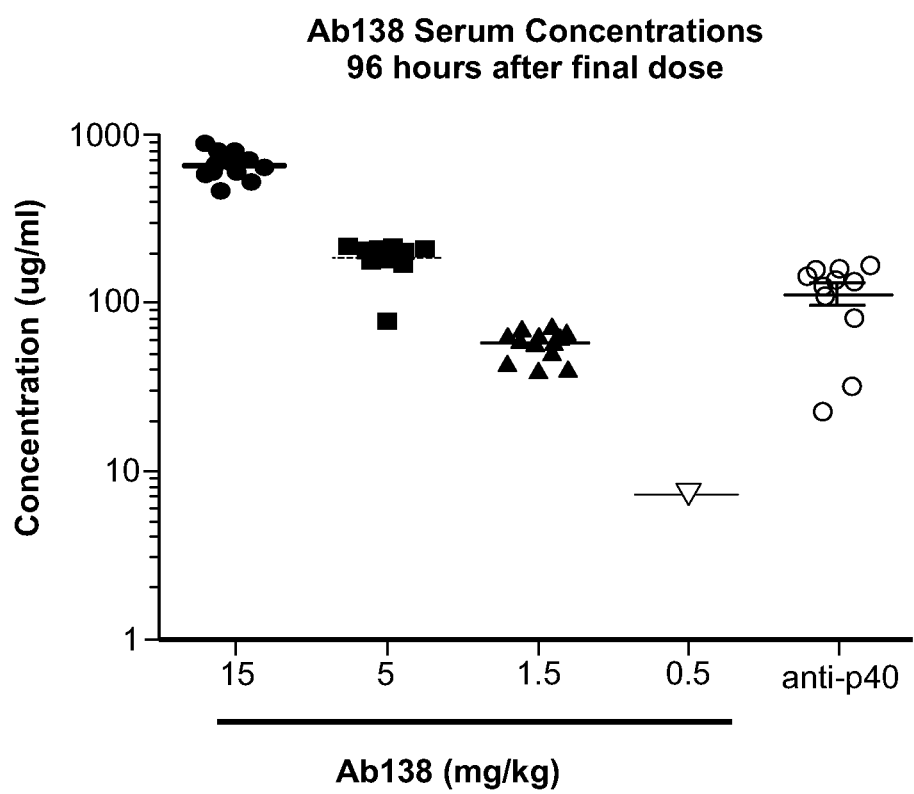
FIG. 8 graphically depicts serum levels of circulating antibody 138 (Ab138) 96 hours (equal to $C_{trough}$) after the final dose in the T-cell transfer model of colitis. The serum levels were shown to be dose responsive. Anti p40IL-12/23 treatment was used as a positive control. Only 1 animal in the 0.5 mg/kg group has measurable levels of Ab138.

Dose Response of a Mouse Anti-CD40 Antibody 138 Administered at the Time of Cell Transfer The dose response of prophylactically administered mouse anti-CD40 antibody 138 was determined using the T cell transfer model of colitis. Treatment that covered a range of doses (0.5, 1.5, 5 and 15 mg/kg) was initiated at the time of cell transfer. Doses down to 1.5 mg/kg resulted in maximum inhibition of the MEDAI sum score, while 0.5 mg/kg had no significant effect. Activity of the mouse anti-CD40 antibody 138 was equivalent to the standard dose of anti-p40IL-12/23 treatment used as a positive control. Histological analysis of colonic sections showed a decrease in macrophages (a general measure of inflammation) that correlated well with endoscopic assessment of disease, as described in FIG. 6 and FIG. 7. Specifically, FIG. 6 describes dose response inhibition of endoscopy score with prophylactic administration of mouse anti-CD40 antibody 138 at day 39 (terminal score). In FIG. 6, RBlow refers to the negative control group. CD45RBlow cells do not mediate disease. In this model of colitis, disease is mediated by CD45RBhi cells that were transferred to animals. FIG. 7 shows the number of IBA1+ macrophages in the colon of the mice (determined histologically) and describes lower levels of macrophages at doses greater than 0.5 mg/kg and lower than the p40 positive control Levels of circulating mouse anti-CD40 antibody 138 were measured 96 hours after the final dose (equivalent to $C_{trough}$) and were shown to be dose responsive as described in FIG. 8. The lowest dose level (0.5 mg/kg) resulted in a concentration <lower limit of quantification (LLOQ) in all but one animal in that group.

Figure 9A:
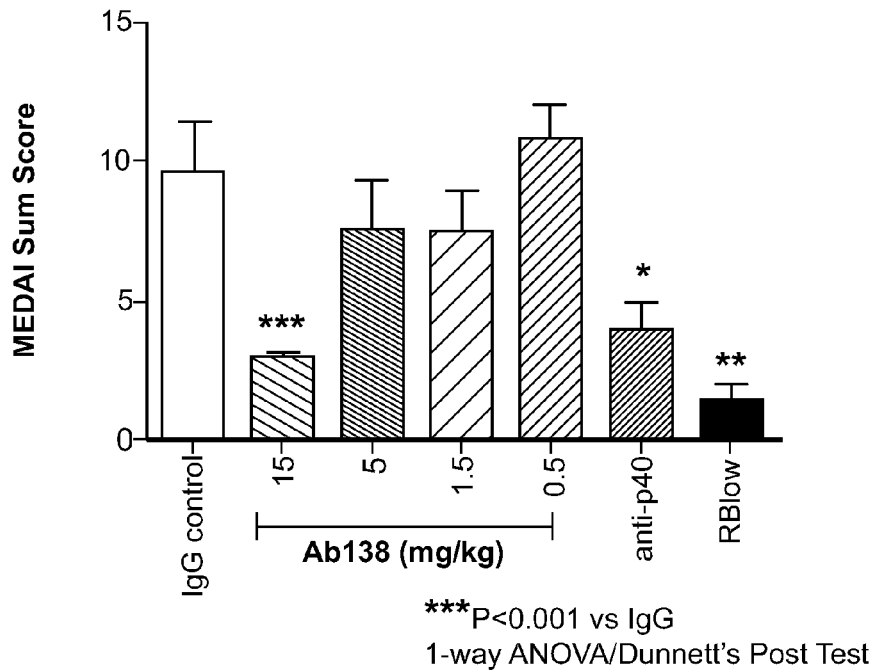
FIG. 9A graphically depicts endoscopy results following administration of antibody 138 in a colitis mouse model. Antibody 138 (Ab138) treatment was initiated three weeks post cell injection, following confirmation of endoscopic disease, and a dose responsive inhibition of the MEDAL sum score was noted. The highest dose (15 mg/kg) reached statistical significance (FIG. 9A).
Figure 9B:
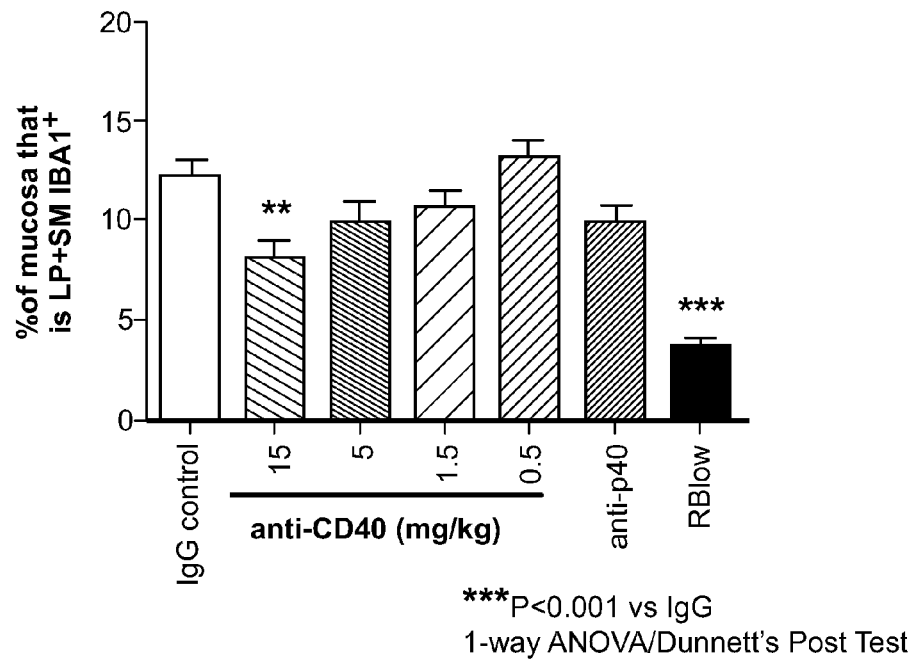
FIG. 9B graphically depicts histology results following administration of antibody 138. Histological analysis of IBA1+ macrophages in the colon as a measure of myeloid inflammation is shown in FIG. 9B.

Dose Response of a Mouse Anti-CD40 Antibody 138-Administered 3 Weeks Post Cell Transfer When mouse anti-CD40 antibody 138 treatment was initiated three weeks post cell injection, following confirmation of endoscopic disease, a dose responsive inhibition of the MEDAI sum score was observed with the highest dose (15 mg/kg) reaching statistical significance (FIG. 9A). Histological analysis of IBA1+ macrophages in the colon as a measure of myeloid inflammation yielded similar results, as described in FIG. 9B. The mean serum concentration of antibody 138 measured 72 hours after the final dose was 191.9 µg/ml in animals that received 15 mg/kg.

Example 10

T-Cell Dependent Antibody Responses in Cynomolgus Monkeys

A T-cell dependent antibody response (TDAR) assay was conducted in cynomolgus monkeys. Two/sex/group were administered Ab102 at dosages of 0 (vehicle only) or 10 mg/kg subcutaneously (SC) for 5 weeks. Keyhole limpet hemocyanin (KLH) was administered to all animals on Day 8. Serum samples were collected from each animal at −11, −7, 0, 4, 7, 10, 14 and 21 days relative to KLH administration. All animals were returned to testing facility animal colony following completion of last scheduled blood collection (FIG. 10).

It was found that Ab102 suppressed both the anti-KLH IgM and IgG antibody T cell dependent antibody responses, as compared to vehicle only treated animals, as shown in FIG. 10.

The findings in this study were consistent with the pharmacologic suppression of CD40-dependent IgM and IgG antibody production following parenteral administration of a prototypic foreign protein. The results suggested that use of Ab102 may be relevant for treating lupus, where autoantibody production is part of the disease. These findings also supported the biologic relevance of cynomolgus monkeys as an appropriate species for preclinical toxicology studies. Further, the study demonstrated cross-reactivity to cynomolgus monkey CD40, and shows in vivo activity of Ab102 in a mechanism (T-dependent antibody response) which is known to require CD40.

Example 11

Use of Mouse Anti-CD40 Antibody 138 to Treat Systemic Lupus Erythematosus (SLE)

Because of the antagonist activity of the mouse anti-CD40 antibody 138 that was shown in the above acute models and in a model of colitis (see Example 9), the efficacy of this mouse anti-CD40 antibody was examined in mouse models of systemic lupus erythematosus (SLE). Two SLE models were used: MRL/lpr and NZB/W-F1 (described in Theofilopoulos and Kono. 1999. *Murine lupus models: gene-specific and genome-wide studies*. In Lahita R. G., ed., Systemic Lupus Erythematosus, 3rd edn, p. 145). The rationale for assessing the efficacy of anti-CD40 treatment in MRL/lpr and NZB/W-F1 mice is two-fold. First, the models differ in their manifestations of SLE. NZB/W-F1 mice spontaneously develop lupus nephritis and sialadenitis, whereas MRL/lpr mice develop joint and skin manifestations in addition to nephritis and sialadenitis (Andrews et al. J. Exp. Med. 148: 1198-1215. 1978). Since patients differ in their manifestations of SLE, the use of both models allows the assessment of potential efficacy in a majority of SLE patients. Second, MRL/lpr and NZB/W-F1 mice differ in the genetic basis for their disease (Perry et al. J. Biomed. Biotech. 2011, Article ID 271694), and therefore, efficacy across models increases confidence in the translation to genetically heterogeneous human.

11.1. MRL/lpr Model of SLE

To determine efficacy, mice were administered mouse anti-CD40 antibody 138 by intraperitoneal injection (i.p.) beginning at 10 weeks of age at the doses indicated in Table 23, below. PBS injections were used as a negative control, and prednisolone was used as a positive control in the study.

TABLE 23

| Group | n | Treatment | Dose |
| --- | --- | --- | --- |
| 1 | 18 | PBS | 2×/wk i.p. |
| 2 | 18 | Antibody 138 | 15 mg/kg 2×/wk i.p. |
| 3 | 18 | Antibody 138 | 5 mg/kg 2×/wk i.p. |
| 4 | 18 | Antibody 138 | 1.5 mg/kg 2×/wk i.p. |
| 5 | 18 | Antibody 138 | 15 mg/kg 1×/wk i.p. |
| 6 | 18 | Prednisolone | 10 mg/kg PO sid |

Figure 11A:
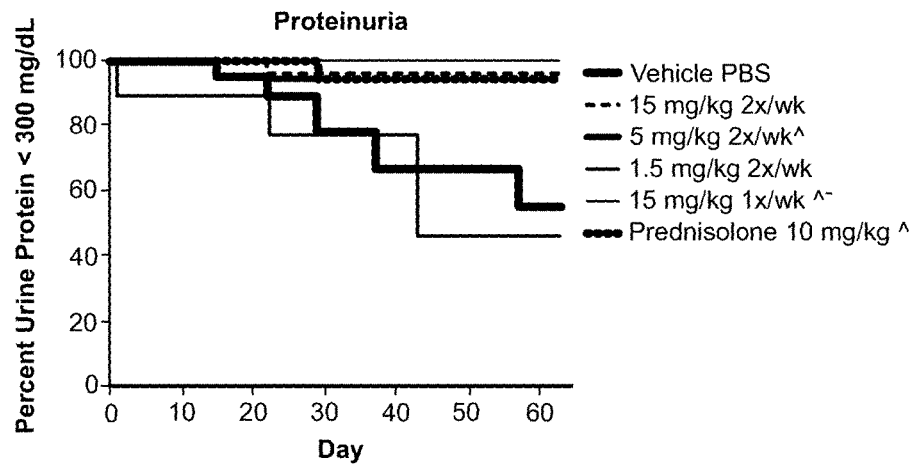
FIG. 11A is a graph that shows anti-CD40 antibody 138 treatment prevented proteinuria in MRL/lpr mice. Mice were dosed with 15 mg/kg of antibody 2×/week, 5 mg/kg of antibody 2×/week, 1.5 mg·kg of antibody 2×/week or 15 mg/kg antibody 1×/week. Administration of phosphate buffered saline (PBS) vehicle alone was used as a control. Proteinuria was determined as percent urine protein <300 mg/dL.
Figure 11B:
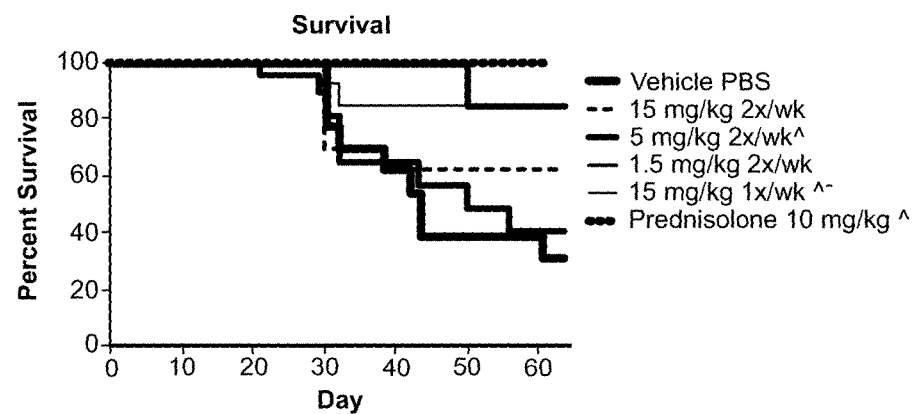
FIG. 11B is a graph that depicts results showing that anti-CD40 antibody 138 treatment extended survival of MRL/lpr mice. Animals were dosed with 15 mg/kg of antibody 2×/week, 5 mg/kg of antibody 2×/week, 1.5 mg·kg of antibody 2×/week or 15 mg/kg antibody 1×/week. Administration of vehicle alone was used as a control. Percent survival was indicated over time.

Proteinuria was monitored weekly by Albustix (a brand of urine dip sticks used to test for urine protein). High proteinuria, defined as ≥300 mg/dL, began to develop shortly after treatment began, as shown in FIG. 11A. As described in FIG. 11A, by study completion at day 63, 50-60% of untreated PBS control mice and mice treated with 1.5 mg/kg of anti-CD40 antibody had developed high proteinuria. In contrast, nearly all mice in the other treatment groups maintained low proteinuria throughout the study. The 15 mg/kg 1× per week treatment group was significantly different from the PBS control. Survival was also monitored and it was found that dosing at 15 mg/kg 1× per week and 5 mg/kg 2× per week significantly extended survival over the untreated PBS control animals, as shown in FIG. 11B. It should be noted that many mice were euthanized due to distress caused by lymphadenopathy caused by the Faslpr mutation before they developed nephritis. Thus, the observed decrease in survival cannot be attributed solely to nephritis. Nevertheless, these data indicate that anti-CD40 antibody dose dependently prevented proteinuria and extended survival of lupus-prone MRL/lpr mice.

Efficacy of the anti-CD40 antibody for treating SLE was also evaluated in hematoxylin and eosin (H&E) stain stained formalin-fixed paraffin-embedded (FFPE) tissue sections from the kidney, salivary gland, and ankle joints of mice from the various treatment groups. Severity of disease in all test organs in the control untreated PBS mice increased over the 9 weeks of the study as the MRL mice aged from 10 weeks of age at the beginning to 19 weeks at the end.

Figure 12B:
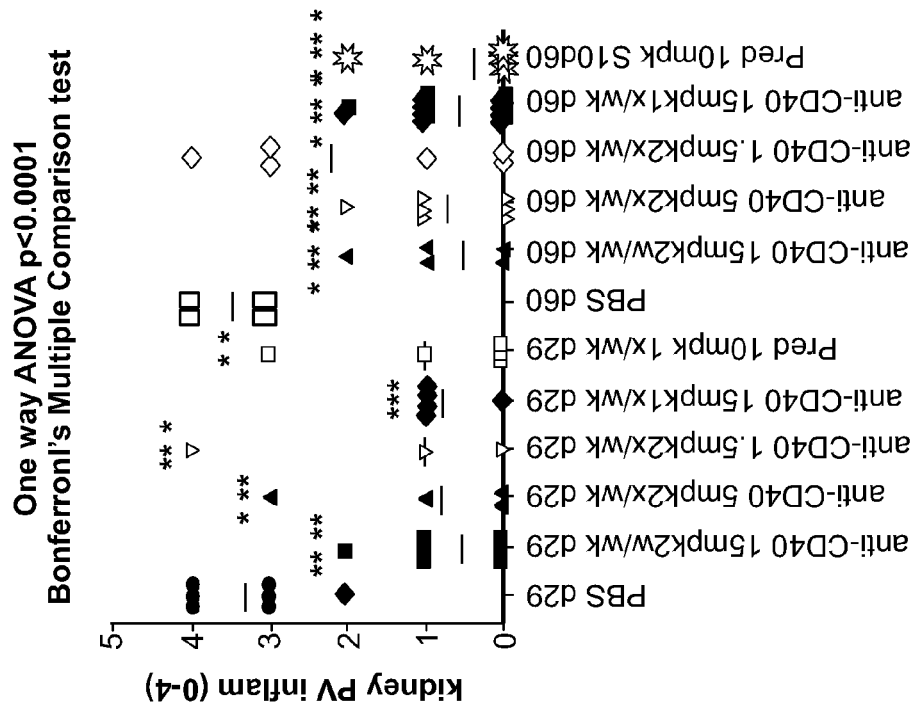
FIG. 12B is a graph that depicts results showing that anti-CD40 antibody treatment prevented the development of nephritis.
Figure 12A:
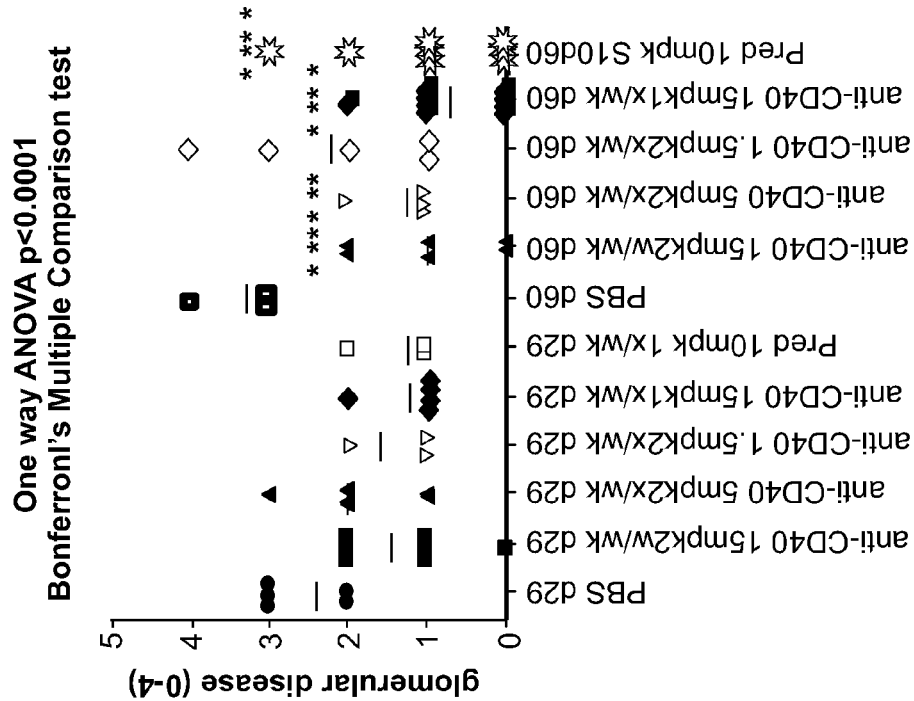
FIG. 12A is a graph that depicts results showing that anti-CD40 antibody 138 treatment prevented the development of nephritis.
Figure 12C:
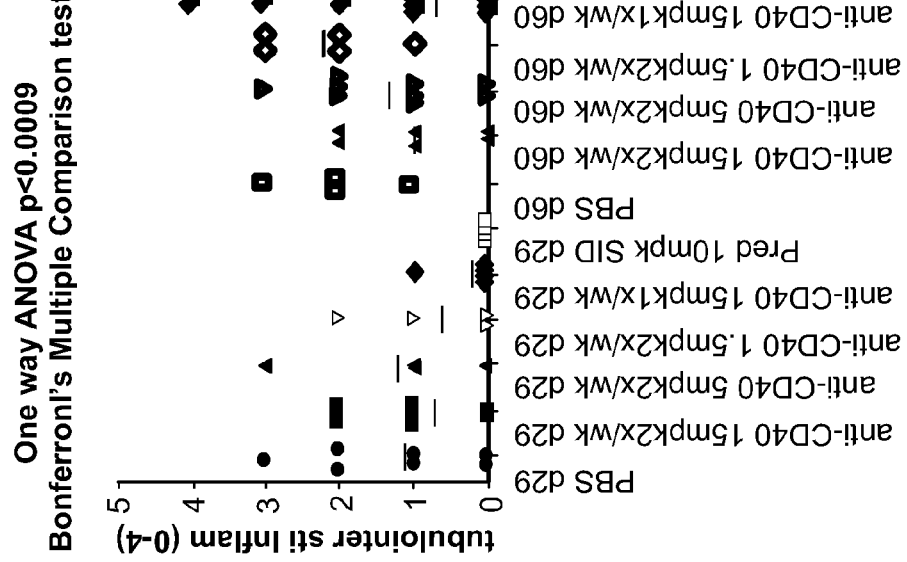
FIG. 12C is a graph that shows anti-CD40 antibody 138 treatment prevented the development of nephritis.

In the kidney, anti-CD40 antibody treatment was efficacious when administered at 15 mg/kg in reducing glomerular disease at both 29 and 63 days of treatment, as shown in FIG. 12A. As glomerular disease severity worsened in aging MRL mice, anti-CD40 antibody treatment maintained efficacy at minimizing glomerular disease at 5 and 15 mg/kg. Anti-CD40 antibody given in a dose of 15 mg/kg once a week was as effective as dosing twice a week. Anti-CD40 antibody given at a dose of 5 mg/kg twice a week was also near the same effectiveness. Anti-CD40 antibody given at a dose of 5 and 15 mg/kg was effective at reducing perivascular (PV) infiltrates in the kidney at 29 and 63 days, as shown in FIG. 12B, with a trend at reducing tubulointerstitial (TI) early in disease, as shown in FIG. 12C.

Figure 13A:
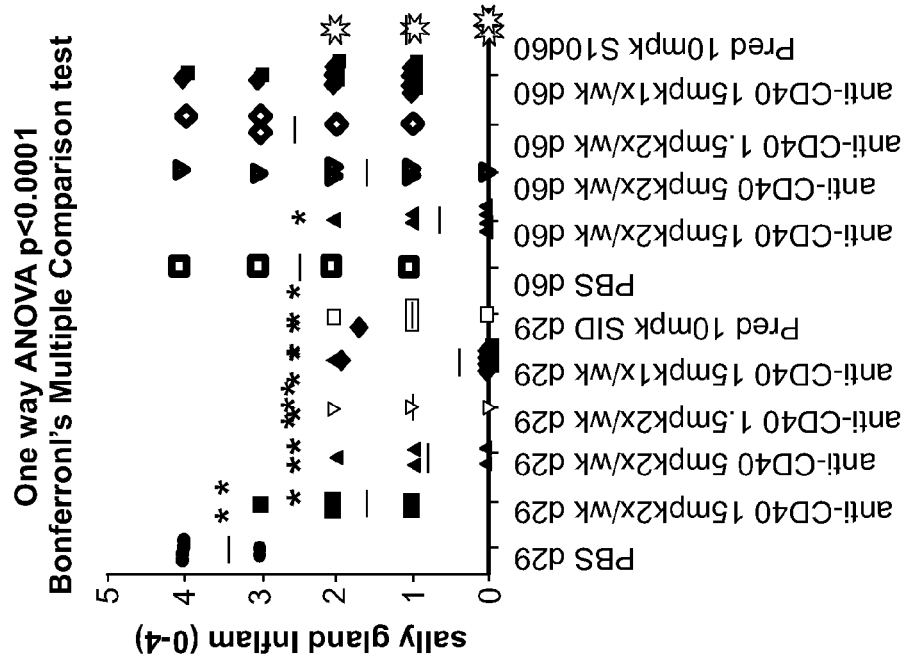
FIG. 13A is a graph that shows anti-CD40 antibody 138 treatment prevented salivary gland inflammation.

In the salivary gland, anti-CD40 antibody given at a dose of 1.5, 5 and 15 mg/kg was efficacious in reducing salivary gland inflammation at day 29, while 15 mg/kg maintained efficacy at day 63 of therapy (FIG. 13A). Salivary gland infiltration did not change significantly in the untreated mice after day 29.

Figure 13B:
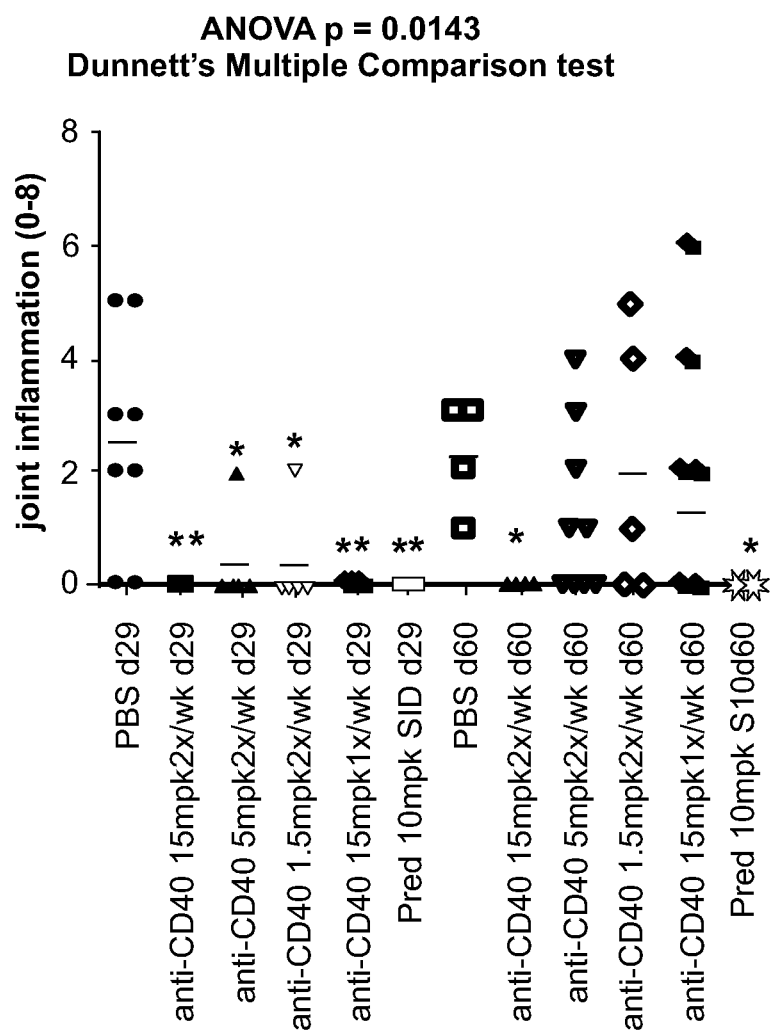
FIG. 13B is a graph that shows anti-CD40 antibody 138 treatment prevented joint inflammation.

In the tarsal joint tissue, anti-CD40 antibody administered doses of 1.5, 5 and 15 mg/kg was efficacious in reducing inflammation around the joint at day 29, while 15 mg/kg maintained efficacy at day 63 of therapy (FIG. 13B). In the joints, inflammation trended lower in the 19 week mice compared to the 10 week mice. Nevertheless, anti-CD40 antibody treatment significantly reduced inflammation to near zero at 15 mg/kg at 63 days of therapy.

Germinal center (GC) formation requires B and T cell interaction through engagement of CD40 on the GC B cell with CD40L on follicular helper T cells (Tfh). GCs are the anatomical structures where plasma cells and memory B cells are generated, and are where affinity maturation and Ig class switch occur. They are critical to the development of high affinity and pathogenic autoantibodies in SLE.

Figure 14:
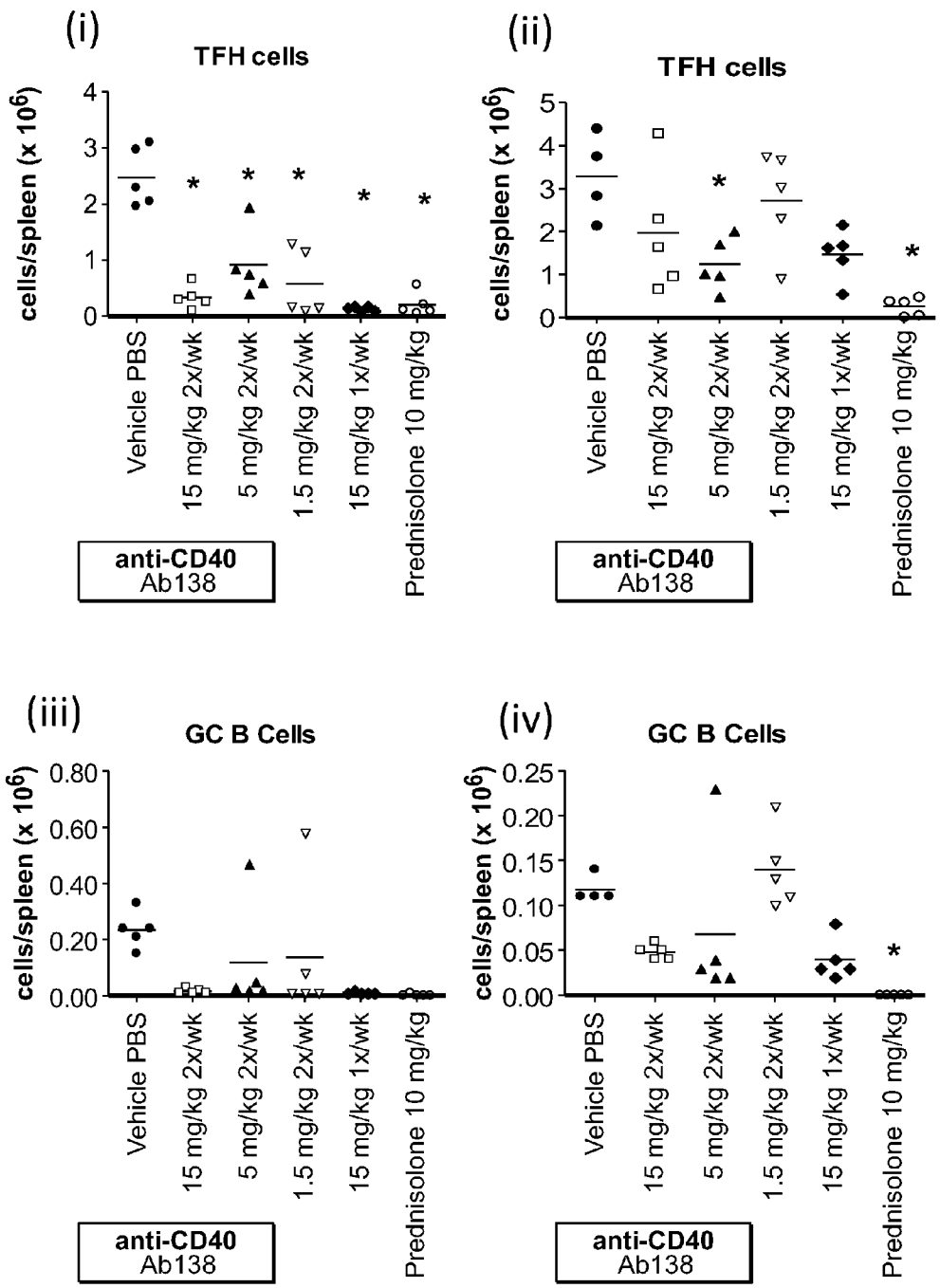
FIG. 14 is a panel of four graphs (i-iv) that shows that anti-CD40 antibody 138 prevented the expansion of follicular helper T cells (Tfh) and germinal center (GC) B cells in the spleen, as determined by flow cytometry. Mice were dosed with 15 mg/kg of antibody 2×/week, 5 mg/kg of antibody 2×/week, 1.5 mg·kg of antibody 2×/week or 15 mg/kg antibody 1×/week. Administration of PBS vehicle alone was used as a control. Panel (i) shows the number of Tfh cells in the spleen at day 29. Panel (ii) shows the number of Tfh cells in the spleen at day 63. Panel (iii) shows the number of GC B cells in the spleen at day 29. Panel (iv) shows the number of GC B cells in the spleen at day 63.

The mouse anti-CD40 antibody 138 disrupted the B and T cell interaction and prevented GC formation. To assess the extent to which GC formation was prevented, the number of GC B cells and Tfh cells in the spleen was determined by flow cytometry (FIG. 14). Tfh cell numbers were significantly lower than controls at day 29 in all anti-CD40 antibody 138 treated mice regardless of dose. Among the doses tested, the 5 mg/kg dose group remained significantly lower than control at day 63 (FIG. 14, see panels (i) and (ii)). GC B cells were also lower than control at day 29 at all anti-CD40 antibody doses, and they remained lower at day 63 in mice receiving anti-CD40 antibody at doses of 5 and 15 mg/kg. However, these differences from untreated controls were not statistically significant. Notwithstanding the results, there was an overall trend in the data toward a therapeutic effect in all dose groups. Furthermore, in these experiments, the murine anti-CD40 antibody demonstrated little to no agonist activity.

Figure 15A:
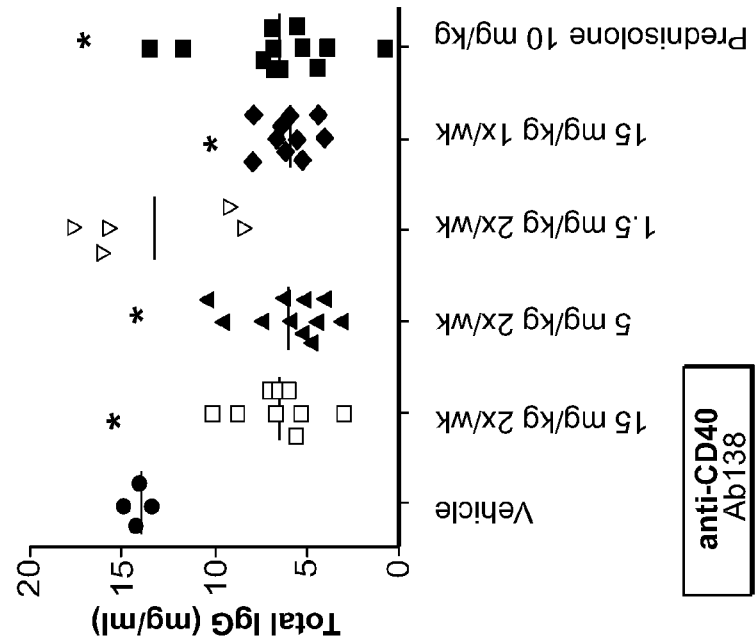
FIG. 15A is a graph that shows anti-CD40 antibody 138 treatment prevented an increase in total circulating IgG levels at day 29. Mice were dosed with 15 mg/kg of antibody 2×/week, 5 mg/kg of antibody 2×/week, 1.5 mg·kg of antibody 2×/week and 15 mg/kg antibody 1×/week. Administration of PBS vehicle alone was used as a control.
Figure 15B:
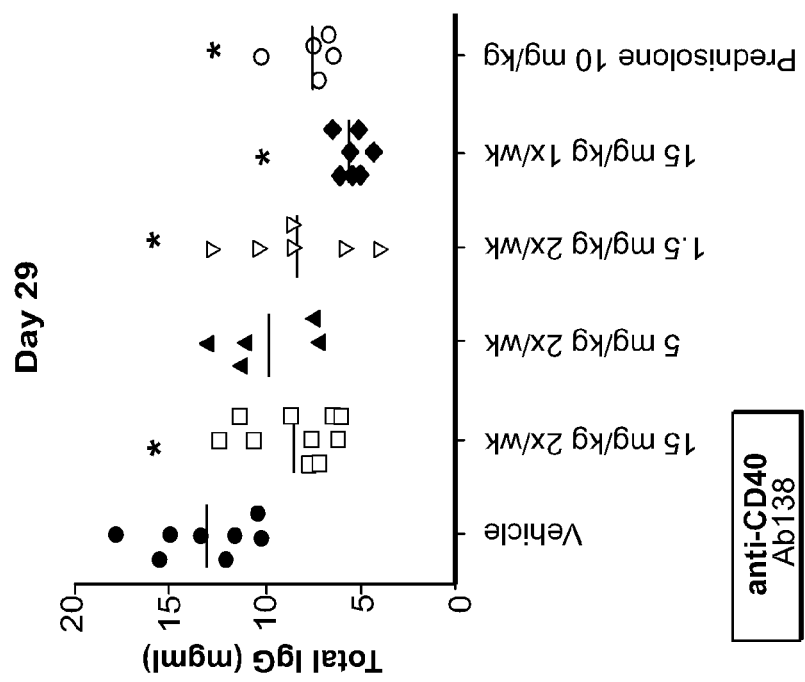
FIG. 15B is a graph that shows anti-CD40 antibody 138 treatment prevented an increase in total circulating IgG levels at day 63. Mice were dosed with 15 mg/kg of antibody 2×/week, 5 mg/kg of antibody 2×/week, 1.5 mg·kg of antibody 2×/week and 15 mg/kg antibody 1×/week. Administration of PBS vehicle alone was used as a control.

Circulating total IgG levels, in addition to the levels of autoreactive antibodies, increase over time in murine and human SLE. Therefore, to assess the effect of anti-CD40 antibody 138 on antibody production, total circulating IgM and IgG levels were examined. In addition, anti-dsDNA antibodies, a common lupus-associated autoantibody, were also examined. It was found that the total IgG levels in mice treated with anti-CD40 antibody at doses of 15 and 1.5 mg/kg were significantly lower than those in untreated controls at day 29, as described in FIG. 15A. Significantly lower total IgG levels persisted up to day 63 in mice treated with anti-CD40 antibody 138 at 15 mg/kg, as described in FIG. 15B. In addition, significantly lower levels were observed in mice treated with anti-CD40 antibody 138 at 5 mg/kg at this time point. No difference was found in circulating IgM levels.

Figure 16A:
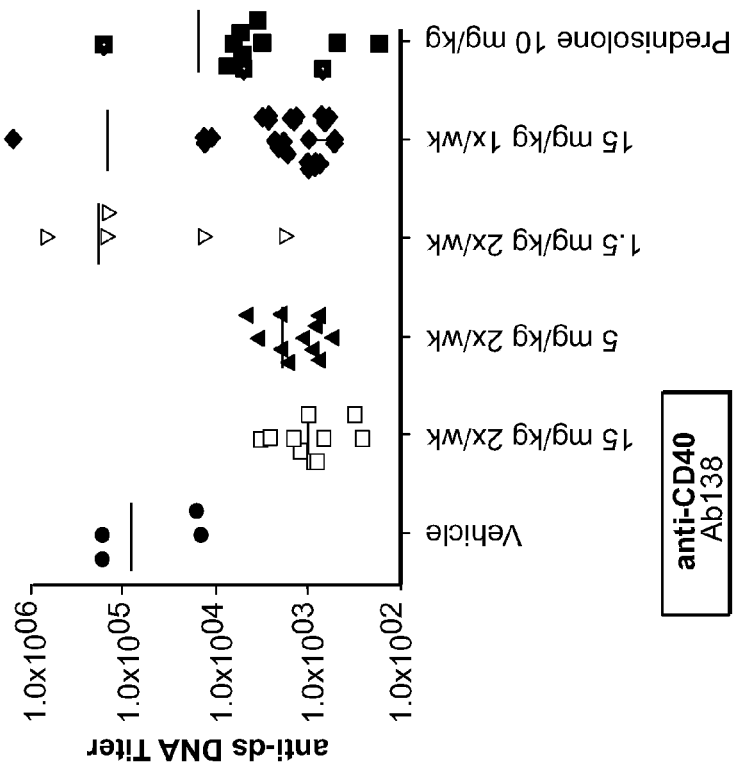
FIG. 16A is a graph that shows the effect of anti-CD40 antibody 138 treatment on anti-double stranded DNA (anti-dsDNA) titers at day 29. Mice were dosed with 15 mg/kg of antibody 2×/week, 5 mg/kg of antibody 2×/week, 1.5 mg·kg of antibody 2×/week or 15 mg/kg antibody 1×/week. Administration of PBS vehicle alone was used as a control. At day 29, anti-dsDNA titers were determined.
Figure 16B:
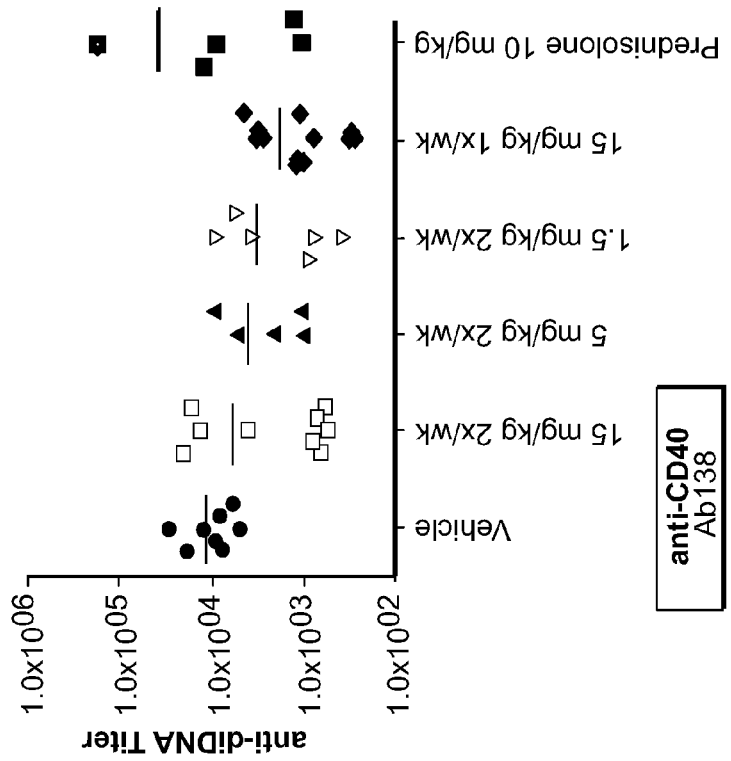
FIG. 16B is a graph that shows anti-CD40 antibody 138 treatment on anti-double stranded DNA (anti-dsDNA) titers at day 63. Mice were dosed with 15 mg/kg of antibody 2×/week, 5 mg/kg of antibody 2×/week, 1.5 mg·kg of antibody 2×/week or 15 mg/kg antibody 1×/week. Administration of PBS vehicle alone was used as a control. At day 63, anti-dsDNA titers were determined.

Anti-dsDNA titers were not significantly different in anti-CD40 antibody 138 treated and untreated control mice at day 29, as described in FIG. 16A. However, by day 63 anti-dsDNA titers had increased substantially in untreated control mice, but declined in mice treated with 15 and 5 mg/kg anti-CD40 antibody 138, although the difference was not significant, as described in FIG. 16B.

The results obtained from the above study (Example 11.1) indicate that anti-CD40 antibody 138 is efficacious in preventing the development of nephritis in the lupus-prone MRL/lpr mice. In addition, anti-CD40 antibody 138 prevented the development of salivary gland and joint inflammation. This study suggests that the antagonist mouse anti-CD40 antibody 138, having similar properties to Ab102, is efficacious for treating human SLE.

11.2. NZB/W-$F_1$ Mouse Model of SLE

A second mouse model for SLE was also tested to determine if antagonist mouse anti-CD40 antibody 138 is effective for treatment of the disease. Specifically, to determine the efficacy of anti-CD40 antibody 138, the antibody was tested in NZB/W-F1 mice, where both prophylactic and therapeutic regimens were used according to the dosing schedule described in Table 24, below. As in study 11.1, PBS served as a negative control and prednisolone was a positive control.

TABLE 24

| Group | n | Treatment | Dose |
|---|---|---|---|
| | | Prophylactic | |
| 1 | 20 | PBS | i.p 2×/wk |
| 2 | 20 | Antibody 138 | 15 mg/kg i.p. 2×/wk |
| 3 | 20 | Antibody 138 | 1.5 mg/kg i.p. 2×/wk |
| 4 | 20 | Antibody 138 | 15 mg/kg i.p. 1×/wk |
| 5 | 20 | Prednisolone | 10 mg/kg PO sid |
| | | Therapeutic | |
| 6 | 13 | PBS | i.p. 2×/wk |
| 7 | 12 | Antibody 138 | 15 mg/kg i.p. 2×/wk |
| 8 | 12 | Prednisolone | 10 mg/kg PO sid |

For the prophylactic regimen, mice began treatment at 26 weeks of age. All mice were verified to have <300 mg/dL protein. For the therapeutic regimen, a rolling enrollment was used; untreated mice were monitored weekly for proteinuria and were enrolled into one of the 3 arms of the therapeutic regimens when they developed proteinuria of ≥300 mg/dL.

Prophylactic Treatment

Figure 17A:
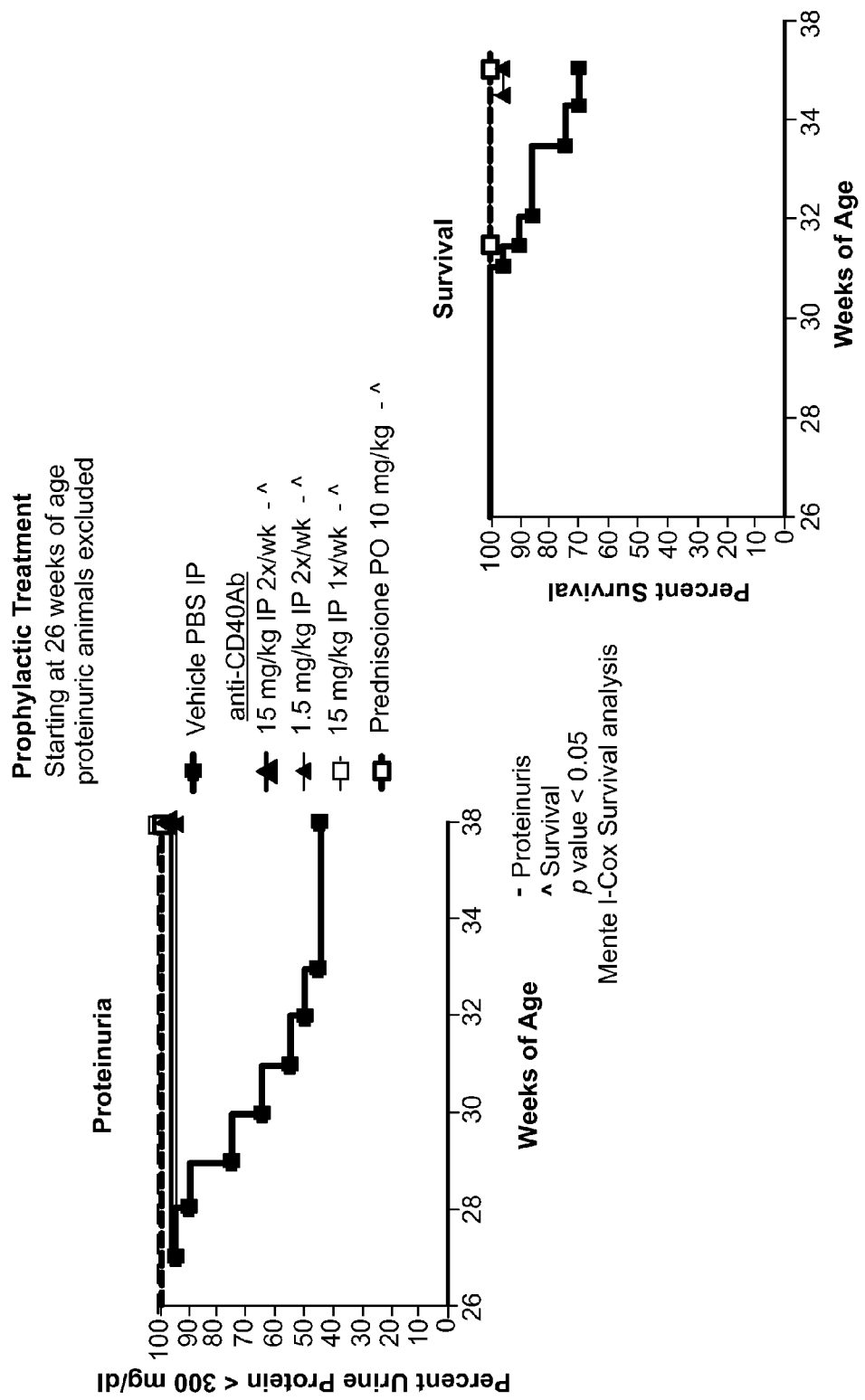
FIG. 17A is a graph that shows prophylactic dosing of anti-CD40 antibody 138 prevented proteinuria. Prophylactic treatment was started in mice at 26 weeks of age, and proteinuric mice were excluded from the study. Mice were dosed with 15 mg/kg of antibody 2×/week, 1.5 mg·kg of antibody 2×/week or 15 mg/kg antibody 1×/week. Administration of PBS vehicle alone was used as a control. Proteinuria was determined as percent urine protein <300 mg/dL.
Figure 17B:
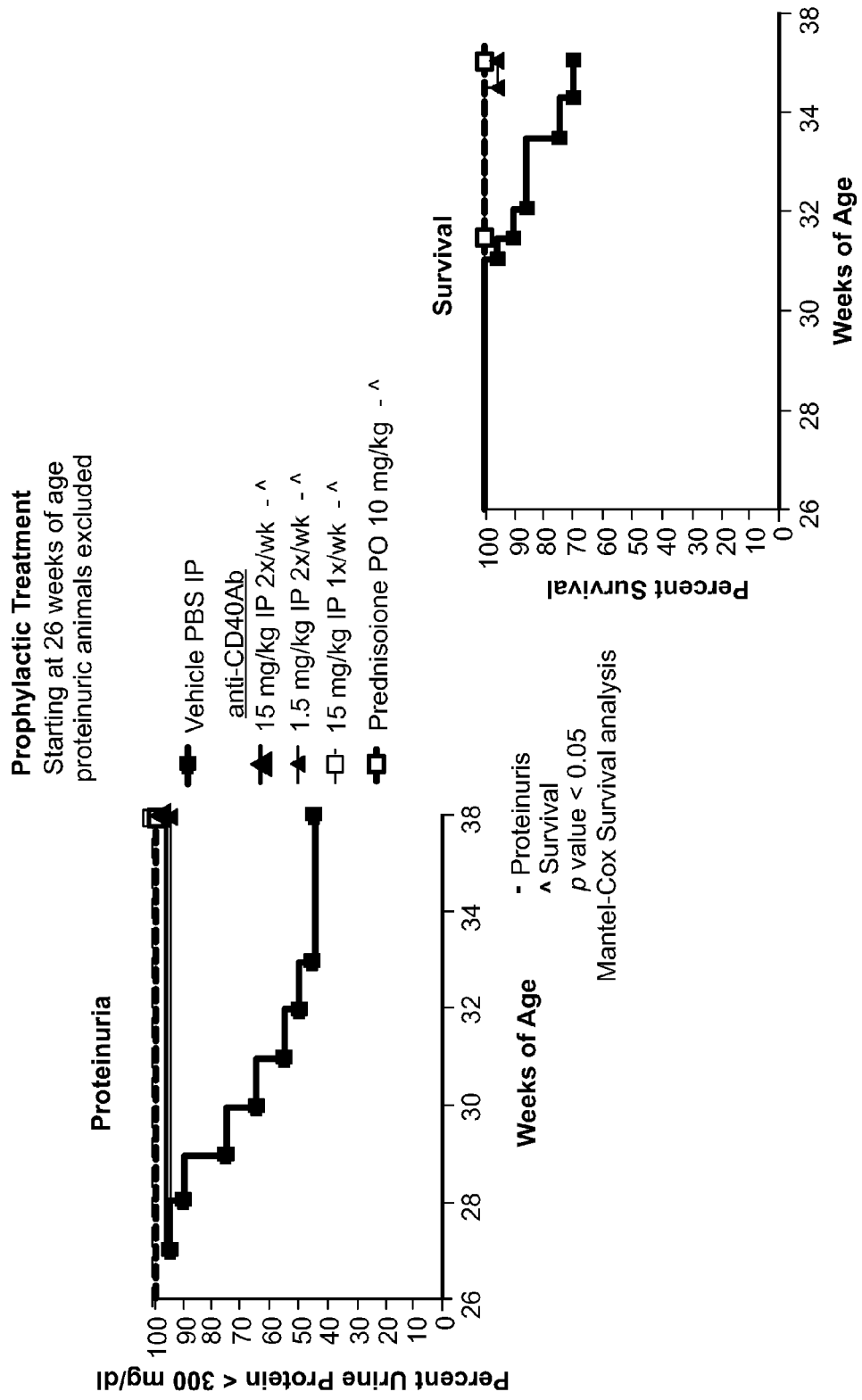
FIG. 17B is a graph that shows prophylactic dosing of anti-CD40 antibody 138 extended survival using an SLE mouse model. Prophlyactic treatment was started in mice at 26 weeks of age, and proteinuric mice were excluded from the study. Mice were dosed with 15 mg/kg of antibody 2×/week, 1.5 mg·kg of antibody 2×/week or 15 mg/kg antibody 1×/week. Administration of PBS vehicle alone was used as a control. Percent survival was assessed through 36 weeks of age.

Proteinuria was monitored weekly and as shown in FIG. 17A, where about 50% of untreated control mice were proteinuric by 32 weeks of age. In contrast, only 1 of the anti-CD40 antibody 138 treated mice and none of the prednisolone treated mice developed high proteinuria. These results were significant from untreated controls. Survival, as shown in FIG. 17B, mirrored the proteinuria finding with all treatments significantly different from PBS controls. Thus, both the 15 and 1.5 mg/kg treatment doses prevented proteinuria and extended survival.

Therapeutic Treatment

Figure 18A:
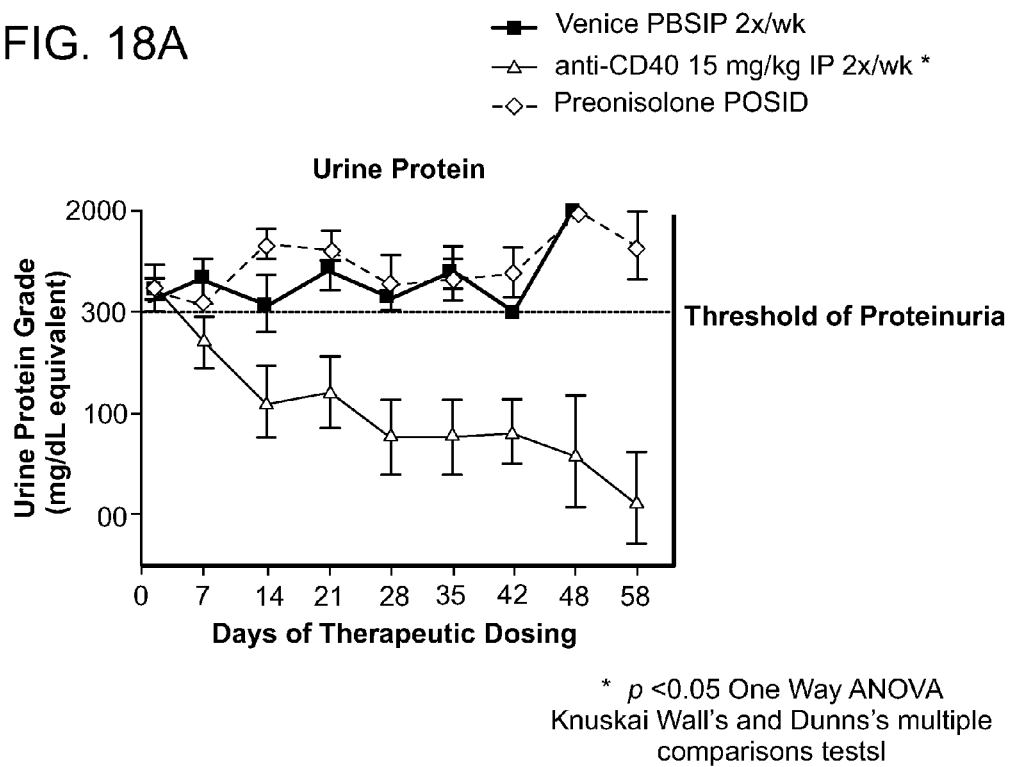
FIG. 18A is a graph that shows that mice treated with antibody 138 at a dose of 15 mg/kg IP 2×/week, developed low proteinuria over time, as shown by the urine protein grade (mg/dL equivalent). Vehicle PBS administered IP, 2×/week was used as a control. Prednisolone was given at a dose of 10 mg/kg orally (PO), once a day (SID). Neither the vehicle PBS untreated control mice nor the prednisolone treated mice developed low proteinuria. The threshold of proteinuria is indicated as 300 mg/dL.
Figure 18B:
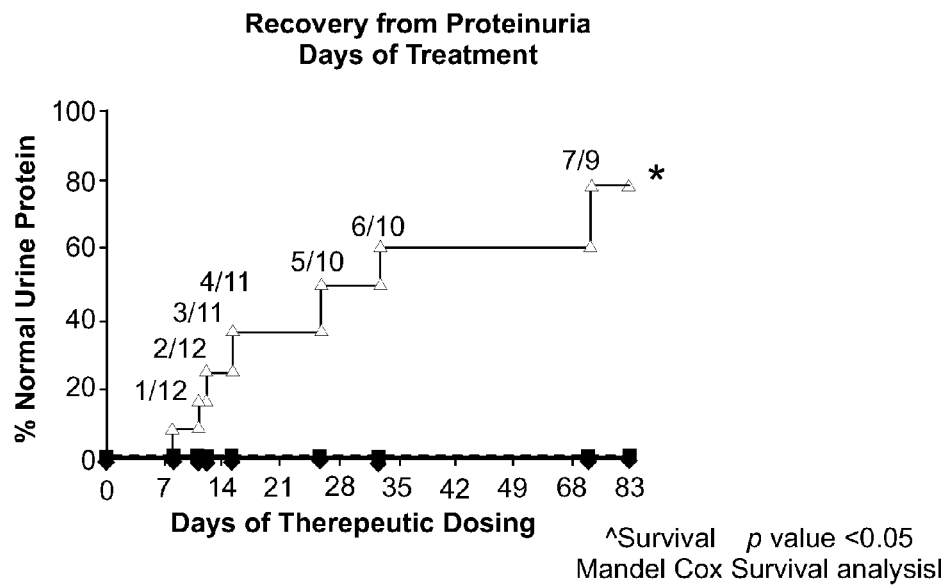
FIG. 18B is a graph that shows the rate of recovery from proteinuria in mice treated with antibody 138 at a dose of 15 mg/kp IP 2×/week. Based on the rate of recovery from proteinuria as determined by percent normal urine protein, the average time to recovery of proteinuria was 23±7 days. Vehicle PBS administered IP, 2×/week was used as a control. Prednisolone was given at a dose of 10 mg/kg orally (PO), once a day (SID).
Figure 18C:
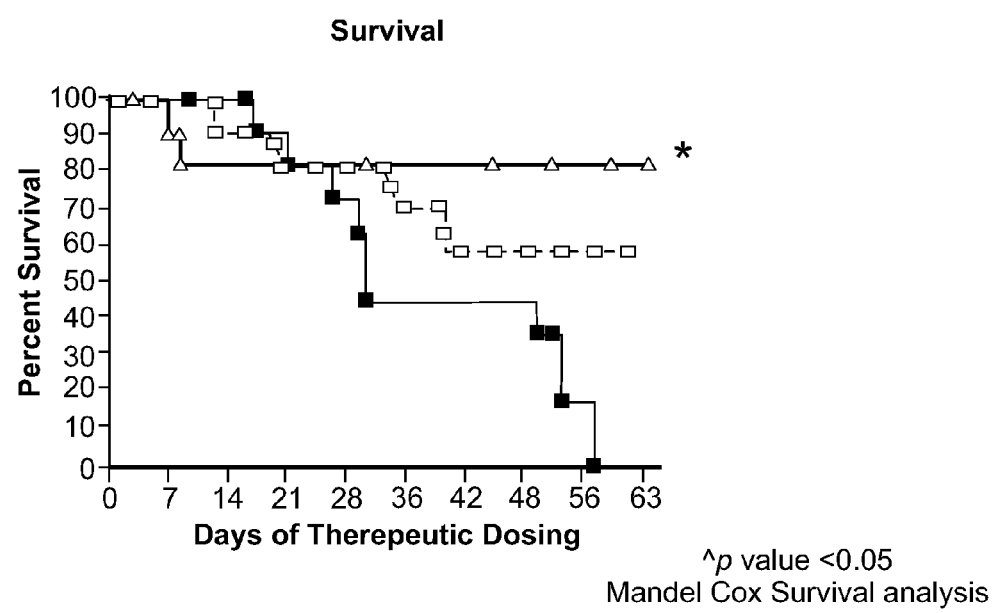
FIG. 18C is a graph that shows that mice treated with anti-CD40 antibody 138 at a dose of 15 mg/kp IP 2×/week, significantly extended survival, as shown by percent survival. Vehicle PBS administered IP, 2×/week was used as a control. Prednisolone was given orally (PO), once a day (SID).

Therapeutic treatment with anti-CD40 antibody 138 was also efficacious in this second mouse SLE model. As shown in FIG. 18A and FIG. 18B, mice treated with anti-CD40 antibody 138 developed low proteinuria over time, whereas neither the untreated control mice nor the prednisolone treated mice developed low proteinuria. Based on the rate of recovery from proteinuria, as shown in FIG. 18B, it is estimated that the average time to recovery of proteinuria was 23±7 days. Anti-CD40 antibody 138 treatment also significantly extended survival, as described in FIG. 18C.

Saliva Output

Figure 19A:
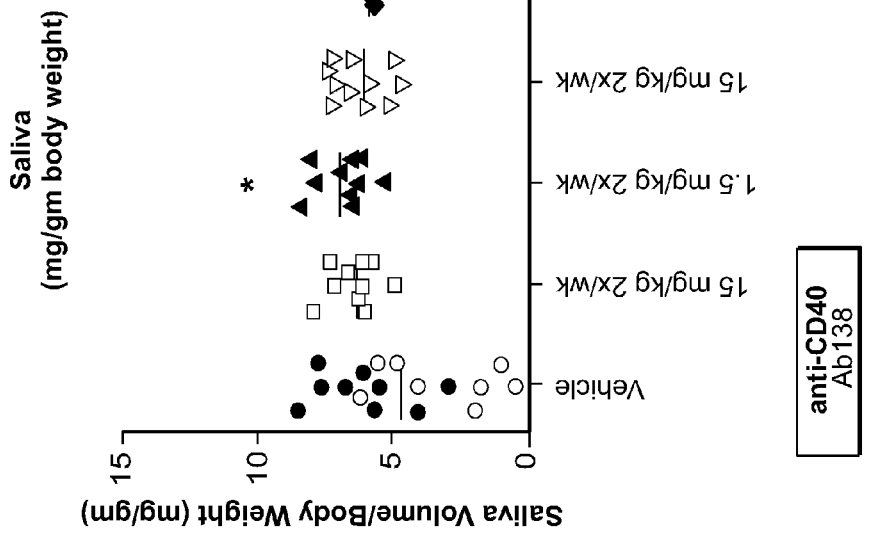
FIG. 19A is a graph that shows that saliva production is preserved by prophylactic treatment with antibody 138 at a dose of 15 mg/kp IP 2×/week, 1.5 mg/kg 2×/week, 15 mg/kg 1×/week. Vehicle PBS was used as a control. Prednisolone was administered at a dose of 10 mg/kg. Saliva production in 7 week old NZBWF-1 mice, which are non-diseased younger mice, was used as a further comparison. Amount of saliva (mg) was determined. Saliva production by anti-CD40 treated mice was comparatively uniform.
Figure 19B:
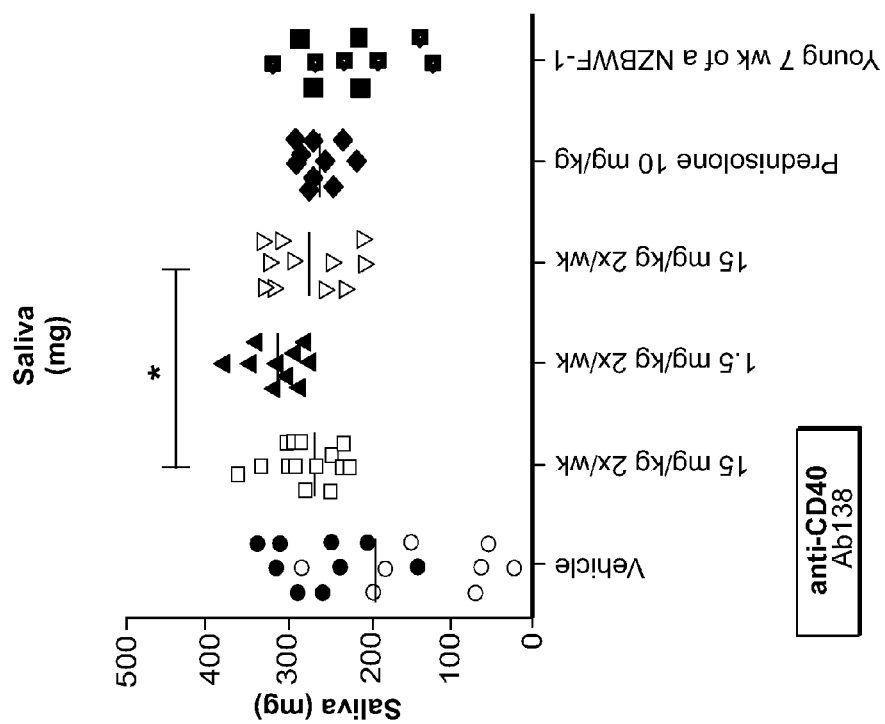
FIG. 19B is a graph that shows that saliva volume is preserved by prophylactic treatment with anti-CD40 antibody 138 at a dose of 15 mg/kp IP 2×/week, 1.5 mg/kg 2×/week, 15 mg/kg 1×/week. Vehicle PBS was used as a control. Prednisolone was administered at a dose of 10 mg/kg. Saliva volume/body weight (mg/gm) was determined. Saliva production by anti-CD40 antibody treated mice was significantly greater than in untreated control mice.

Saliva production was measured in both prophylactically and therapeutically treated mice to assess salivary gland function. Anesthetized mice were administered pilocarpine nitrate and over an 8 minute period saliva was collected on a cotton swab. Saliva output was measured as the net weight increase of the cotton swab. In the prophylactic study, it was found that saliva production by untreated control mice was highly variable, but significantly different from that of NZBWF-1 non-diseased younger mice, as described in FIGS. 19A and 19B. The variability was likely due to the level of disease since the majority of vehicle control mice with the lowest saliva production were proteinuric (FIGS. 19A and 19B, purple vs black in vehicle group). Importantly, however, saliva production by anti-CD40 antibody 138 treated mice was comparatively uniform (FIG. 19A) and significantly greater than in untreated control mice. Although all anti-CD40 antibody 138 treated cohorts had higher saliva production, only the 1.5 mg/kg treated cohort retained significance when measured as a function of body weight (FIG. 19B). Nevertheless, these data indicate that prophylactic anti-CD40 antibody 138 treatment can prevent the loss of salivary gland function.

Figure 20A:
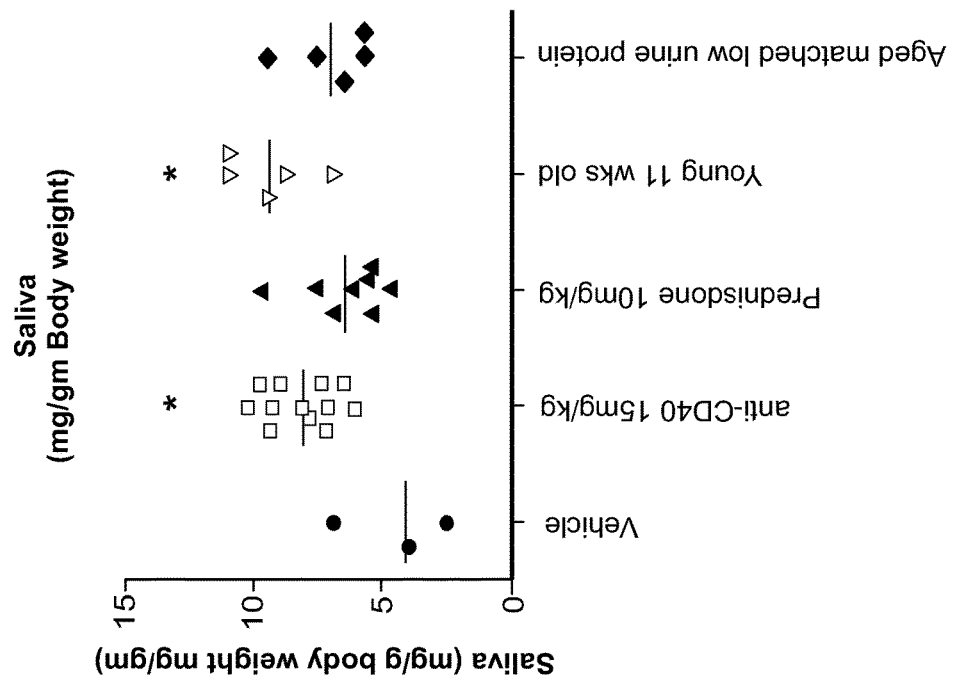
FIG. 20A is a graph that shows that saliva production was preserved by therapeutic treatment with anti-CD40 antibody 138 at a dose of 15 mg/kg. Prednisolone was administered at a dose of 10 mg/kg. Saliva production in 11 week old mice was used as a further comparison. Amount of saliva (mg) was determined.
Figure 20B:
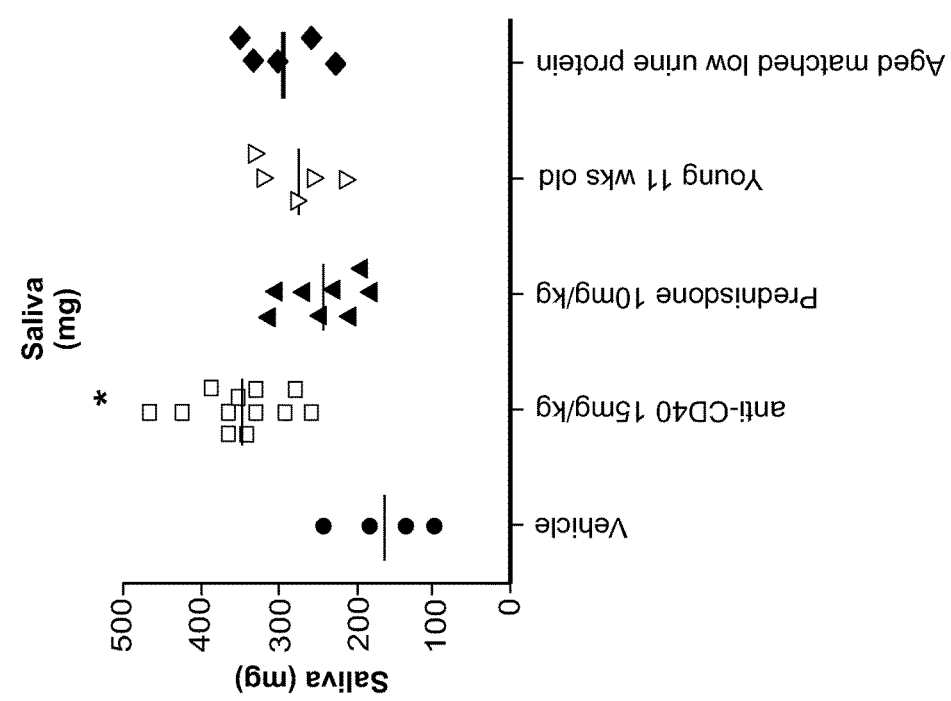
FIG. 20B is a graph that shows that saliva production is preserved by therapeutic treatment with anti-CD40 antibody 138 at a dose of 15 mg/kg. Prednisolone was administered at a dose of 10 mg/kg. Saliva production in 11 week old mice was used as a further comparison. Saliva volume/body weight (mg/gm) was determined.

In therapeutically treated mice, it was found that anti-CD40 antibody 138 treated mice had significantly higher saliva production than untreated controls (FIGS. 20 A and 20B). FIGS. 20 A and 20B show that saliva production was preserved by therapeutic dosing of anti-CD40 antibody. This was evident whether considering total saliva or saliva normalized for body weight. Notably, the untreated mice were all proteinuric, whereas none of the anti-CD40 antibody treated mice were proteinuric. It can therefore be concluded that therapeutic dosing of an antagonist anti-CD40 antibody that is substantially free of agonist activity, prevents or reverses the decline in salivary gland function.

This study indicates that antagonist anti-CD40 antibody 138 was efficacious in preventing the development of nephritis in the lupus-prone NZB/W-F1 mice and in rescuing these mice from nephritis. In addition, anti-CD40 antibody prevented the development of salivary gland and joint inflammation. This study supports the hypothesis that an antagonist anti-CD40 antibody that is substantially free of agonist activity will be efficacious in human SLE.

Methods used in Examples 11.1 and 11.2 included the following:

MRL/Lpr Mice

MRL/Lpr: Anti-CD40 antibody (antibody 138) was administered i.p. to 10 week old MRL/lpr mice in one of 4 doses; 15 mg/kg, 5 mg/kg, or 1.5 mg/kg twice per week, or 15 mg/kg once per week. Mice treated with PBS (vehicle) i.p. twice per week were included as a negative control, and mice treated with 10 mg/kg prednisolone PO sid were included as a positive control.

NZB/W-$F_1$: Anti-CD40 antibody 138 was administered to NZB/W-$F_1$ mice in both prophylactic and therapeutic regimens. For the prophylactic regimen, mice were given anti-CD40 i.p. beginning at 26 weeks of age in either of two doses, twice per week at 15 mg/kg or 1.5 mg/kg. Mice given prednisolone at 10 mg/kg PO sid or given PBS served as positive and negative controls, respectively. Mice were tested for proteinuria at the outset and any mice with ≥300 mg/dL were excluded from the prophylactic study. For the therapeutic regimen, mice began treatment as they developed proteinuria of ≥300 mg/dL. Mice received anti-CD40 i.p. at 15 mg/kg twice per week. Mice given prednisolone at 10 mg/kg PO sid, or PBS served as positive and negative controls, respectively.

Proteinuria

Urine was tested weekly for protein level using Albustix reagent strips (Siemens 2191, Pittsburgh, Pa.). Mice were considered proteinuric when urine protein levels increased to ≥300 mg/dL for at least 2 consecutive tests or prior to death or euthanasia.

Flow Cytometry

Splenic single cell suspensions were made in Hanks buffered salt solution (Invitrogen) with 1% heat inactivated fetal bovine serum (Invitrogen) and 1× penicillin/streptomycin (Sigma, St Louis, Mo.). Erythrocytes were removed by centrifugation and the cells resuspended in staining buffer (PBS (Invitrogen) with 1.5% heat inactivated fetal bovine serum and 0.02% sodium azide (Sigma)). Cells were stained with antibodies against CD3 (145-2011, BD), CD4 (GK1.5 eBioSciences), ICOS (C398.4A, Biolegend), CXCR5 (L138D7, Biolegend), PD-1 (29F.1A12, Biolegend), GL7 (A488, Biolegend), CD19 (BUV395, BD), CD95 (Jo2, Biolegend). Antibodies were directly couple to fluorescein isothiocyanate, phycoerythrin, phycoerythrin and cyanine 5, allophycocyanin, peridinin chlorophylla and cyanine 5.5, or biotin. Total B cells were identified as CD19+; GC B cells as CD19+, CD95+, and GL7+; Tfh cells as CD3+, CD4+, ICOS+, CXCR5+, and PD-1+. Cells were analyzed by a FACSCalibur (BD Biosciences) flow cytometer and analyzed with FlowJo software (version 8.5, Treestar Inc.).

Histology

As vehicle control mice became moribund, kidney, ankle and salivary gland tissues were collected and fixed in 10% neutral buffered formalin. In addition, at specific intermediate time points these same tissues and blood were collected from representative mice of each group. Tissues were fixed in 10% neutral-buffered formalin for 8 hours, processed and paraffin-embedded for H&E. Inflammatory infiltrates were evaluated in the kidney, salivary gland, and ankle based on evaluation of routine H&E stained formalin-fixed paraffin embedded (FFPE) sections. For the kidney, a pathologist scored 3 um H&E sections on a 0 to 4 scale for glomerular disease, perivascular infiltration, and tubulointerstitial infiltration based on the following scoring criteria: Glomerular disease: 0=no disease; 1=segmental thickening of mesangium in occasional glomeruli; 2=segmental to diffuse thickening of mesangium in most glomeruli; 3=diffuse thickening of the mesangium, hypercellularity, enlarged podocytes, no adhesions; 4=diffuse thickening of the mesangium with areas worse than others with one or more of the following: coagulated proteins, fibrosis, hypocellularity, enlarged podocytes, adhesions and crescents of Bowman's capsule. Perivascular renal inflammation: 0=up to a few rare lymphocytes; 1=few lymphocytes forming loose aggregates; 2=lymphocytes forming discrete small aggregates; 3=polarized aggregate of lymphocytes that bulge into the lumen of the adjacent vein but fail to fully surround the arcuate artery; 4=lymphocyte aggregates fully surrounding the arcuate artery without polarization. Tubulointerstitial (TI) infiltration: 0=no infiltrates; 1=minimal to mild TI infiltrates; 2=mild infiltrates between 20% of tubules; 3=mild to moderate infiltrates between up to 50% of tubules; 4=moderate infiltrates between and surrounding >50% tubules throughout renal cortex. Salivary and joint inflammation scores were based on the same principles with a 0-4 score of increasing infiltrates within the tissue.

Saliva Output

To measure salivary gland output, mice were first sedated with oxygen/isoflurane in a small isolation chamber. After sedation mice were i.p. administered 30 ul (60 ug) of pilocarpine nitrate (Sigma). Two minutes after injection, pre-weighed children's safety swabs (trimmed to ~1.5 cm, cotton plus stem) were placed in the animals mouth behind the front teeth. Mice were placed on their sides to allow pooling of saliva in the cheek and adsorption by the cotton swab. After 8 minutes the swabs were removed and weighed to calculate the net saliva weight.

ELISA

Total circulating IgG and IgM levels were determined by ELISA using eBioscience kits (cat #88-50400, 88-50470) according to the manufacturer's instructions.

| SEQUENCE SUMMARY | | |
|---|---|---|
| Sequence Identifier | Protein | Sequence |
| SEQ ID NO: 1 | Human CD40 | MVRLPLQCVLWGCLLTAVHPEPPTACREKQYLIN SQCCSLCQPGQKLVSDCTEFTETECLPCGESEFL DTWNRETHCHQHKYCDPNLGLRVQQKGTSETDTI CTCEEGWHCTSEACESCVLHRSCSPGFGVKQIAT GVSDTICEPCPVGFFSNVSSAFEKCHPWTSCETK DLVVQQAGTNKTDVVCGPQDRLRALVVIPIIFGI LFAILLVLVFIKKVAKKPTNKAPHPKQEPQEINF PDDLPGSNTAAPVQETLHGCQPVTQEDGKESRIS VQERQ |
| SEQ ID NO: 2 | Human Ig gamma-1 constant region | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |

SEQUENCE SUMMARY

| Sequence Identifier | Protein | Sequence |
|---|---|---|
| SEQ ID NO: 3 | Human Ig gamma-1 constant region mutant | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPEAAGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| SEQ ID NO: 4 | Human Ig Kappa constant region | TVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFN RGEC |
| SEQ ID NO: 5 | Variable heavy chain of: Ab1 (murine) (CDRs in bold) | EVQLVESGGGLVKPGGSLKVSCAASGFTFSDYGM NWVRQAPEKGLEWIAYISSGRSNIYYADTVKGRF TISRDNAKNTLFLQMTSLRSEDTAMYYCARSWGY FDVWGTGTTVTVSS |
| SEQ ID NO: 6 | Heavy chain CDR1 of: Ab1 (murine) Ab2 (murine) huAb1v1CDR2v1 to huAb1v1CDR2v17 huAb1v1 huAb1v5 huAb1v6 huAb1v4 huAb1v3 Ab101 Ab102 | GFTFSDYGMN |
| SEQ ID NO: 7 | Heavy chain CDR2 of: Ab1 (murine) huAb1VH.1/VL.1 huAb1v1 huAb1v5 huAb1v3 huAb1v4 | YISSGRSNIYYADTVKG |
| SEQ ID NO: 8 | Heavy chain CDR3 of: Ab2 (murine) Ab1 (murine) huAb1VH.1/VL.1 huAb1VH.1A/VL.1 huAb1VH.1A/VL.1A huAb1v1 huAb1v1CDR2v1 to huAb1v1CDR2v17 huAb1v5 huAb1v6 huAb1v2 huAb1v3 huAb1v4 Ab101 Ab102 | SWGYFDV |
| SEQ ID NO: 9 | Variable light chain of: Ab1 (murine) | DIVMTQSPSSLTVTAGEMVTMSCKSSQSLLNSGN QKNYLTWFQQKPGQPPKLLIYWASTRESGVPDRF AGSGSGTDFTLTISSVQAEDLAVYYCQNDYTYPL TFGAGTKLEIK |
| SEQ ID NO: 10 | Light chain CDR1 of: Ab2 (murine) Ab1 (murine) huAb1VH1/VL.1 huAb1VH1A/VL.1 huAb1VH1A/VL.1A | KSSQSLLNSGNQKNYLT |

SEQUENCE SUMMARY

| Sequence Identifier | Protein | Sequence |
| --- | --- | --- |
| SEQ ID NO: 11 | Light chain CDR2 of:<br>Ab1 (murine)<br>Ab2 (murine)<br>huAb1VH.1A/VL.1A<br>huAb1VH.1/VL.1A<br>huAb1VH.1/VL.1<br>huAb1VH.1A/VL.1<br>huAb1v5<br>huAb1v2<br>huAb1v6<br>huAb1v1<br>huAb1v3<br>huAb1v4<br>Ab101<br>Ab102 | WASTRES |
| SEQ ID NO: 12 | Light chain CDR3 of:<br>Ab1 (murine)<br>Ab2 (murine)<br>huAb1VH.1A/VL.1A<br>huAb1VH.1/VL.1A<br>huAb1VH.1/VL.1<br>huAb1VH.1A/VL.1<br>huAb1v5<br>huAb1v2<br>huAb1v6<br>huAb1v1<br>huAb1v3<br>huAb1v4<br>Ab101<br>Ab102 | QNDYTYPLT |
| SEQ ID NO: 13 | Variable heavy chain of:<br>huAb1VH.1/VL.1<br>huAb1VH.1/VL.1A<br>huAb1v2<br>huAb1v3 | EVQLVESGGGLVKPGGSLRLSCAASGFTFSDYGM<br>NWVRQAPGKGLEWVSYISSGRSNIYYADTVKGRF<br>TISRDNAKNSLYLQMNSLRAEDTAVYYCARSWGY<br>FDVWGQGTTVTVSS |
| SEQ ID NO: 14 | Variable light chain of:<br>huAb1VH.1/VL.1<br>huAb1VH.1A/VL.1 | DIVMTQSPDSLAVSLGERATINCKSSQSLLNSGN<br>QKNYLTWYQQKPGQPPKLLIYWASTRESGVPDRF<br>SGSGSGTDFTLTISSLQAEDVAVYYCQNDYTYPL<br>TFGQGTKLEIK |
| SEQ ID NO: 15 | Variable heavy chain of:<br>huAb1VH.1A/VL.1<br>huAb1VH.1A/VL.1A<br>huAb1v1<br>huAb1v5<br>huAb1v4<br>huAb1v6 | EVQLVESGGGLVKPGGSLRLSCAASGFTFSDYGM<br>NWVRQAPGKGLEWIAYISSGRSNIYYADTVKGRF<br>TISRDNAKNSLYLQMNSLRAEDTAVYYCARSWGY<br>FDVWGQGTTVTVSS |
| SEQ ID NO: 16 | Variable light chain of:<br>huAb1VH.1A/VL.1A<br>huAb1VH.1/VL.1A | DIVMTQSPDSLAVSLGERATINCKSSQSLLNSGN<br>QKNYLTWFQQKPGQPPKLLIYWASTRESGVPDRF<br>SGSGSGTDFTLTISSLQAEDVAVYYCQNDYTYPL<br>TFGQGTKLEIK |
| SEQ ID NO: 17 | Light chain CDR1 of:<br>huAb1v6<br>huAb1v3 | KSSQSLLNLGNQKNYLT |
| SEQ ID NO: 18 | VL<br>huAb1v5<br>huAb1v2<br>(CDRs in bold) | DIVMTQSPDSLAVSLGERATINCKSSQSLLNTGN<br>QKNYLTWFQQKPGQPPKLLIYWASTRESGVPDRF<br>SGSGSGTDFTLTISSLQAEDVAVYYCQNDYTYPL<br>TFGQGTKLEIK |
| SEQ ID NO: 19 | Light chain CDR1 of:<br>huAb1v5<br>huAb1v2 | KSSQSLLNTGNQKNYLT |

SEQUENCE SUMMARY

| Sequence Identifier | Protein | Sequence |
|---|---|---|
| SEQ ID NO: 20 | Variable light chain (VL) of: huAb1v1 Ab101 Ab102 (CDRs in bold) | DIVMTQSPDSLAVSLGERATINCKSSQSLLNRGN QKNYLTWFQQKPGQPPKLLIYWASTRESGVPDRF SGSGSGTDFTLTISSLQAEDVAVYYCQNDYTYPL TFGQGTKLEIK |
| SEQ ID NO: 21 | Variable light chain CDR1 of: huAb1v1 Ab101 Ab102 | KSSQSLLNRGNQKNYLT |
| SEQ ID NO: 22 | Variable Heavy chain (VH) of: huAb1v1CDR2v1 (CDRs in bold) | EVQLVESGGGLVKPGGSLRLSCAASGFTFSDYGM NWVRQAPGKGLEWIAYISSGRTNIYYADTVKGRF TISRDNAKNSLYLQMNSLRAEDTAVYYCARSWGY FDVWGQGTTVTVSS |
| SEQ ID NO: 23 | Variable Heavy chain (VH) of: huAb1v1CDR2v2 (CDRs in bold) | EVQLVESGGGLVKPGGSLRLSCAASGFTFSDYGM NWVRQAPGKGLEWIAYISSGRDNIYYADTVKGRF TISRDNAKNSLYLQMNSLRAEDTAVYYCARSWGY FDVWGQGTTVTVSS |
| SEQ ID NO: 24 | Variable Heavy chain (VH) of: huAb1v1CDR2v3 (CDRs in bold) | EVQLVESGGGLVKPGGSLRLSCAASGFTFSDYGM NWVRQAPGKGLEWIAYISSGRENIYYADTVKGRF TISRDNAKNSLYLQMNSLRAEDTAVYYCARSWGY FDVWGQGTTVTVSS |
| SEQ ID NO: 25 | Variable Heavy chain (VH) of: huAb1v1CDR2v4 (CDRs in bold) | EVQLVESGGGLVKPGGSLRLSCAASGFTFSDYGM NWVRQAPGKGLEWIAYISSGRRNIYYADTVKGRF TISRDNAKNSLYLQMNSLRAEDTAVYYCARSWGY FDVWGQGTTVTVSS |
| SEQ ID NO: 26 | Variable Heavy chain (VH) of: huAb1v1CDR2v5 (CDRs in bold) | EVQLVESGGGLVKPGGSLRLSCAASGFTFSDYGM NWVRQAPGKGLEWIAYISSGRVNIYYADTVKGRF TISRDNAKNSLYLQMNSLRAEDTAVYYCARSWGY FDVWGQGTTVTVSS |
| SEQ ID NO: 27 | Variable Heavy chain (VH) of: huAb1v1CDR2v6 (CDRs in bold) | EVQLVESGGGLVKPGGSLRLSCAASGFTFSDYGM NWVRQAPGKGLEWIAYISSGRLNIYYADTVKGRF TISRDNAKNSLYLQMNSLRAEDTAVYYCARSWGY FDVWGQGTTVTVSS |
| SEQ ID NO: 28 | Variable Heavy chain (VH) of: huAb1v1CDR2v7 Ab101 Ab102 (CDRs in bold) | EVQLVESGGGLVKPGGSLRLSCAASGFTFSDYGM NWVRQAPGKGLEWIAYISSGRGNIYYADTVKGRF TISRDNAKNSLYLQMNSLRAEDTAVYYCARSWGY FDVWGQGTTVTVSS |
| SEQ ID NO: 29 | VH huAb1v1CDR2v8 (CDRs in bold) | EVQLVESGGGLVKPGGSLRLSCAASGFTFSDYGM NWVRQAPGKGLEWIAYISSGRINIYYADTVKGRF TISRDNAKNSLYLQMNSLRAEDTAVYYCARSWGY FDVWGQGTTVTVSS |
| SEQ ID NO: 30 | Variable Heavy chain (VH) of: huAb1v1CDR2v9 (CDRs in bold) | EVQLVESGGGLVKPGGSLRLSCAASGFTFSDYGM NWVRQAPGKGLEWIAYISSGRQNIYYADTVKGRF TISRDNAKNSLYLQMNSLRAEDTAVYYCARSWGY FDVWGQGTTVTVSS |
| SEQ ID NO: 31 | Variable Heavy chain (VH) of: huAb1v1CDR2v10 (CDRs in bold) | EVQLVESGGGLVKPGGSLRLSCAASGFTFSDYGM NWVRQAPGKGLEWIAYISSGRWNIYYADTVKGRF TISRDNAKNSLYLQMNSLRAEDTAVYYCARSWGY FDVWGQGTTVTVSS |
| SEQ ID NO: 32 | Variable Heavy chain (VH) of: huAb1v1CDR2v11 (CDRs in bold) | EVQLVESGGGLVKPGGSLRLSCAASGFTFSDYGM NWVRQAPGKGLEWIAYISSGRMNIYYADTVKGRF TISRDNAKNSLYLQMNSLRAEDTAVYYCARSWGY FDVWGQGTTVTVSS |
| SEQ ID NO: 33 | Variable Heavy chain (VH) of: huAb1v1CDR2v12 (CDRs in bold) | EVQLVESGGGLVKPGGSLRLSCAASGFTFSDYGM NWVRQAPGKGLEWIAYISSGRKNIYYADTVKGRF TISRDNAKNSLYLQMNSLRAEDTAVYYCARSWGY FDVWGQGTTVTVSS |

SEQUENCE SUMMARY

| Sequence Identifier | Protein | Sequence |
|---|---|---|
| SEQ ID NO: 34 | Variable Heavy chain (VH) of: huAb1v1CDR2v13 (CDRs in bold) | EVQLVESGGGLVKPGGSLRLSCAASGFTFSDYGM NWVRQAPGKGLEWIAYISSGRHNIYYADTVKGRF TISRDNAKNSLYLQMNSLRAEDTAVYYCARSWGY FDVWGQGTTVTVSS |
| SEQ ID NO: 35 | Variable Heavy chain (VH) of: huAb1v1CDR2v14 (CDRs in bold) | EVQLVESGGGLVKPGGSLRLSCAASGFTFSDYGM NWVRQAPGKGLEWIAYISSGRFNIYYADTVKGRF TISRDNAKNSLYLQMNSLRAEDTAVYYCARSWGY FDVWGQGTTVTVSS |
| SEQ ID NO: 36 | Variable Heavy chain (VH) of: huAb1v1CDR2v15 (CDRs in bold) | EVQLVESGGGLVKPGGSLRLSCAASGFTFSDYGM NWVRQAPGKGLEWIAYISSGRYNIYYADTVKGRF TISRDNAKNSLYLQMNSLRAEDTAVYYCARSWGY FDVWGQGTTVTVSS |
| SEQ ID NO: 37 | Variable Heavy chain (VH) of: huAb1v1CDR2v16 (CDRs in bold) | EVQLVESGGGLVKPGGSLRLSCAASGFTFSDYGM NWVRQAPGKGLEWIAYISSGRANIYYADTVKGRF TISRDNAKNSLYLQMNSLRAEDTAVYYCARSWGY FDVWGQGTTVTVSS |
| SEQ ID NO: 38 | Variable Heavy chain (VH) of: huAb1v1CDR2v17 (CDRs in bold) | EVQLVESGGGLVKPGGSLRLSCAASGFTFSDYGM NWVRQAPGKGLEWIAYISSGRPNIYYADTVKGRF TISRDNAKNSLYLQMNSLRAEDTAVYYCARSWGY FDVWGQGTTVTVSS |
| SEQ ID NO: 39 | Heavy chain sequence Ab101 (constant region is underlined; CDRs in bold) | EVQLVESGGGLVKPGGSLRLSCAASGFTFSDYGM NWVRQAPGKGLEWIAYISSGRGNIYYADTVKGRF TISRDNAKNSLYLQMNSLRAEDTAVYYCARSWGY FDVWGQGTTVTVSS<u>ASTKGPSVFPLAPSSKSTSG GTAALGCLVKDYFPEPVTVSWNSGALTSGVHTFP AVLQSSGLYSLSSVVTVPSSSLGTQTYICNVNHK PSNTKVDKKVEPKSCDKTHTCPPCPAPEAAGGPS VFLFPPKPKDTLMISRTPEVTCVVVDVSHEDPEV KFNWYVDGVEVHNAKTKPREEQYNSTYRVVSVLT VLHQDWLNGKEYKCKVSNKALPAPIEKTISKAKG QPREPQVYTLPPSREEMTKNQVSLTCLVKGFYPS DIAVEWESNGQPENNYKTTPPVLDSDGSFFLYSK LTVDKSRWQQGNVFSCSVMHEALHNHYTQKSLSL SPGK</u> |
| SEQ ID NO: 40 | Light chain sequence Ab101 Light chain sequence Ab102 Humanized (constant region is underlined; CDRs in bold) | DIVMTQSPDSLAVSLGERATINCKSSQSLLNRGN QKNYLTWFQQKPGQPPKLLIYWASTRESGVPDRF SGSGSGTDFTLTISSLQAEDVAVYYCQNDYTYPL TFGQGTKLEIK<u>RTVAAPSVFIFPPSDEQLKSGTA SVVCLLNNFYPREAKVQWKVDNALQSGNSQESVT EQDSKDSTYSLSSTLTLSKADYEKHKVYACEVTH QGLSSPVTKSFNRGEC</u> |
| SEQ ID NO: 41 | Heavy chain sequence Ab102 Humanized (constant region is underlined; CDRs in bold) | EVQLVESGGGLVKPGGSLRLSCAASGFTFSDYGM NWVRQAPGKGLEWIAYISSGRGNIYYADTVKGRF TISRDNAKNSLYLQMNSLRAEDTAVYYCARSWGY FDVWGQGTTVTVSS<u>ASTKGPSVFPLAPSSKSTSG GTAALGCLVKDYFPEPVTVSWNSGALTSGVHTFP AVLQSSGLYSLSSVVTVPSSSLGTQTYICNVNHK PSNTKVDKKVEPKSCDKTHTCPPCPAPEAAGGPS VFLFPPKPKDQLMISRTPEVTCVVVDVSHEDPEV KFNWYVDGVEVHNAKTKPREEQYNSTYRVVSVLT VLHQDWLNGKEYKCKVSNKALPAPIEKTISKAKG QPREPQVYTLPPSREEMTKNQVSLTCLVKGFYPS DIAVEWESNGQPENNYKTTPPVLDSDGSFFLYSK LTVDKSRWQQGNVFSCSVLHEALHNHYTQKSLSL SPGK</u> |
| SEQ ID NO: 42 | Heavy chain CDR2 of: Ab2 huAb1v1CDR2v7 Ab101 Ab102 | YISSGRGNIYYADTVKG |

SEQUENCE SUMMARY

| Sequence Identifier | Protein | Sequence |
|---|---|---|
| SEQ ID NO: 43 | Variable light chain of: huAb1v6 huAb1v3 (CDRs in bold) | DIVMTQSPDSLAVSLGERATINCKSSQSLLNLGN QKNYLTWFQQKPGQPPKLLIYWASTRESGVPDRF SGSGSGTDFTLTISSLQAEDVAVYYCQNDYTYPL TFGQGTKLEIK |
| SEQ ID NO: 44 | Variable heavy chain of: Ab3 (murine) (CDRs in bold) | QVQLQQSGAELARPGASVKMSCKAFGYTFTSYTM HWVKQRPGQGLEWIGYINPSSDYPNYNQKFKDKA TLTADKSSTAYMQLSSLTSEDSAVYYCARWGYS FDYWGQGTTLTVSS |
| SEQ ID NO: 45 | Heavy chain CDR1 of: Ab3 (murine) huAb3VH.1/VL.1 huAb3VH.1/VL.1A huAb3VH.1/VL.1B huAb3VH.1B/VL.1 huAb3VH.1B/VL.1A huAb3VH.1B/VL.1B huAb3VH.1A/VL.1 huAb3VH.1A/VL.1A huAb3VH.1A/VL.1B | GYTFTSYTMH |
| SEQ ID NO: 46 | Heavy chain CDR2 of: Ab3 (murine) huAb3VH.1/VL.1 huAb3VH.1/VL.1A huAb3VH.1/VL.1B huAb3VH.1B/VL.1 huAb3VH.1B/VL.1A huAb3VH.1B/VL.1B huAb3VH.1A/VL.1 huAb3VH.1A/VL.1A huAb3VH.1A/VL.1B | YINPSSDYPNYNQKFKD |
| SEQ ID NO: 47 | Heavy chain CDR3 of: Ab3 (murine) huAb3VH.1/VL.1 huAb3VH.1/VL.1A huAb3VH.1/VL.1B huAb3VH.1B/VL.1 huAb3VH.1B/VL.1A huAb3VH.1B/VL.1B huAb3VH.1A/VL.1 huAb3VH.1A/VL.1A huAb3VH.1A/VL.1B | WGYSFDY |
| SEQ ID NO: 48 | Variable light chain of: Ab3 (murine) (CDRs in bold) | DIVMTQAAPSVSVIPGESVSISCRSSKSLLHSNG NTYLYWFLQRPGQSPQYLIYRMSTLASGVPDRFS GSGSGTAFTLRISRVEAEDVGVYYCMQHLEYPLT FGAGTKLELK |
| SEQ ID NO: 49 | Light chain CDR1 of: Ab3 (murine) huAb3VH.1/VL.1 huAb3VH.1B/VL.1 huAb3VH.1A/VL.1 huAb3VH.1/VL.1A huAb3VH.1B/VL.1A huAb3VH.1A/VL.1A huAb3VH.1/VL.1B huAb3VH.1B/VL.1B huAb3VH.1A/VL.1B | RSSKSLLHSNGNTYLY |

SEQUENCE SUMMARY

| Sequence Identifier | Protein | Sequence |
|---|---|---|
| SEQ ID NO: 50 | Light chain CDR2 of: Ab3 (murine) huAb3VH.1/VL.1 huAb3VH.1B/VL.1 huAb3VH.1A/VL.1 huAb3VH.1/VL.1A huAb3VH.1B/VL.1A huAb3VH.1A/VL.1A huAb3VH.1/VL.1B huAb3VH.1B/VL.1B huAb3VH.1A/VL.1B | RMSTLAS |
| SEQ ID NO: 51 | Light chain CDR3 of: Ab3 (murine) huAb3VH.1/VL.1 huAb3VH.1B/VL.1 huAb3VH.1A/VL.1 huAb3VH.1/VL.1A huAb3VH.1B/VL.1A huAb3VH.1A/VL.1A huAb3VH.1/VL.1B huAb3VH.1B/VL.1B huAb3VH.1A/VL.1B | MQHLEYPLT |
| SEQ ID NO: 52 | Variable heavy chain of: huAb3VH.1/VL.1 huAb3VH.1/VL.1A huAb3VH.1/VL.1B | EVQLVQSGAEVKKPGSSVKVSCKASGYTFTSYTM HWVRQAPGQGLEWMGYINPSSDYPNYNQKFKDRV TITADKSTSTAYMELSSLRSEDTAVYYCARWGYS FDYWGQGTTVTSS |
| SEQ ID NO: 53 | Variable light chain of: huAb3VH.1/VL.1 huAb3VH.1B/VL.1 huAb3VH.1A/VL.1 (CDRs in bold) | DIVMTQSPLSLPVTPGEPASISCRSSKSLLHSNG NTYLYWYLQKPGQSPQLLIYRMSTLASGVPDRFS GSGSGTDFTLKISRVEAEDVGVYYCMQHLEYPLT FGQGTKLEIK |
| SEQ ID NO: 54 | Variable heavy chain of: huAb3VH.1B/VL.1 huAb3VH.1B/VL.1A huAb3VH.1B/VL.1B (CDRs in bold) | EVQLVQSGAEVKKPGSSVKVSCKASGYTFTSYTM HWVRQAPGQGLEWMGYINPSSDYPNYNQKFKDRV TLTADKSTSTAYMELSSLRSEDTAVYYCARWGYS FDYWGQGTTVTSS |
| SEQ ID NO: 55 | Variable heavy chain of: huAb3VH.1A/VL.1 huAb3VH.1A/VL.1A huAb3VH.1A/VL.1B (CDRs in bold) | EVQLVQSGAEVKKPGSSVKVSCKASGYTFTSYTM HWVRQAPGQGLEWIGYINPSSDYPNYNQKFKDRA TLTADKSTSTAYMELSSLRSEDTAVYYCARWGYS FDYWGQGTTVTSS |
| SEQ ID NO: 56 | Variable light chain of: huAb3VH.1/VL.1A huAb3VH.1B/VL.1A huAb3VH.1A/VL.1A (CDRs in bold) | DIVMTQSPLSLPVTPGEPASISCRSSKSLLHSNG NTYLYWFLQKPGQSPQYLIYRMSTLASGVPDRFS GSGSGTDFTLKISRVEAEDVGVYYCMQHLEYPLT FGQGTKLEIK |
| SEQ ID NO: 57 | Variable light chain of: huAb3VH.1/VL.1B huAb3VH.1B/VL.1B huAb3VH.1A/VL.1B (CDRs in bold) | DIVMTQSPLSLPVTPGEPASISCRSSKSLLHSNG NTYLYWYLQKPGQSPQYLIYRMSTLASGVPDRFS GSGSGTDFTLKISRVEAEDVGVYYCMQHLEYPLT FGQGTKLEIK |
| SEQ ID NO: 58 | Heavy chain CDR2 of: huAb1v1CDR2v1 | YISSGRTNIYYADTVKG |

-continued

| Sequence Identifier | Protein | Sequence |
|---|---|---|
| SEQ ID NO: 59 | Heavy chain CDR2 of: huAb1v1CDR2v2 | YISSGRDNIYYADTVKG |
| SEQ ID NO: 60 | Heavy chain CDR2 of: huAb1v1CDR2v3 | YISSGRENIYYADTVKG |
| SEQ ID NO: 61 | Heavy chain CDR2 of: huAb1v1CDR2v4 | YISSGRRNIYYADTVKG |
| SEQ ID NO: 62 | Heavy chain CDR2 of: huAb1v1CDR2v5 | YISSGRVNIYYADTVKG |
| SEQ ID NO: 63 | Heavy chain CDR2 of: huAb1v1CDR2v6 | YISSGRLNIYYADTVKG |
| SEQ ID NO: 64 | Heavy chain CDR2 of: huAb1v1CDR2v8 | YISSGRINIYYADTVKG |
| SEQ ID NO: 65 | Heavy chain CDR2 of: huAb1v1CDR2v9 | YISSGRQNIYYADTVKG |
| SEQ ID NO: 66 | Heavy chain CDR2 of: huAb1v1CDR2v10 | YISSGRWNIYYADTVKG |
| SEQ ID NO: 67 | Heavy chain CDR2 of: huAb1v1CDR2v11 | YISSGRMNIYYADTVKG |
| SEQ ID NO: 68 | Heavy chain CDR2 of: huAb1v1CDR2v12 | YISSGRKNIYYADTVKG |
| SEQ ID NO: 69 | Heavy chain CDR2 of: huAb1v1CDR2v13 | YISSGRHNIYYADTVKG |
| SEQ ID NO: 70 | Heavy chain CDR2 of: huAb1v1CDR2v14 | YISSGRFNIYYADTVKG |
| SEQ ID NO: 71 | Heavy chain CDR2 of: huAb1v1CDR2v15 | YISSGRYNIYYADTVKG |
| SEQ ID NO: 72 | Heavy chain CDR2 of: huAb1v1CDR2v16 | YISSGRANIYYADTVKG |
| SEQ ID NO: 73 | Heavy chain CDR2 of: huAb1v1CDR2v17 | YISSGRPNIYYADTVKG |
| SEQ ID NO: 74 | Light chain CDR1 of: huAb1v4 | KSSQSLLNPGNQKNYLT |
| SEQ ID NO: 75 | Variable heavy chain of: Ab2 (murine) (CDRs in bold) | EVQLVESGGGLVKPGGSLKVSCAASGFTFSDYGM NWVRQSPEKGLEWIAYISSGRGNIYYADTVKGRF TISRDNAKNTLFLQMTSLRSEDTAMYYCARSWGY FDVWGTGTTVTVSS |
| SEQ ID NO: 76 | Variable light chain of: Ab2 (murine) (CDRs in bold) | DIVMTQSPSSLTVTAGEKVTMSCKSSQSLLNSGN QKNYLTWFQQKPGQPPKLLIYWASTRESGVPDRF TGSGSGTDFTLTISSVQAEDLAVYYCQNDYTYPL TFGAGTKLELK |

-continued

| SEQUENCE SUMMARY | | |
|---|---|---|
| Sequence Identifier | Protein | Sequence |
| SEQ ID NO: 77 | Variable light chain of: huAb1v4 | DIVMTQSPDSLAVSLGERATINCKSSQSLLNPGN QKNYLTWFQQKPGQPPKLLIYWASTRESGVPDRF SGSGSGTDFTLTISSLQAEDVAVYYCQNDYTYPL TFGQGTKLEIK |
| SEQ ID NO: 78 | Consensus sequence of Variable heavy chain CDR1 | G(F/Y)TF(S/T) (D/S)Y(G/T)M(N/H) |
| SEQ ID NO: 79 | Consensus sequence of Variable heavy chain CDR2 | YI(S/N) (S/P) (G/S) (R/S) (D/S/G) (N/Y) (I/P) (Y/N)Y(A/N) (D/Q) (T/K) (V/F)K (G/D) |
| SEQ ID NO: 80 | Consensus sequence of Variable heavy chain CDR3 | (S/W) (W/G) (G/Y) (Y/S)FDV |
| SEQ ID NO: 81 | Human Ig Lambda constant region | QPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPT ECS |
| SEQ ID NO: 82 | Human heavy chain acceptor sequence VH1-18&JH6 FR1 21/28&JH4 FR1 | QVQLVQSGAEVKKPGASVKVSCKASGYTFT |
| SEQ ID NO: 83 | Human heavy chain acceptor sequence VH1-18&JH6 FR2 | WVRQAPGQGLEWMG |
| SEQ ID NO: 84 | Human heavy chain acceptor sequence VH1-18&JH6 FR3 | RVTMTTDTSTSTAYMELRSLRSDDTAVYYCAR |
| SEQ ID NO: 85 | Human heavy chain acceptor sequence VH1-18&JH6 FR4 VH2-26&JH6 FR4 VH1-46&JH6 FR4 | WGQGTTVTVSS |
| SEQ ID NO: 86 | Human heavy chain acceptor sequence 21/28&JH4 FR2 | WVRQAPGQRLEWMG |
| SEQ ID NO: 87 | Human heavy chain acceptor sequence 21/28&JH4 FR3 | RVTITRDTSASTAYMELSSLRSEDTAVYYCAR |
| SEQ ID NO: 88 | Human heavy chain acceptor sequence 21/28&JH4 FR4 M60&JH4 FR4 | WGQGTLVTVSS |
| SEQ ID NO: 89 | Human heavy chain acceptor sequence VH2-26&JH6 FR1 | QVTLKESGPVLVKPTETLTLTCTVSGFSLS |
| SEQ ID NO: 90 | Human heavy chain acceptor sequence VH2-26&JH6 FR2 | WIRQPPGKALEWLAH |

SEQUENCE SUMMARY

| Sequence Identifier | Protein | Sequence |
|---|---|---|
| SEQ ID NO: 91 | Human heavy chain acceptor sequence VH2-26&JH6 FR3 | RLTISKDTSKSQVVLTMTNMDPVDTATYYCAR |
| SEQ ID NO: 92 | Human heavy chain acceptor sequence M60&JH4 FR1 | QVTLRESGPALVKPTQTLTLTCTLYGFSLS |
| SEQ ID NO: 93 | Human heavy chain acceptor sequence M60&JH4 FR2 | WIRQPPGKALEWLA |
| SEQ ID NO: 94 | Human heavy chain acceptor sequence M60&JH4 FR3 | RLTISKDTSKNQVVLTMTNMDPVDTATYYCAR |
| SEQ ID NO: 95 | Human heavy chain acceptor sequence VH1-46&JH6 FR3 | RVTMTRDTSTSTVYMELSSLRSEDTAVYYCAR |
| SEQ ID NO: 96 | Human light chain acceptor sequence A20&JK4 FR1 | DIQMTQSPSSLSASVGDRVTITC |
| SEQ ID NO: 97 | Human light chain acceptor sequence A20&JK4 FR2 | WYQQKPGKVPKLLIY |
| SEQ ID NO: 98 | Human light chain acceptor sequence A20&JK4 FR3 | GVPSRFSGSGSGTDFTLTISSLQPEDVATYYC |
| SEQ ID NO: 99 | Human light chain acceptor sequence A20&JK4 FR4 III-3R&JK4 FR4 A1&JK4 FR4 | FGGGTKVEIKR |
| SEQ ID NO: 100 | Human light chain acceptor sequence III-3R&JK4 FR3 | GVPSRISGSGSGTDFTFTISSLQPEDIATYYC |
| SEQ ID NO: 101 | Human light chain acceptor sequence A1&JK4 FR1 | DVVMTQSPLSLPVTLGQPASISC |
| SEQ ID NO: 102 | Human light chain acceptor sequence A1&JK4 FR2 | WFQQRPGQSPRRLIY |
| SEQ ID NO: 103 | Human light chain acceptor sequence A1&JK4 FR3 O1&JK2 FR3 | GVPDRFSGSGSGTDFTLKISRVEAEDVGVYYC |
| SEQ ID NO: 104 | Human light chain acceptor sequence O1&JK2 FR1 | DIVMTQTPLSLPVTPGEPASISC |

SEQUENCE SUMMARY

| Sequence Identifier | Protein | Sequence |
|---|---|---|
| SEQ ID NO: 105 | Human light chain acceptor sequence O1&JK2 FR2 | WYLQKPGQSPQLLIY |
| SEQ ID NO: 106 | Human light chain acceptor sequence O1&JK2 FR4 | FGQGTKLEIKR |
| SEQ ID NO: 107 | Human CD40 extracellular domain | EPPTACREKQYLINSQCCSLCQPGQKLVSDCTEF TETECLPCGESEFLDTWNRETHCHQHKYCDPNLG LRVQQKGTSETDTICTCEEGWHCTSEACESCV |
| SEQ ID NO: 108 | Consensus sequence of Variable light chain CDR1 | (K/R)SS(Q/K)SLL(N/H)S(G/−)N(Q/G)(K/N)(N/T)YL(T/Y) |
| SEQ ID NO: 109 | Consensus sequence of Variable light chain CDR2 | (W/R)(A/M)ST(R/L)(E/A)S |
| SEQ ID NO: 110 | Consensus sequence of Variable light chain CDR3 | (Q/M)(N/Q)(D/H)(Y/L)(T/E)YPLT |
| SEQ ID NO: 111 | Heavy chain CDR2 | YISSGRXNIYYADTVKG Where "X" is any amino acid other than T, D, V, L, I, M |
| SEQ ID NO: 112 | Heavy chain CDR2 | YISSGRXNIYYADTVKG Where "X" is any amino acid |
| SEQ ID NO: 113 | Light chain CDR1 | KSSQSLLNXGNQKNYLT where "X" is not amino acid residue Pro |
| SEQ ID NO: 114 | Human light chain acceptor sequence III-3R&JK4 FR2 | WYQQKPGKAPKLLIY |
| SEQ ID NO: 115 | Histidine tag | His His His His His His |

The invention claimed is:

1. A full-length antagonist anti-CD40 antibody comprising a heavy chain CDR1 comprising the amino acid sequence of SEQ ID NO:6, a heavy chain CDR2 comprising the amino acid sequence of SEQ ID NO:42, a heavy chain CDR3 comprising the amino acid sequence of SEQ ID NO:8, a light chain CDR1 comprising the amino acid sequence of SEQ ID NO:21, a light chain CDR2 comprising the amino acid sequence of SEQ ID NO:11, and a light chain CDR3 comprising the amino acid sequence of SEQ ID NO:12.

2. The anti-CD40 antibody of claim 1, wherein the antibody is humanized.

3. The anti-CD40 antibody of claim 1 or 2, wherein the antibody is substantially free of agonist activity.

4. A full-length antagonist anti-CD40 antibody comprising a heavy chain variable domain comprising the amino acid sequence of SEQ ID NO: 28, and a light chain variable domain comprising the amino acid sequence of SEQ ID NO: 20.

5. An anti-CD40 antibody comprising a heavy chain comprising the amino acid sequence of SEQ ID NO: 41, and a light chain comprising the amino acid sequence of SEQ ID NO: 40.

6. An anti-CD40 antibody comprising a heavy chain comprising the amino acid sequence of SEQ ID NO: 39, and a light chain comprising the amino acid sequence of SEQ ID No: 40.

7. The anti-CD40 antibody of claim 1, comprising a light chain variable domain comprising the amino acid sequence of SEQ ID NO: 20.

8. The anti-CD40 antibody of claim 1, comprising a heavy chain variable domain comprising the amino acid sequence of SEQ ID NO: 28.

9. The anti-CD40 antibody of claim 1 or 2, wherein the antibody is an IgG isotype.

10. The anti-CD40 antibody of claim 9, wherein the IgG isotype is IgG1.

11. The anti-CD40 antibody of claim 9, wherein the IgG isotype is IgG4.

12. The anti-CD40 antibody of claim 10, wherein the antibody comprises a human IgG1 constant domain comprising the amino acid sequence SEQ ID NO:2.

13. The anti-CD40 antibody of claim 10, wherein the antibody comprises a human IgG1 constant domain comprising the amino sequence of SEQ ID NO:3.

14. The anti-CD40 antibody of claim 1, wherein the antibody comprises a light chain human Ig kappa constant domain.

15. The anti-CD40 antibody of claim 1, wherein the antibody comprises a light chain human Ig lambda constant domain.

16. The anti-CD40 antibody of claim 14, wherein the human Ig kappa constant domain comprises the amino acid sequence of SEQ ID NO:4.

17. The anti-CD40 antibody of claim 15, wherein the human Ig lambda constant domain comprises the amino acid sequence of SEQ ID NO:81.

18. The pharmaceutical composition comprising the anti-CD40 antibody of claim 1, and a pharmaceutically acceptable carrier.

19. A pharmaceutical composition comprising the anti-CD40 antibody of claim 4, and a pharmaceutically acceptable carrier.

20. A pharmaceutical composition comprising the anti-CD40 antibody of claim 5, and a pharmaceutically acceptable carrier.

21. A pharmaceutical composition comprising the anti-CD40 antibody of claim 6, and a pharmaceutically acceptable carrier.

* * * * *

UNITED STATES PATENT AND TRADEMARK OFFICE
CERTIFICATE OF CORRECTION

| | |
|---|---|
| PATENT NO. | : 10,174,121 B2 |
| APPLICATION NO. | : 15/167598 |
| DATED | : January 8, 2019 |
| INVENTOR(S) | : Benatuil et al. |

It is certified that error appears in the above-identified patent and that said Letters Patent is hereby corrected as shown below:

On the Title Page

Item (72) Inventor is corrected to read:
-- Lorenzo Benatuil, Northborough, MA (US);
Bradford L. McRae, Northborough, MA (US);
Chung-Ming Hsieh, Newton, MA (US);
Rui Wang, Boom, Newton (US);
Gillian A. Kingsbury, Wayland, MA (US) --.

Signed and Sealed this
Fifth Day of November, 2019

Andrei Iancu
*Director of the United States Patent and Trademark Office*